United States Patent
Thompson et al.

(10) Patent No.: US 7,531,311 B2
(45) Date of Patent: May 12, 2009

(54) METHODS OF DETECTING OR DIAGNOSING INFLAMMATORY BOWEL DISEASE USING PROKINETICIN POLYNUCLEOTIDES

(75) Inventors: Penny J. Thompson, Snohomish, WA (US); Paul O. Sheppard, Granite Falls, WA (US)

(73) Assignee: Zymogenetics, Inc., Seattle, WA (US)

( * ) Notice: Subject to any disclaimer, the term of this patent is extended or adjusted under 35 U.S.C. 154(b) by 0 days.

(21) Appl. No.: 11/550,982

(22) Filed: Oct. 19, 2006

(65) Prior Publication Data

US 2007/0048778 A1 Mar. 1, 2007

Related U.S. Application Data

(63) Continuation of application No. 10/680,755, filed on Oct. 7, 2003, now Pat. No. 7,205,110.

(60) Provisional application No. 60/508,614, filed on Oct. 3, 2003, provisional application No. 60/508,603, filed on Oct. 3, 2003, provisional application No. 60/433,918, filed on Dec. 16, 2002, provisional application No. 60/434,116, filed on Dec. 16, 2002, provisional application No. 60/416,718, filed on Oct. 7, 2002, provisional application No. 60/416,719, filed on Oct. 7, 2002.

(51) Int. Cl.
*C12Q 1/68* (2006.01)
*C07H 21/04* (2006.01)

(52) U.S. Cl. .......................................... 435/6; 536/23.5

(58) Field of Classification Search ........................ None
See application file for complete search history.

(56) References Cited

U.S. PATENT DOCUMENTS

| | | | |
|---|---|---|---|
| 5,294,630 A | 3/1994 | Blake et al. | |
| 5,891,720 A | 4/1999 | Moore et al. | |
| 6,485,938 B1 | 11/2002 | Sheppard et al. | |
| 6,756,479 B2 | 6/2004 | Sheppard et al. | |
| 6,828,425 B2 | 12/2004 | Sheppard et al. | |
| 7,045,299 B2 * | 5/2006 | Ohtaki et al. | 435/7.1 |
| 7,052,674 B2 * | 5/2006 | Zhou et al. | 424/9.1 |
| 7,122,349 B2 | 10/2006 | Sheppard et al. | |
| 7,179,787 B2 | 2/2007 | Sheppard et al. | |
| 7,205,110 B2 | 4/2007 | Thompson et al. | |
| 7,264,801 B2 | 9/2007 | Ferrara et al. | |
| 7,291,589 B2 | 11/2007 | Thompson et al. | |
| 2002/0115610 A1 | 8/2002 | Zhou et al. | |
| 2002/0187523 A1 | 12/2002 | Tang et al. | |
| 2007/0042417 A1 | 2/2007 | Sheppard et al. | |
| 2007/0042960 A1 | 2/2007 | Sheppard et al. | |
| 2007/0048258 A1 | 3/2007 | Thompson et al. | |
| 2007/0048805 A1 | 3/2007 | Sheppard et al. | |
| 2007/0048840 A1 | 3/2007 | Thompson et al. | |
| 2007/0049526 A1 | 3/2007 | Thompson et al. | |
| 2007/0053907 A1 | 3/2007 | Thompson et al. | |
| 2007/0053908 A1 | 3/2007 | Thompson et al. | |
| 2007/0065403 A1 | 3/2007 | Thompson et al. | |
| 2007/0065404 A1 | 3/2007 | Thompson et al. | |
| 2007/0065405 A1 | 3/2007 | Thompson et al. | |
| 2007/0078259 A1 | 4/2007 | Thompson et al. | |
| 2007/0087414 A1 | 4/2007 | Thompson et al. | |
| 2007/0092912 A1 | 4/2007 | Thompson et al. | |
| 2007/0172889 A1 | 7/2007 | Sheppard et al. | |

FOREIGN PATENT DOCUMENTS

| | | |
|---|---|---|
| EP | 1589033 | 10/2005 |
| EP | 1688434 | 8/2006 |
| WO | WO99/06550 | 2/1999 |
| WO | WO99/63088 | 12/1999 |
| WO | WO 03/040326 | 5/2003 |
| WO | WO 2004/031367 | 4/2004 |
| WO | WO 2004/065419 | 8/2004 |
| WO | WO 2004/081229 | 9/2004 |
| WO | WO 2005/037870 | 4/2005 |

OTHER PUBLICATIONS

Panes J., Acta Phys. Scand. 173: 159-165, 2001.*
Fedi, et al., "Isolation and Biological Characterization of the Human Dkk-1 Homologue, a Novel Inhibitor of Mammalian Wnt Signaling," *J. Biol. Chem. 274*(27): 19465-19472, Jul. 2, 1999.
Hsieh et al., "A new secreted protein that binds to Wnt proteins and inhibits their activities," *Nature 398*: 431-436, Apr. 1, 1999.
Jilek et al., "Murine Bv8 gene maps near a synteny breakpoint of mouse chromosome 6 and human 3p21," *Gene 256*: 189-195, 2000.
Li et al., "Identification of Two Prokineticin cDNAs: Recombinant Proteins Potently Contract Gastrointestinal Smooth Muscle," *Molec. Pharmacol. 59*(4): 692-698, Apr. 2001.
Weschelberger et al., "The mammalian homologues of frog Bv8 are mainly expressed in spermatocytes," *FEBS Lett. 462*: 177-181, 1999.
EMBL Database Accession No. AF182069, Oct. 2, 2000.
EMBL Database Accession No. AF333024, May 5, 2001.
EMBL Database Accession No. AF333025, May 5, 2001.
EMBL Database Accession No. AF182066, Dec. 14, 1999.
International Search Report in application No. PCT/US00/31278.
Schweitz et al., "MIT1, a black mamba toxin with a new and highly potent activity on intestinal contraction," *FEBS Lett. 461*: 183-188, 1999.
Boisbouvier et al., "A Structural Homologue of Colipase in Black Mamba Venom Revealed by NMR Floating Disulphide Bridge Analysis," *J. Mol. Biol. 283*: 205-219, 1998.
Joubert et al., "The Amino Acid Sequence of Protein A from *Dendroaspis polylepis polylepis* (Black mamba) Venom," *Hoppe-Seyler's Z. Physiol. Chem. Bd. 361*: 1787-1794, Dec. 1980.

(Continued)

*Primary Examiner*—Robert Landsman
*Assistant Examiner*—Gyan Chandra
(74) *Attorney, Agent, or Firm*—Knobbe Martens Olson & Bear LLP

(57) ABSTRACT

The present invention provides methods of using Zven1 and Zven2 polypeptides to increase chemokine production. The present invention also provides methods of using antagonists to Zven1 and Zven2 to treat inflammation in the intestine.

14 Claims, No Drawings

OTHER PUBLICATIONS

Morrison et al., "Genetically Engineered Antibody Molecules," *Advances in Immunology 44*: 65-92, 1989.

Harlow and Lane, "Antibodies A Laboratory Manual," *Cold Spring Harbor Laboratory*, pp. 76, 361, 476, 555, and 626, 1988.

Bassil et al., "Prokineticin-2, motilin, ghrelin and metoclopramide: Prokinetic utility in mouse stomach and colon", European Journal of Pharmacology 524:138-144, 2005.

Mollay et al., "Bv8, a small protein from frog skin and its homologue from snake venom induce hyperalgensia in rats," Euro J Pharmacol. 374: 189-196, 1999.

WPI Accession No. 2004-593431, 2004.

WPI Accession No. 2005-322854, 2005.

International Search Report dated Dec. 6, 2004 for Application No. PCT/US03/31562, filed Oct. 7, 2003.

* cited by examiner

METHODS OF DETECTING OR DIAGNOSING INFLAMMATORY BOWEL DISEASE USING PROKINETICIN POLYNUCLEOTIDES

CROSS-REFERENCE TO RELATED APPLICATIONS

This application is a continuation of U.S. application Ser. No. 10/680,755, filed Oct. 7, 2003, now U.S. Pat. No. 7,205,110, which claims the benefit of U.S. Provisional Application Ser. No. 60/416,719, filed Oct. 7, 2002, U.S. Provisional Application Ser. No. 60/416,718, filed Oct. 7, 2002, U.S. Provisional Application Ser. No. 60/434,116, filed Dec. 16, 2002, U.S. Provisional Application Ser. No. 60/433,918, filed Dec. 16, 2002, U.S. Provisional Application Ser. No. 60/508,614, filed Oct. 3, 2003 and U.S. Provisional Application Ser. No. 60/508,603, filed Oct. 3, 2003, all of which are herein incorporated by reference.

BACKGROUND OF THE INVENTION

In the United States approximately 500,000 people suffer from inflammatory bowel disease, which can involve either or both the small and large bowel. Ulcerative colitis and Crohn's disease are the best-known forms of inflammatory bowel disease, and both are categorized as "idiopathic" inflammatory bowel disease because the etiology for them is unknown.

Ulcerative colitis involves the colon as a diffuse mucosal disease, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of ulcerative colitis is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form, releasing mucus, pus, and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for ulcerative colitis, treatments are focused on suppressing the abnormal inflammatory process in the colon lining. Treatments including corticosteroids immunosuppressives (e.g., azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

Crohn's disease can involve any part of the gastrointestinal tract, but most frequently involves the distal small bowel and colon. Inflammation can produce anything from a small ulcer over a lymphoid follicle to a deep fissuring ulcer to transmural scarring and chronic inflammation. Although the etiology is unknown, infectious and immunologic mechanisms have been proposed. Symptoms are variable and can include diarrhea, fever, and pain, as well as extra-intestinal manifestations of arthritis, uveitis, erythema nodosum, and ankylosing spondylitis.

The traditional approach to treating inflammatory bowel disease is immunosuppression with azathioprine (see, for example, Rutgeerts, *J. Gastroenterol. Hepatol.* 17(*Suppl*): S176-85 (2002)). More recently, the chimeric monoclonal anti-tumor necrosis factor antibody, infliximab, has been used to target specific pathogenic disease mechanisms, and allows thorough suppression of the disease process and healing of the bowel in the long term. However, this therapy is associated with problems of immunogenicity. The formation of antibodies to infliximab interferes with efficacy and is associated with infusion reactions.

Irritable bowel syndrome (IBS) is a chronic functional gastrointestinal disorder. It is a heterogeneous condition characterized by a variety of bowel symptoms including abdominal pain and bloating which are usually associated with altered bowel habit (Collins et al, 2001). It is estimated that between 12 and 20% of the U.S. population suffer from this condition. Differing criteria have been proposed for defining IBS, including the Manning criteria (Manning et al, 1978), the Rome criteria (Thompson et al, 1992), and most recently Rome II (Thompson et al., 1999). Research reports on IBS frequently classify patients with IBS into the two subtypes of constipation predominant (CON) and diarrhea predominant (DIA) and sometimes include a third subtype of alternating pattern (ALT). Prokinetic agents have been a used in treatment of IBS CON for decades. (Callahan, M. *J. Clin. Gastroenterol* 35 *Supp*: S58-S67, 2002)

Thus, a need still exists for therapeutic approaches to diagnosis and treatment of inflammatory bowel disease and irritable bowel syndrome.

BRIEF SUMMARY OF THE INVENTION

The present invention provides proteins useful for the treatment of inflammatory bowel disease and irritable bowel syndrome. Other uses of Zven1 and Zven2 polypeptides are described in more detail below.

DESCRIPTION OF THE INVENTION

1. Overview

The present invention is directed to novel uses of previously described proteins, Zven1 and Zven2. See U.S. patent application Ser. No. 09/712,529, now issued as U.S. patent Ser. No. 6,485,938. Zven1 and Zven2 are also known in the industry as Prokineticin2 and Prokineticin1, respectively. As discussed herein, Zven1 and Zven2, as well as variants, fragments, and molecules having anti-Zven activity, can be used to regulate gastrointestinal function, symptoms related to IBD and IBS, and gastric emptying. Receptors for Zven1 (Prokineticin2) and Zven2 (Prokineticin1) have been identified as G protein-coupled receptors, GPCR73a and GPCR73b. See Lin, D. et al., *J. Biol. Chem.* 277: 19276-19280, 2002. The GPCR73a and GPCR73b receptors are also known as PK-R1 and PK-R2.

The present invention provides methods of using human Zven polypeptides and nucleic acid molecules that encode human Zven polypeptides. An illustrative nucleic acid molecule containing a sequence that encodes the Zven1 polypeptide has the nucleotide sequence of SEQ ID NO:1. The encoded polypeptide has the following amino acid sequence:

MRSLCCAPLL LLLLLPPLLL TPRAGDAAVI TGACDKDSQC GGGMCCAVSI WVKSIRICTP MGKLGDSCHP LTRKVPFFGR RMHHTCPCLP GLACLRTSFN RFICLAQK (SEQ ID NO:2). Thus, the Zven1 nucleotide sequence described herein encodes a polypeptide of 108 amino acids. The putative signal sequences of Zven1 polypeptide reside at amino acid residues 1 to 20, 1 to 21, and 1 to 22 of SEQ ID NO:2. The mature form of the polypeptide comprises the amino acid sequence from amino acid 28 to 108 as shown in SEQ ID NO:2.

A longer form of the sequence as shown in SEQ ID NO:2 is included in the invention described herein. The longer form has the following amino acid sequence: MRSLCCAPLL LLLLLPPLLL TPRAGDAAVI TGACDKDSQC GGGMCCAVSI WVKSIRICTP MGKLGDSCHP LTRKNNFGNG RQERRKRKRS KRKKEVPFFG RRMHHTCPCL PGLACLRTSF NRFICLAQK (SEQ ID NO:29). The putative signal sequence of the longer form has a mature form that comprises the amino acid sequence from amino acid 28 to 129 as shown in SEQ ID NO:29.

An illustrative nucleic acid molecule containing a sequence that encodes the Zven2 polypeptide has the nucleotide sequence of SEQ ID NO:4. The encoded polypeptide has the following amino acid sequence: MRGATRVSIM LLLVTVSDCA VITGACERDV QCGAGTCCAI SLWLRGLRMC TPLGREGEEC HPGSHKVPFF RKRKHHTCPC LPNLLCSRFP DGRYRCSMDL KNINF (SEQ ID NO:5). Thus, the Zven2 nucleotide sequence described herein encodes a polypeptide of 105 amino acids. The putative signal sequences of Zven2 polypeptide reside at amino acid residues 1 to 17, and 1 to 19 of SEQ ID NO:5.

As described below, the present invention provides isolated polypeptides comprising an amino acid sequence that is at least 70%, at least 75%, at least 80%, at least 85%, at least 90%, or at least 95% identical to amino acid residues 23 to 108 of SEQ ID NO:2, to amino acid residues 28 to 108 of SEQ ID NO:2, or to amino acid residues 28 to 129 if SEQ ID NO:29. Certain of such isolated polypeptides can specifically bind with an antibody that specifically binds with a polypeptide consisting of the amino acid sequence of SEQ ID NO:2. Particular polypeptides can increase or decrease gastric contractility, gastric emptying and/or intestinal transit. An illustrative polypeptide is a polypeptide that comprises the amino acid sequence of SEQ ID NO:2.

Similarly, the present invention includes provides isolated polypeptides comprising an amino acid sequence that is at least 70%, at least 75%, at least 80%, at least 85%, at least 90%, or at least 95% identical to amino acid residues 20 to 105 of SEQ ID NO:5, wherein such isolated polypeptides can specifically bind with an antibody that specifically binds with a polypeptide consisting of the amino acid sequence of SEQ ID NO:5. An illustrative polypeptide is a polypeptide that comprises the amino acid sequence of SEQ ID NO:5.

The present invention also provides polypeptides comprising an amino acid sequence selected from the group consisting of: (1) amino acid residues 21 to 108 of SEQ ID NO:2, (2) amino acid residues 22 to 108 of SEQ ID NO:2, (3) amino acid residues 23 to 108 of SEQ ID NO:2, (4) amino acid residues 82 to 108 of SEQ ID NO:2, (5) amino acid residues 1 to 78 (amide) of SEQ ID NO:2, (6) amino acid residues 1 to 79 of SEQ ID NO:2, (7) amino acid residues 21 to 78 (amide) of SEQ ID NO:2, (8) amino acid residues 21 to 79 of SEQ ID NO:2, (9) amino acid residues 22 to 78 (amide) of SEQ ID NO:2, (10) amino acid residues 22 to 79 of SEQ ID NO:2, (11) amino acid residues 23 to 78 (amide) of SEQ ID NO:2, (12) amino acid residues 23 to 79 of SEQ ID NO:2, (13) amino acid residues 20 to 108 of SEQ ID NO:2, (14) amino acid residues 20 to 72 of SEQ ID NO:2, (15) amino acid residues 20 to 79 of SEQ ID NO:2, (16) amino acid residues 20 to 79 (amide) of SEQ ID NO:2, (17) amino acid residues 21 to 72 of SEQ ID NO:2, (18) amino acid residues 21 to 79 (amide) of SEQ ID NO:2, (19) amino acid residues 22 to 72 of SEQ ID NO:2, (20) amino acid residues 22 to 79 (amide) of SEQ ID NO:2, (21) amino acid residues 23 to 72 of SEQ ID NO:2, (22) amino acid residues 23 to 79 (amide) of SEQ ID NO:2, (23) amino acid residues 28 to 108 of SEQ ID NO:2, (24) amino acid residues 28 to 72 of SEQ ID NO:2, (25) amino acid residues 28 to 79 of SEQ ID NO:2, (26) amino acid residues 28 to 79 (amide) of SEQ ID NO:2, (27) amino acid residues 75 to 108 of SEQ ID NO:2, (28) amino acid residues 75 to 79 of SEQ ID NO:2, and (29) amino acid residues 75 to 78 (amide) of SEQ ID NO:2. Illustrative polypeptides consist of amino acid sequences (1) to (29). The present invention also included polypeptide comprising an amino acid sequence comprising amino acid 28 to 129 as shown in SEQ ID NO:29, and/or fragments thereof.

The present invention further includes polypeptides comprising an amino acid sequence selected from the group consisting of: (a) amino acid residues 20 to 105 of SEQ ID NO:5, (b) amino acid residues 18 to 105 of SEQ ID NO:5, (c) amino acid residues 1 to 70 of SEQ ID NO:5, (d) amino acid residues 20 to 70 of SEQ ID NO:5, (e) amino acid residues 18 to 70 of SEQ ID NO:5, (f) amino acid residues 76 to 105 of SEQ ID NO:5, (g) amino acid residues 66 to 105 of SEQ ID NO:5, and (h) amino acid residues 82 to 105 of SEQ ID NO:5. Illustrative polypeptides consist of amino acid sequences (a) to (h).

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. The present invention also includes anti-idiotype antibodies that specifically bind with such antibodies or antibody fragments. The present invention further includes compositions comprising a carrier and a peptide, polypeptide, antibody, or anti-idiotype antibody described herein.

The present invention also provides isolated nucleic acid molecules that encode a Zven polypeptide, wherein the nucleic acid molecule is selected from the group consisting of (a) a nucleic acid molecule comprising the nucleotide sequence of SEQ ID NO:3, (b) a nucleic acid molecule encoding the amino acid sequence of SEQ ID NO:2, (c) a nucleic acid molecule that remains hybridized following stringent wash conditions to a nucleic acid molecule consisting of the nucleotide sequence of nucleotides 66 to 161 of SEQ ID NO:1, the nucleotide sequence of nucleotides 288 to 389 of SEQ ID NO:1, or to the complement of the nucleotide sequence of either nucleotides 66 to 161 of SEQ ID NO:1 or nucleotides 288 to 389 of SEQ ID NO:1, (d) a nucleic acid molecule comprising the nucleotide sequence of SEQ ID NO:6, (e) a nucleic acid molecule encoding the amino acid sequence of SEQ ID NO:5, (f) a nucleic acid molecule that remains hybridized following stringent wash conditions to a nucleic acid molecule consisting of the nucleotide sequence of nucleotides 334 to 405 of SEQ ID NO:4, or to the complement of the nucleotide sequence of nucleotides 334 to 405 of SEQ ID NO:4.

Illustrative nucleic acid molecules include those in which any difference between the amino acid sequence encoded by the nucleic acid molecule and the corresponding amino acid sequence of either SEQ ID NO:2 or SEQ ID NO:5 is due to a conservative amino acid substitution. The present invention further contemplates isolated nucleic acid molecules that comprise a nucleotide sequence of nucleotides 132 to 389 of SEQ ID NO:1, nucleotides 147 to 389 of SEQ ID NO:1, and nucleotides 148 to 405 of SEQ ID NO:4.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells comprising these vectors and expression vectors. Illustrative host cells include bacterial, yeast, avian, fungal, insect, mammalian, and plant cells. Recombinant host cells comprising such expression vectors can be used to prepare Zven polypeptides by culturing such recombinant host cells that comprise the expression vector and that produce the Zven protein, and, optionally, isolating the Zven protein from the cultured recombinant host cells. The present invention further includes products made by such processes.

In addition, the present invention provides pharmaceutical compositions comprising a pharmaceutically acceptable carrier and at least one of such an expression vector or recombinant virus comprising such expression vectors.

The present invention also contemplates methods for detecting the presence of Zven1 RNA in a biological sample, comprising the steps of (a) contacting a Zven1 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of SEQ ID NO:1, or its complement, and (b) detecting the formation of hybrids of the nucleic acid probe and either the test RNA molecules or the synthesized nucleic acid molecules, wherein the presence of the hybrids indicates the presence of Zven1 RNA in the biological sample. Analogous methods can be used to detect the presence of Zven2 RNA in a biological sample, wherein the probe has a nucleotide sequence comprising a portion of the nucleotide sequence of SEQ ID NO:4, or its complement.

The present invention further provides methods for detecting the presence of Zven polypeptide in a biological sample, comprising the steps of: (a) contacting the biological sample with an antibody or an antibody fragment that specifically binds with a polypeptide either consisting of the amino acid sequence of SEQ ID NO:2 or consisting of the amino acid sequence of SEQ ID NO:5, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold.

Illustrative biological samples include human tissue, such as an autopsy sample, a biopsy sample, body fluids and digestive components, and the like.

The present invention also provides kits for performing these detection methods. For example, a kit for detection of Zven1 gene expression may comprise a container that comprises a nucleic acid molecule, wherein the nucleic acid molecule is selected from the group consisting of (a) a nucleic acid molecule comprising the nucleotide sequence of nucleotides 66 to 161 of SEQ ID NO:1, (b) a nucleic acid molecule comprising the nucleotide sequence of nucleotides 288 to 389 of SEQ ID NO:1, (c) a nucleic acid molecule comprising the complement of the nucleotide sequence of nucleic acid molecules (a) or (b), (d) a nucleic acid molecule that is a fragment of (a) consisting of at least eight nucleotides, (e) a nucleic acid molecule that is a fragment of (b) consisting of at least eight nucleotides, (f) a nucleic acid molecule that is a fragment of (c) consisting of at least eight nucleotides, and (g) a nucleic acid molecule that is a fragment of or consists of the nucleic acid sequence as shown in SEQ ID NO: 12, 13, 15, 16, 17, 18, 19, 20, 23, or 24. A kit for detection of Zven2 gene expression may comprise a container that comprises a nucleic acid molecule, wherein the nucleic acid molecule is selected from the group consisting of (a) a nucleic acid molecule comprising the nucleotide sequence of nucleotides 334 to 405 of SEQ ID NO:4, (b) a nucleic acid molecule comprising the complement of the nucleotide sequence of (a), (c) a nucleic acid molecule that is a fragment of (a) consisting of at least eight nucleotides, and (d) a nucleic acid molecule that is a fragment of (b) consisting of at least eight nucleotides. Such kits may also comprise a second container that comprises one or more reagents capable of indicating the presence of the nucleic acid molecule.

On the other hand, a kit for detection of Zven protein may comprise a container that comprises an antibody, or an antibody fragment, that specifically binds with a polypeptide consisting of the amino acid sequence of SEQ ID NO:2 or consisting of the amino acid sequence of SEQ ID NO:5.

The present invention also contemplates anti-idiotype antibodies, or anti-idiotype antibody fragments, that specifically bind an antibody or antibody fragment that specifically binds a polypeptide consisting of the amino acid sequence of SEQ ID NO:2 or the amino acid sequence of SEQ ID NO:5.

The present invention further provides variant Zven1 polypeptides, which comprise an amino acid sequence that shares an identity with the amino acid sequence of SEQ ID NO:2 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:2 is due to one or more conservative amino acid substitutions. Illustrative variant Zven2 polypeptides, which comprise an amino acid sequence that shares an identity with the amino acid sequence of SEQ ID NO:5 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:5 is due to one or more conservative amino acid substitutions.

The present invention also provides fusion proteins comprising a Zven1 polypeptide moiety or a Zven2 polypeptide moiety. Such fusion proteins can further comprise an immunoglobulin moiety. A suitable immunoglobulin moiety is an immunoglobulin heavy chain constant region, such as a human $F_c$ fragment. The present invention also includes isolated nucleic acid molecules that encode such fusion proteins.

The present invention further provides a method of treating defective ileal contractility disease in a mammalian subject in need of such treatment, comprising: administering to the mammalian subject a Zven1 polypeptide, wherein the Zven1 polypeptide comprises the amino acid sequence of amino acid residues 23 to 108 of SEQ ID NO:2. In one embodiment, the disease is diabetes mellitus. In another method, the disease is post-operative ileus. In another embodiment, the disease is sepsis-related gastrointestinal stasis or ileus.

The present invention further provides a method of treating defective ileal contractility disease in a mammalian subject in need of such treatment, comprising: administering to the mammalian subject a Zven1 polypeptide, wherein the Zven1 polypeptide comprises the amino acid sequence of amino acid residues 28 to 108 of SEQ ID NO:2, the amino acid sequence of amino acid residues 20 to 105 of SEQ ID NO:5, or the amino acid sequence of amino acid residues 28 to 129 of SEQ ID NO:29. In one embodiment, the disease is diabetes mellitus. In another embodiment, the disease is post-operative ileus. In another embodiment, the disease is sepsis-related gastrointestinal stasis or ileus.

The invention also provides a method of reducing inflammation in the intestine of a mammal in need thereof, comprising administering to the mammal a Zven1 or Zven2 antagonist, wherein the inflammation in the intestine is reduced. In an embodiment, the antagonist is an antibody. In another embodiment, the antagonist is selected from: anti-idiotype antibodies; antibody fragments; chimeric antibodies; and humanized antibodies In an embodiment, the antagonist is a receptor, and wherein the receptor binds the amino acid sequence as shown in SEQ ID NO:2, SEQ ID NO:29, or SEQ ID NO:5. In another embodiment the receptor comprises the amino acid sequence as shown in SEQ ID NO:27 or in SEQ ID NO:28. In another embodiment, the antagonist is a portion of a receptor, and wherein that portion of the receptor specifically binds to the amino acid sequence as shown in SEQ ID NO:2, SEQ ID NO:29, or as shown in SEQ ID NO:5. In another embodiment, the inflammation is chronic. In another embodiment, the inflammation is sporadic. In another embodiment, the inflammation is a symptom of irritable bowel syndrome. In another embodiment, the inflammation is a symptom of inflammatory bowel disease. In a further embodiment, the inflammatory bowel disease is ulcerative colitis or Crohn's disease.

The invention also provides a method of treating inflammation in the intestine of a mammal in need thereof, comprising administering to the mammal a Zven1 or Zven2 antagonist, wherein the inflammation in the intestine is reduced. In an embodiment, the antagonist is an antibody. In another embodiment, the antagonist is selected from: anti-idiotype antibodies; antibody fragments; chimeric antibodies; and humanized antibodies. In another embodiment, the antagonist is a receptor, and wherein the receptor binds the amino acid sequence as shown in SEQ ID NO:2, SEQ ID NO:29, or SEQ ID NO:5. In another embodiment, the receptor comprises the amino acid sequence as shown in SEQ ID NO:27 or SEQ ID NO:28. In an embodiment, the antagonist is a portion a receptor, and that portion of the receptor specifically binds to the amino acid sequence as shown in SEQ ID NO:2, SEQ ID NO:29, or as shown in SEQ ID NO:5. In another embodiment, the inflammation is chronic. In another embodiment, the inflammation is sporadic. In another embodiment, the inflammation is a symptom of irritable bowel syndrome. In another embodiment, the inflammation is a symptom inflammatory bowel disease. In a further embodiment, the the inflammatory bowel disease is ulcerative colitis, Crohn's disease, or diarrhea-prone irritable bowel syndrome.

The invention also provides a method of detecting inflammatory bowel disease in a biological sample, comprising screening the sample for the polynucleotide sequence of SEQ ID NO:1, or SEQ ID NO:4 or a fragment thereof.

The invention also provides a method of detecting inflammatory bowel disease in a biological sample, comprising screening the sample for the polypeptide sequence as shown in SEQ ID NO:2, SEQ ID NO:29, or SEQ ID NO:5 or a fragment thereof.

The invention also provides a method of detecting irritable bowel syndrome in a biological sample, comprising screening the sample for the polypeptide sequence as shown in SEQ ID NO:2, SEQ ID NO:29, or SEQ ID NO:5 or a fragment thereof.

The invention also provides a method of detecting inflammatory bowel disease in a biological sample, comprising screening the sample for the polynucleotide sequence as shown in SEQ ID NO:1 or SEQ ID NO:4, or a fragment thereof.

The invention also provides a method of diagnosing inflammatory bowel disease in a biological sample, comprising screening the sample for the polynucleotide sequence of SEQ ID NO:1, or SEQ ID NO:4 or a fragment thereof.

The invention also provides a method of diagnosing inflammatory bowel disease in a biological sample, comprising screening the sample for the polypeptide sequence as shown in SEQ ID NO:2, SEQ ID NO:29, or SEQ ID NO:5 or a fragment thereof.

The invention also provides a method of diagnosing irritable bowel syndrome in a biological sample, comprising screening the sample for the polypeptide sequence as shown in SEQ ID NO:2, SEQ ID NO:29, or SEQ ID NO:5 or a fragment thereof.

The invention also provides a method of diagnosing inflammatory bowel disease in a biological sample, comprising screening the sample for the polynucleotide sequence as shown in SEQ ID NO:1 or SEQ ID NO:4, or a fragment thereof.

The invention also provides a method of treating treating inflammatory bowel disease in a mammal in need thereof, comprising administering to the mammal a polypeptide, wherein the polypeptide comprises the amino acid sequence of amino acid residues 28 to 108 of SEQ ID NO:2, amino acid residues 28 to 129 of SEQ ID NO:29, or amino acid residues 20 to 105 of SEQ ID NO:5.

The invention also provides a method of treating treating irritable bowel syndrome in a mammal in need thereof, comprising administering to the mammal a polypeptide, wherein the polypeptide comprises the amino acid sequence of amino acid residues 28 to 108 of SEQ ID NO:2, amino acid residues 28 to 129 of SEQ ID NO:29, or amino acid residues 20 to 105 of SEQ ID NO:5.

The invention also provides a method of treating treating irritable bowel syndrome in a mammal in need thereof, comprising administering to the mammal a polynucleotide, wherein the polynucleotide comprises the nucleic acid sequence of SEQ ID NO:1 or of SEQ ID NO:5.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces a Zven1 or Zven2 peptide or polypeptide from an expression vector. In contrast, such polypeptides can be produced by a cell that is a "natural source" of Zven1 or Zven2, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a Zven1 or Zven2 polypeptide fused with a polypeptide that binds an affinity matrix. Such a fusion protein provides a means to isolate large quantities of Zven1 or Zven2 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ M$^{-1}$.

An "anti-idiotype antibody" is an antibody that binds with the variable region domain of an immunoglobulin. In the present context, an anti-idiotype antibody binds with the variable region of an anti-Zven1 or anti-Zven2 antibody, and thus, an anti-idiotype antibody mimics an epitope of Zven1 or Zven2.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-Zven1 monoclonal antibody fragment binds with an epitope of Zven1.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNAs encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide, which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for Zven1" or a "Zven1 anti-sense oligonucleotide" is an oligonucleotide having a sequence (a) capable of forming a stable triplex with a portion of the Zven1 gene, or (b) capable of forming a stable duplex with a portion of an mRNA transcript of the Zven1 gene. Similarly, an "anti-sense oligonucleotide specific for Zven2" or a "Zven2 anti-sense oligonucleotide" is an oligonucleotide having a sequence (a) capable of forming a stable triplex with a portion of the Zven2 gene, or (b) capable of forming a stable duplex with a portion of an mRNA transcript of the Zven2 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant Zven1 gene" refers to nucleic acid molecules that encode a polypeptide having an amino acid sequence that is a modification of SEQ ID NO:2. Such variants include naturally-occurring polymorphisms of Zven1 genes, as well as synthetic genes that contain conservative amino acid substitutions of the amino acid sequence of SEQ ID NO:2. Additional variant forms of Zven1 genes are nucleic acid molecules that contain insertions or deletions of the nucleotide sequences described herein. A variant Zven1 gene can be identified by determining whether the gene hybridizes with a nucleic acid molecule having the nucleotide sequence of SEQ ID NO:1, or its complement, under stringent conditions. Similarly, a variant Zven2 gene and a variant Zven2 polypeptide can be identified with reference to SEQ ID NO:4 and SEQ ID NO:5, respectively.

Alternatively, variant Zven genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing,* 2nd Edition (Academic Press, Inc. 1998)). Particular methods for determining sequence identity are described below.

Regardless of the particular method used to identify a variant Zven1 gene or variant Zven1 polypeptide, a variant gene or polypeptide encoded by a variant gene may be characterized by its ability to bind specifically to an anti-Zven1 antibody. Similarly, a variant Zven2 gene product or variant Zven2 polypeptide may be characterized by its ability to bind specifically to an anti-Zven2 antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of Zven1 and Zven2 genes. Within the context of this invention, a "functional fragment" of a Zven1 (or Zven2) gene refers to a nucleic acid molecule that encodes a portion of a Zven1 (or Zven2) polypeptide, which specifically binds with an anti-Zven1 (anti-Zven2) antibody.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of Human Zven1 and Zven2 Genes

Nucleic acid molecules encoding a human Zven1 gene can be obtained by screening a human cDNA or genomic library using polynucleotide probes based upon SEQ ID NO:1. Similarly, nucleic acid molecules encoding a human Zven2 gene can be obtained by screening a human cDNA or genomic library using polynucleotide probes based upon SEQ ID NO:4. These techniques are standard and well-established.

As an illustration, a nucleic acid molecule that encodes a human Zven1 gene can be isolated from a human cDNA library. In this case, the first step would be to prepare the cDNA library by isolating RNA from tissues, such as testis or peripheral blood lymphocytes, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et a. (eds.), *Short Protocols in Molecular Biology,* $3^{rd}$ *Edition*, pages 4-1 to 4-6 (John Wiley & Sons 1995) ["Ausubel (1995) "]; Wu et al, *Methods in Gene Biotechnology*, pages 33-41 (CRC Press, Inc. 1997) ["Wu (1997)"]). Alternatively, total RNA can be isolated from tissue by extracting ground tissue with guanidinium isothiocyanate, extracting with organic solvents, and separating RNA from contaminants using differential centrifugation (see, for example, Chirgwin et a., *Biochemistry* 18:52 (1979); Ausubel (1995) at pages 4-1 to 4-6; Wu (1997) at pages 33-41).

In order to construct a cDNA library, poly(A)$^+$ RNA must be isolated from a total RNA preparation. Poly(A)$^+$ RNA can be isolated from total RNA using the standard technique of oligo(dT)-cellulose chromatography (see, for example, Aviv and Leder, *Proc. Nat'l Acad. Sci. USA* 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41-46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λ gt11," in *DNA Cloning: A Practical Approach Vol. I*, Glover (ed.), page 49 (IRL Press, 1985); Wu (1997) at pages 47-52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A human genomic library can be prepared by means well-known in the art (see, for example, Ausubel (1995) at pages 5-1 to 5-6; Wu (1997) at pages 307-327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5-1 to 5-6; Wu 1997) at pages 307-327).

Nucleic acid molecules that encode a human Zven1 or Zven2 gene can also be obtained using the polymerase chain reaction (PCR) with oligonucleotide primers having nucleotide sequences that are based upon the nucleotide sequences described herein. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), pages 317-337 (Humana Press, Inc. 1993).

Alternatively, human genomic libraries can be obtained from commercial sources such as Research Genetics (Huntsville, Ala.) and the American Type Culture Collection (Manassas, Va.).

A library containing cDNA or genomic clones can be screened with one or more polynucleotide probes based upon SEQ ID NO:1, using standard methods (see, for example, Ausubel (1995) at pages 6-1 to 6-11).

Anti-Zven antibodies, produced as described below, can also be used to isolate DNA sequences that encode human Zven genes from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in *DNA Cloning 2: Expression Systems, 2nd Edition*, Glover et al. (eds.), pages 1-14 (Oxford University Press 1995)).

As an alternative, a Zven gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et a., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pastemak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

The sequence of a Zven cDNA or Zven genomic fragment can be determined using standard methods. Zven polynucleotide sequences disclosed herein can also be used as probes or primers to clone 5' non-coding regions of a Zven gene. Promoter elements from a Zven gene can be used to direct the expression of heterologous genes in tissues of, for example, transgenic animals or patients treated with gene therapy. The identification of genomic fragments containing a Zven promoter or regulatory element can be achieved using well-established techniques, such as deletion analysis (see, generally, Ausubel (1995)).

Cloning of 5' flanking sequences also facilitates production of Zven proteins by "gene activation," as disclosed in U.S. Pat. No. 5,641,670. Briefly, expression of an endogenous Zven gene in a cell is altered by introducing into the Zven locus a DNA construct comprising at least a targeting sequence, a regulatory sequence, an exon, and an unpaired splice donor site. The targeting sequence is a Zven 5' non-coding sequence that permits homologous recombination of the construct with the endogenous Zven locus, whereby the sequences within the construct become operably linked with the endogenous Zven coding sequence. In this way, an endogenous Zven promoter can be replaced or supplemented with other regulatory sequences to provide enhanced, tissue-specific, or otherwise regulated expression.

4. Production of Zven Gene Variants

The present invention provides a variety of nucleic acid molecules, including DNA and RNA molecules, which encode the Zven polypeptides disclosed herein. Those skilled in the art will readily recognize that, in view of the degeneracy of the genetic code, considerable sequence variation is possible among these polynucleotide molecules. SEQ ID NOs:3 and 6 are a degenerate nucleotide sequences that encompasses all nucleic acid molecules that encode the Zven polypeptides of SEQ ID NOs:2 and 5, respectively. Those skilled in the art will recognize that the degenerate sequence of SEQ ID NO:3 also provides all RNA sequences encoding SEQ ID NO:2, by substituting U for T, while the degenerate sequence of SEQ ID NO:6 also provides all RNA sequences encoding SEQ ID NO:5, by substituting U for T. Thus, the present invention contemplates Zven1 polypeptide-encoding nucleic acid molecules comprising nucleotide 66 to nucleotide 389 of SEQ ID NO:1, and their RNA equivalents, as well as Zven2 polypeptide-encoding nucleic acid molecules comprising nucleotide 91 to nucleotide 405 of SEQ ID NO:4, and their RNA equivalents.

Table 1 sets forth the one-letter codes used within SEQ ID NOs:3 and 6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3 and 6, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NOs:2 and 5. Variant sequences can be readily tested for functionality as described herein.

Different species can exhibit "preferential codon usage." In general, see, Grantham et al., *Nuc. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:3 and 6 serve as templates for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zven polypeptides from other mammalian species, including porcine, ovine, bovine, canine, feline, equine, and other primate polypeptides. Orthologs of human Zven can be cloned using information and compositions provided by the present invention in combination with conventional cloning techniques. For example, a cDNA can be cloned using mRNA obtained from a tissue or cell type that expresses Zven. Suitable sources of mRNA can be identified by probing northern blots with probes designed from the sequences disclosed herein. A library is then prepared from mRNA of a positive tissue or cell line.

A Zven-encoding cDNA molecule can then be isolated by a variety of methods, such as by probing with a complete or partial human cDNA or with one or more sets of degenerate probes based on the disclosed sequences. A cDNA can also be cloned using the polymerase chain reaction with primers designed from the representative human Zven sequences disclosed herein. Within an additional method, the cDNA library can be used to transform or transfect host cells, and expression of the cDNA of interest can be detected with an antibody to Zven polypeptide. Similar techniques can also be applied to the isolation of genomic clones.

Those skilled in the art will recognize that the sequences disclosed in SEQ ID NOs:1 and 4 represent single alleles of human Zven1 and Zven2, respectively, and that allelic variation and alternative splicing are expected to occur. Allelic variants of this sequence can be cloned by probing cDNA or genomic libraries from different individuals according to standard procedures. Allelic variants of the nucleotide sequences shown in SEQ ID NOs:1 and 4, including those containing silent mutations and those in which mutations result in amino acid sequence changes, are within the scope of the present invention, as are proteins which are allelic variants of SEQ ID NOs:2 and 5. cDNA molecules generated from alternatively spliced mRNAs, which retain the properties of the Zven polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules consisting of the nucleotide sequence of SEQ ID NO:1, to nucleic acid molecules consisting of the nucleotide sequence of nucleotides 66 to 161 of SEQ ID NO:1, to nucleic acid molecules consisting of the nucleotide sequence of nucleotides 288 to 389 of SEQ ID NO:1, to nucleic acid molecules consisting of the nucleotide sequence of SEQ ID NO:4, to nucleic acid molecules consisting of the nucleotide sequence of nucleotides 334 to 405 of SEQ ID NO:4, or to nucleic acid molecules consisting of nucleotide sequences that are the complements of such sequences. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5-25° C. below the $T_m$ of the hybrid and a hybridization buffer having up to 1 M Na$^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20-70° C. and a hybridization buffer containing up to 6×SSC and 0-50% formamide. A higher degree of stringency can be achieved at temperatures of from 40-70° C. with a hybridization buffer having up to 4×SSC and from 0-50% formamide. Highly stringent conditions typically encompass temperatures of 42-70° C. with a hybridization buffer having up to 1×SSC and 0-50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions that influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manunal*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a Na$^+$ source, such as SSC (1×SSC: 0.15 M sodium chloride, 15 mM sodium citrate) or SSPE (1×SSPE: 1.8 M NaCl, 10 mM NaH$_2$PO$_4$, 1 mM EDTA, pH 7.7). By decreasing the ionic concentration of the buffer, the stability of the hybrid is increased. Typically, hybridization buffers contain from between 10 mM-1 M Na$^+$. The addition of destabilizing or denaturing agents such as formamide, tetralkylammonium salts, guanidinium cations or thiocyanate cations to the hybridization solution will alter the T$_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant Zven1 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5× Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. For example, nucleic acid molecules encoding particular variant Zven1 polypeptides can remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. In a similar manner, nucleic acid molecules encoding particular Zven2 variants can remain hybridized with a nucleic acid molecule consisting of the nucleotide sequence of nucleotides 334 to 405 of SEQ ID NO:4, or its complement, following washing under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. As an illustration, nucleic acid molecules encoding particular variant Zven1 polypeptides can remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C. Similarly, nucleic acid molecules encoding particular Zven2 variants remain hybridized with a nucleic acid molecule consisting of the nucleotide sequence of nucleotides 334 to 405 of SEQ ID NO:4, or its complement, following washing under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated Zven1 polypeptides that have a substantially similar sequence identity to the polypeptides of SEQ ID NO:2, or their orthologs. The term "substantially similar sequence identity" is used herein to denote polypeptides having 85%, 90%, 95% or greater than 95% sequence identity to the sequences shown in SEQ ID NO:2, or their orthologs. Similarly, the present invention provides isolated Zven2 polypeptides having 85%, 90%, 95% or greater than 95% sequence identity to the sequences shown in SEQ ID NO:5, or their orthologs.

The present invention also contemplates Zven variant nucleic acid molecules that can be identified using two criteria: a determination of the similarity between the encoded polypeptide with the amino acid sequence of SEQ ID NOs:2 or 5, and a hybridization assay, as described above. For example, certain Zven1 gene variants include nucleic acid molecules (1) that remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under stringent washing conditions, in which the wash stringency is equivalent to 0.5×-2× SSC with 0.1% SDS at 55-65° C., and (2) that encode a polypeptide having 85%, 90%, 95% or greater than 95% sequence identity to the amino acid sequence of SEQ ID NO:2. Alternatively, certain Zven1 variant genes can be characterized as nucleic acid molecules (1) that remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under highly stringent washing conditions, in which the wash stringency is equivalent to 0.1×-0.2×SSC with 0.1% SDS at 50-65° C., and (2) that encode a polypeptide having 85%, 90%, 95% or greater than 95% sequence identity to the amino acid sequence of SEQ ID NO:2.

Moreover, certain Zven2 gene variants include nucleic acid molecules (1) that remain hybridized with a nucleic acid molecule consisting of the nucleotide sequence of nucleotides 334 to 405 of SEQ ID NO:4, or its complement, following washing under stringent washing conditions, in which the wash stringency is equivalent to 0.5×-2×SSC with 0.1% SDS at 55-65° C., and (2) that encode a polypeptide having 85%, 90%, 95% or greater than 95% sequence identity to the amino acid sequence of SEQ ID NO:5. Alternatively, certain Zven2 variant genes can be characterized as nucleic acid molecules (1) that remain hybridized with a nucleic acid molecule consisting of the nucleotide sequence of nucleotides 334 to 405 of SEQ ID NO:4, or its complement, following washing under highly stringent washing conditions, in which the wash stringency is equivalent to 0.1×-0.2×SSC with 0.1% SDS at 50-65° C., and (2) that encode a polypeptide having 85%, 90%, 95% or greater than 95% sequence identity to the amino acid sequence of SEQ ID NO:5.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, and most preferably, three. The other parameters can be set as: gap opening penalty=10, and gap extension penalty=1.

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 |   |   |   |   |   |   |   |   |   |   |   |   |   |   |   |   |   |   |   |
| R | -1 | 5 |   |   |   |   |   |   |   |   |   |   |   |   |   |   |   |   |   |   |
| N | -2 | 0 | 6 |   |   |   |   |   |   |   |   |   |   |   |   |   |   |   |   |   |
| D | -2 | -2 | 1 | 6 |   |   |   |   |   |   |   |   |   |   |   |   |   |   |   |   |
| C | 0 | -3 | -3 | -3 | 9 |   |   |   |   |   |   |   |   |   |   |   |   |   |   |   |
| Q | -1 | 1 | 0 | 0 | -3 | 5 |   |   |   |   |   |   |   |   |   |   |   |   |   |   |
| E | -1 | 0 | 0 | 2 | -4 | 2 | 5 |   |   |   |   |   |   |   |   |   |   |   |   |   |
| G | 0 | -2 | 0 | -1 | -3 | -2 | -2 | 6 |   |   |   |   |   |   |   |   |   |   |   |   |
| H | -2 | 0 | 1 | -1 | -3 | 0 | 0 | -2 | 8 |   |   |   |   |   |   |   |   |   |   |   |
| I | -1 | -3 | -3 | -3 | -1 | -3 | -3 | -4 | -3 | 4 |   |   |   |   |   |   |   |   |   |   |
| L | -1 | -2 | -3 | -4 | -1 | -2 | -3 | -4 | -3 | 2 | 4 |   |   |   |   |   |   |   |   |   |
| K | -1 | 2 | 0 | -1 | -3 | 1 | 1 | -2 | -1 | -3 | -2 | 5 |   |   |   |   |   |   |   |   |
| M | -1 | -1 | -2 | -3 | -1 | 0 | -2 | -3 | -2 | 1 | 2 | -1 | 5 |   |   |   |   |   |   |   |
| F | -2 | -3 | -3 | -3 | -2 | -3 | -3 | -3 | -1 | 0 | 0 | -3 | 0 | 6 |   |   |   |   |   |   |
| P | -1 | -2 | -2 | -1 | -3 | -1 | -1 | -2 | -2 | -3 | -3 | -1 | -2 | -4 | 7 |   |   |   |   |   |
| S | 1 | -1 | 1 | 0 | -1 | 0 | 0 | 0 | -1 | -2 | -2 | 0 | -1 | -2 | -1 | 4 |   |   |   |   |
| T | 0 | -1 | 0 | -1 | -1 | -1 | -1 | -2 | -2 | -1 | -1 | -1 | -1 | -2 | -1 | 1 | 5 |   |   |   |
| W | -3 | -3 | -4 | -4 | -2 | -2 | -3 | -2 | -2 | -3 | -2 | -3 | -1 | 1 | -4 | -3 | -2 | 11 |   |   |
| Y | -2 | -2 | -2 | -3 | -2 | -1 | -2 | -3 | 2 | -1 | -1 | -2 | -1 | 3 | -3 | -2 | -2 | 2 | 7 |   |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative Zven1 or Zven2 variant. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA The present invention includes nucleic acid molecules that encode a polypeptide having a conservative amino acid change, compared with the amino acid sequence of SEQ ID NOs:2 or 5. That is, variants can be obtained that contain one or more amino acid substitutions of SEQ ID NOs:2 or 5, in which an alkyl amino acid is substituted for an alkyl amino acid in a Zven1 or Zven2 amino acid sequence, an aromatic amino acid is substituted for an aromatic amino acid in a Zven1 or Zven2 amino acid sequence, a sulfur-containing amino acid is substituted for a sulfur-containing amino acid in a Zven1 or Zven2 amino acid sequence, a hydroxy-containing amino acid is substituted for a hydroxy-containing amino acid in a Zven1 or Zven2 amino acid sequence, an acidic amino acid is substituted for an acidic amino acid in a Zven1 or Zven2 amino acid sequence, a basic amino acid is substituted for a basic amino acid in a Zven1 or Zven2 amino acid sequence, or a dibasic monocarboxylic amino acid is substituted for a dibasic monocarboxylic amino acid in a Zven1 or Zven2 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of Zven1 or Zven2 are characterized by having at least 70%, at least 80%, at least 85%, at least 90%, at least 95% or greater than 95% sequence identity to a corresponding amino acid sequence disclosed herein (i.e., SEQ ID NO:2 or SEQ ID NO:5), wherein the variation in amino acid sequence is due to one or more conservative amino acid substitutions.

Conservative amino acid changes in a Zven1 gene and a Zven2 gene can be introduced by substituting nucleotides for the nucleotides recited in SEQ ID NO:1 and SEQ ID NO:4, respectively. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994).

Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for Zven amino acid residues.

Amino acid sequence analysis indicates that Zven1 and Zven2 share several motifs. For example, one motif is "AVIT-GAC[DE][KR]D" (SEQ ID NO:8), wherein acceptable amino acids for a given position are indicated within square brackets. This motif occurs in Zven1 at amino acid residues 28 to 37 of SEQ ID NO:2, and in Zven2 at amino acid residues 20 to 29 of SEQ ID NO:5. Another motif is "CHP[GL][ST][HR]KVPFFX[KR]RXHHTCPCLP" (SEQ ID NO:9), wherein acceptable amino acids for a given position are indicated within square brackets, and "X" can be any amino acid residue. This motif occurs in Zven1 at amino acid residues 68 to 90 in SEQ ID NO:2, and in Zven2 at amino acid residues 60 to 82 of SEQ ID NO:5. The present invention includes peptides and polypeptides comprising these motifs.

Sequence analysis also indicated that Zven1 and Zven2 include various conservative amino acid substitutions with respect to each other. Accordingly, particular Zven1 variants can be designed by modifying its sequence to include one or more amino acid substitutions corresponding with the Zven2 sequence, while particular Zven2 variants can be designed by modifying its sequence to include one or more amino acid substitutions corresponding with the Zven1 sequence. Such variants can be constructed using Table 4, which presents exemplary conservative amino acid found in Zven1 and Zven2. Although Zven1 and Zven2 variants can be designed with any number of amino acid substitutions, certain variants will include at least about X amino acid substitutions, wherein X is selected from the group consisting of 2, 5, 7, 10, 12, 14, 16, 18, and 20.

TABLE 4

| Zven1 | | Zven2 | |
| --- | --- | --- | --- |
| Amino acid Position (SEQ ID NO: 2) | Amino acid | Amino acid Position (SEQ ID NO: 5) | Amino acid |
| 4 | Leu | 4 | Ala |
| 7 | Ala | 7 | Val |
| 9 | Leu | 9 | Ile |
| 14 | Leu | 14 | Val |
| 35 | Asp | 27 | Glu |
| 36 | Lys | 28 | Arg |
| 42 | Gly | 34 | Ala |
| 48 | Val | 40 | Ile |
| 50 | Ile | 42 | Leu |
| 52 | Val | 44 | Leu |
| 53 | Lys | 45 | Arg |
| 55 | Ile | 47 | Leu |
| 63 | Lys | 55 | Arg |
| 66 | Asp | 58 | Glu |
| 71 | Leu | 63 | Gly |
| 72 | Thr | 64 | Ser |
| 73 | Arg | 65 | His |
| 80 | Arg | 72 | Lys |
| 93 | Ala | 85 | Leu |
| 102 | Phe | 94 | Tyr |

Essential amino acids in the polypeptides of the present invention can be identified according to procedures known in the art, such as site-directed mutagenesis or alanine-scanning mutagenesis (Cunningham and Wells, *Science* 244:1081

(1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity, such as the ability to bind to an antibody, to identify amino acid residues that are critical to the activity of the molecule. See also, Hilton et al., *J. Biol. Chem.* 271:4699 (1996).

The location of Zven1 or Zven2 receptor binding domains can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992). Moreover, Zven1 or Zven2 labeled with biotin or FITC can be used for expression cloning of Zven1 or Zven2 receptors.

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)).

Variants of the disclosed Zven1 or Zven2 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-Zven1 or anti-Zven2 antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of Zven1 or Zven2 polypeptides and nucleic acid molecules encoding such functional fragments. Routine deletion analyses of nucleic acid molecules can be performed to obtain functional fragments of a nucleic acid molecule that encodes a Zven1 or Zven2 polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for the ability to bind anti-Zven antibodies. One alternative to exonuclease digestion is to use oligonucleotide-directed mutagenesis to introduce deletions or stop codons to specify production of a desired fragment. Alternatively, particular fragments of a Zven gene can be synthesized using the polymerase chain reaction.

Methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation, Vol. I*, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a Zven1 or Zven2 gene that have amino acid changes, compared with the amino acid sequence of SEQ ID NO:2 or SEQ ID NO:5. A variant Zven gene can be identified on the basis of structure by determining the level of identity with the particular nucleotide and amino acid sequences disclosed herein. An alternative approach to identifying a variant gene on the basis of structure is to determine whether a nucleic acid molecule encoding a potential variant Zven1 or Zven2 gene can hybridize to a nucleic acid molecule having the nucleotide sequence of SEQ ID NO:1 or SEQ ID NO:4, as discussed above.

The present invention also provides polypeptide fragments or peptides comprising an epitope-bearing portion of a Zven1 or Zven2 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of SEQ ID NOs:2 or 5. Such epitope-bearing peptides and polypeptides can be produced by fragmenting a Zven1 or Zven2 polypeptide, or by chemical peptide synthesis, as described herein. Moreover, epitopes can be selected by phage display of random peptide libraries (see, for example, Lane and Stephen, Curr. Opin. Immunol. 5:268 (1993), and Cortese et al., Curr. Opin. Biotechnol. 7:616 (1996)). Standard methods for identifying epitopes and producing antibodies from small peptides that comprise an epitope are described, for example, by Mole, "Epitope Mapping," in Methods in Molecular Biology, Vol. 10, Manson (ed.), pages 105-116 (The Humana Press, Inc. 1992), Price, "Production and Characterization of Synthetic Peptide-Derived Antibodies," in Monoclonal Antibodies: Production, Engineering, and Clinical Application, Ritter and Ladyman (eds.), pages 60-84 (Cambridge University Press 1995), and Coligan et al. (eds.), Current Protocols in Immunology, pages 9.3.1-9.3.5 and pages 9.4.1-9.4.11 (John Wiley & Sons 1997).

Regardless of the particular nucleotide sequence of a variant Zven1 or Zven2 gene, the gene encodes a polypeptide that may be characterized by its ability to bind specifically to an anti-Zven1 or anti-Zven2 antibody.

In addition to the uses described above, polynucleotides and polypeptides of the present invention are useful as educational tools in laboratory practicum kits for courses related to genetics and molecular biology, protein chemistry, and antibody production and analysis. Due to its unique polynucleotide and polypeptide sequences, molecules of Zven1 or Zven2 can be used as standards or as "unknowns" for testing purposes. For example, Zven1 or Zven2 polynucleotides can be used as an aid, such as, for example, to teach a student how to prepare expression constructs for bacterial, viral, or mammalian expression, including fusion constructs, wherein Zven1 or Zven2 is the gene to be expressed; for determining the restriction endonuclease cleavage sites of the polynucleotides; determining mRNA and DNA localization of Zven1 or Zven2 polynucleotides in tissues (i.e., by northern and Southern blotting as well as polymerase chain reaction); and for identifying related polynucleotides and polypeptides by nucleic acid hybridization. As an illustration, students will find that PvuII digestion of a nucleic acid molecule consisting of the nucleotide sequence of nucleotides 66 to 389 of SEQ ID NO:1 provides two fragments of about 123 base pairs, and 201 base pairs, whereas HaeIII digestion yields fragments of about 46 base pairs, and 278 base pairs.

Zven1 or Zven2 polypeptides can be used as an aid to teach preparation of antibodies; identifying proteins by western blotting; protein purification; determining the weight of expressed Zven1 or Zven2 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., protease inhibition) in vitro and in vivo. For example, students will find that digestion of unglycosylated Zven1 with cyanogen bromide yields four fragments having approximate molecular weights of 148, 4337, 1909, 2402, and 2939, whereas digestion of unglycosylated Zven1 with BNPS or NCS/urea yields fragments having approximate molecular weights of 5231, and 6444.

Zven1 or Zven2 polypeptides can also be used to teach analytical skills such as mass spectrometry, circular dichroism, to determine conformation, especially of the four alpha helices, x-ray crystallography to determine the three-dimensional structure in atomic detail, nuclear magnetic resonance spectroscopy to reveal the structure of proteins in solution. For example, a kit containing Zven1 or Zven2 can be given to the student to analyze. Since the amino acid sequence would be known by the instructor, the protein can be given to the student as a test to determine the skills or develop the skills of the student, the instructor would then know whether or not the student has correctly analyzed the polypeptide. Since every polypeptide is unique, the educational utility of Zven1 or Zven2 would be unique unto itself.

The antibodies which bind specifically to Zven1 or Zven2 can be used as a teaching aid to instruct students how to prepare affinity chromatography columns to purify Zven1 or Zven2, cloning and sequencing the polynucleotide that encodes an antibody and thus as a practicum for teaching a student how to design humanized antibodies. The Zven1 or Zven2 gene, polypeptide, or antibody would then be packaged by reagent companies and sold to educational institutions so that the students gain skill in art of molecular biology. Because each gene and protein is unique, each gene and protein creates unique challenges and learning experiences for students in a lab practicum. Such educational kits containing the Zven1 or Zven2 gene, polypeptide, or antibody are considered within the scope of the present invention.

For any Zven polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Zven1 or Zven2 variants based upon the nucleotide and amino acid sequences described herein. Accordingly, the present invention includes a computer-readable medium encoded with a data structure that provides at least one of the following sequences: SEQ ID NO:1, SEQ ID NO:2, SEQ ID NO:3, SEQ ID NO:4, SEQ ID NO:5, and SEQ ID NO:6. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

5. Production of Zven Fusion Proteins

Fusion proteins of Zven can be used to express a Zven polypeptide or peptide in a recombinant host, and to isolate expressed Zven polypeptides and peptides. One type of fusion protein comprises a peptide that guides a Zven polypeptide from a recombinant host cell. To direct a Zven polypeptide into the secretory pathway of a eukaryotic host cell, a secretory signal sequence (also known as a signal peptide, a leader sequence, prepro sequence or pre sequence) is provided in the Zven expression vector. While the secretory signal sequence may be derived from Zven1 or Zven2, a suitable signal sequence may also be derived from another secreted protein or synthesized de novo. The secretory signal sequence is operably linked to a Zven1- or Zven2-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of Zven1, Zven2, or another protein produced by mammalian cells (e.g., tissue-type plasminogen activator signal sequence, as described, for example, in U.S. Pat. No. 5,641,655) is useful for expression of Zven1 or Zven2 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, $2^{nd}$ Edition, Glover and Hames (eds.), pages 123-167 (Oxford University Press 1995).

In bacterial cells, it is often desirable to express a heterologous protein as a fusion protein to decrease toxicity, increase stability, and to enhance recovery of the expressed protein. For example, Zven1 or Zven2 can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a Zven1 or Zven2 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

Another form of fusion protein comprises a Zven1 or Zven2 polypeptide and an immunoglobulin heavy chain constant region, typically an $F_c$ fragment, which contains two constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:7). In this fusion protein, a preferred Fc moiety is a human γ4 chain, which is stable in solution and has little or no complement activating activity. Accordingly, the present invention contemplates a Zven fusion protein that comprises a Zven1 or Zven2 polypeptide moiety and a human Fc fragment, wherein the C-terminus of the Zven polypeptide moiety is attached to the N-terminus of the Fc fragment via a peptide linker, such as a peptide consisting of the amino acid sequence of SEQ ID NO:7.

In another variation, a Zven1 or Zven2 fusion protein comprises an IgG sequence, a Zven polypeptide moiety covalently joined to the amino terminal end of the IgG sequence, and a signal peptide that is covalently joined to the amino terminal of the Zven polypeptide moiety, wherein the IgG sequence consists of the following elements in the following order: a hinge region, a $CH_2$ domain, and a $CH_3$ domain. Accordingly, the IgG sequence lacks a $CH_1$ domain. The Zven polypeptide moiety displays a Zven1 or Zven2 activity, such as the ability to bind with a Zven1 or Zven2 receptor. This general approach to producing fusion proteins that comprise both antibody and nonantibody portions has been described by LaRochelle et al., EP 742830 (WO 95/21258).

Fusion proteins comprising a Zven1 or Zven2 polypeptide moiety and an Fc moiety can be used, for example, as an in vitro assay tool. For example, the presence of a Zven1 or Zven2 receptor in a biological sample can be detected using these Zven1 or Zven2-antibody fusion proteins, in which the Zven moiety is used to target the cognate receptor, and a macromolecule, such as Protein A or anti-Fc antibody, is used to detect the bound fusion protein-ligand complex. In addition, antibody-Zven fusion proteins, comprising antibody variable domains, are useful as therapeutic proteins, in which the antibody moiety binds with a target antigen, such as a tumor associated antigen.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

6. Production of Zven Polypeptides

The polypeptides of the present invention, including full-length polypeptides, functional fragments, and fusion proteins, can be produced in recombinant host cells following conventional techniques. To express a Zven1 or Zven2 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene, which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a Zven1 expression vector may comprise a Zven1 gene and a secretory sequence derived from a Zven1 gene or another secreted gene.

Zven1 or Zven2 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CCL 8544, ATCC CRL 10314), canine kidney cells (MDCK; ATCC CCL 34), Chinese hamster ovary cells (CHO-K1; ATCC CCL61; CHO DG44 [Chasin et al., *Som. Cell. Molec. Genet.* 12:555 1986]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control Zven1 or Zven2 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Zven1 or Zven2 polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

Zven1 or Zven2 genes may also be expressed in other higher eukaryotic cells, such as avian, fungal, insect, yeast, or plant cells. The baculovirus system provides an efficient means to introduce cloned Zven1 or Zven2 genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Zven polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed Zven polypeptide, for example, a Glu-Glu epitope tag (Grussenmeyer et al., *Proc. Nat'l Acad. Sci.* 82:7952 (1985)). Using a technique known in the art, a transfer vector containing a Zven1 or Zven2 gene is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270: 1543 (1995). In such transfer vector constructs, a short or long version of the basic protein promoter can be used. Moreover, transfer vectors can be constructed which replace the native Zven1/Zven2 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native Zven1/Zven2 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume* 7: *Gene Transfer and Expression Protocols*, Murray (ed.), pages 147-168 (The Humana Press, Inc. 1991), by Patel et al., "The baculovirus expression system," in *DNA Cloning* 2: *Expression Systems, 2nd Edition,* Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae, Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615, 974, and Bitter, U.S. Pat. No. 4,977,092) and alcohol dehydrogenase genes. See also U.S. Pat. Nos. 4,990,446, 5,063, 154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenm* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is possible to use host cells in which both methanol utilization genes (AUG1 and AUG2) are deleted. For production of secreted proteins, host cells can be used that are deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67-88 (CRC Press, 1993).

Alternatively, Zven genes can be expressed in prokaryotic host cells. Suitable promoters that can be used to express Zven1 or Zven2 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli* , promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene, 4th Ed.* (Benjamin Cummins 1987), and by Ausubel et al. (1995).

Suitable prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing a Zven polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), Chapter 4, starting at page 101 (John Wiley & Sons, Inc. 1996), and Rudolph, "Successful Refolding on an Industrial Scale", Chapter 10).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NOs:2 and 5. Illustrative polypeptides of Zven2, for example, include 15 contiguous amino acid residues of amino acids 82 to 105 of SEQ ID NO:5. Exemplary polypeptides of Zven1 include 15 contiguous amino acid residues of amino acids 1 to 32 or amino acids 75 to 108 of SEQ ID NO:2, whereas exemplary Zven2 polypeptides include amino acids 82 to 105 of SEQ ID NO:5. Within certain embodiments of the invention, the polypeptides comprise 20, 30, 40, 50, 75, or more contiguous residues of SEQ ID NOs:2 or 5. Nucleic acid molecules encoding such peptides and polypeptides are useful as polymerase chain reaction primers and probes.

Examples for the production of Zven1 are shown in Examples 9, 10, 11, and 12.

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

7. Isolation of Zven Polypeptides

The polypeptides of the present invention can be purified to at least about 80% purity, to at least about 90% purity, to at least about 95% purity, or even greater than 95% purity with respect to contaminating macromolecules, particularly other proteins and nucleic acids, and free of infectious and pyrogenic agents. The polypeptides of the present invention can also be purified to a pharmaceutically pure state, which is greater than 99.9% pure. In certain preparations, a purified polypeptide is substantially free of other polypeptides, particularly other polypeptides of animal origin.

Fractionation and/or conventional purification methods can be used to obtain preparations of Zven1 or Zven2 purified from natural sources, and recombinant Zven polypeptides and fusion Zven polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in Zven isolation and purification can be devised by those of skill in the art. For example, anti-Zven antibodies, obtained as described below, can be used to isolate large quantities of protein by immunoaffinity purification. Moreover, methods for binding receptors to ligand polypeptides, such as Zven1 or Zven2, bound to support media are well known in the art.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification.

Zven polypeptides or fragments thereof may also be prepared through chemical synthesis, as described above. Zven polypeptides may be monomers or multimers; glycosylated or non-glycosylated; pegylated or non-pegylated; and may or may not include an initial methionine amino acid residue.

8. Zven Analogs

As described above, the disclosed polypeptides can be used to construct Zven variants. These polypeptides can be used to identify Zven1 or Zven2 analogs. One type of Zven analog mimics Zven by binding with a Zven receptor. Such an analog is considered to be a Zven agonist if the binding of the analog with a Zven receptor stimulates a response by a cell that expresses the receptor. On the other hand, a Zven analog that binds with a Zven receptor, but does not stimulate a cellular response, may be a Zven antagonist. Such an antagonist may diminish Zven or Zven agonist activity, for example, by a competitive or non-competitive binding of the antagonist to the Zven receptor.

One general class of Zven analogs are agonists or antagonists having an amino acid sequence that has at least one mutation, deletion (amino- or carboxyl-terminus), or substitution of the amino acid sequences disclosed herein. Another general class of Zven analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype Zven antibodies mimic Zven, these domains can provide either Zven agonist or antagonist activity. As an illustration, Lim and Langer, *J. Interferon Res.* 13:295 (1993), describe anti-idiotypic interferon-α antibodies that have the properties of either interferon-α agonists or antagonists.

A third approach to identifying Zven1 or Zven2 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

The activity of a Zven polypeptide, agonist, or antagonist can be determined using a standard cell proliferation or differentiation assay. For example, assays measuring proliferation include such assays as chemosensitivity to neutral red dye, incorporation of radiolabeled nucleotides, incorporation of 5-bromo-2'-deoxyuridine in the DNA of proliferating cells, and use of tetrazolium salts (Mosmann, *J. Immunol. Methods* 65:55 (1983); Porstmann et al., *J. Immunol. Methods* 82:169 (1985); Alley et al., *Cancer Res.* 48:589 (1988); Cook et al., *Analytical Biochem.* 179:1 (1989); Marshall et al., *Growth Reg.* 5:69 (1995); Scudiero et al., *Cancer Res.* 48:4827 (1988); Cavanaugh et al., *Investigational New Drugs* 8:347 (1990)). Assays measuring differentiation include, for example, measuring cell-surface markers associated with stage-specific expression of a tissue, enzymatic activity, functional activity or morphological changes (Raes, *Adv. Anim. Cell Biol. Technol. Bioprocesses*, pages 161-171 (1989; Watt, *FASEB*, 5:281 (1991); Francis, *Differentiation* 57:63 (1994)). Assays can be used to measure other cellular responses, that include, chemotaxis, adhesion, changes in ion channel influx, regulation of second messenger levels and neurotransmitter release. Such assays are well known in the art (see, for example, Chayen and Bitensky, *Cytochemical Bioassays: Techniques & Applications* (Marcel Dekker 1983)).

The effect of a variant Zven polypeptide, such as Zven1, Zven2, as well as agonists, fragments, variants and/or chimeras thereof, can also be determined by observing contractility of tissues, including gastrointestinal tissues, with a tensiometer that measures contractility and relaxation in tissues (see, for example, Dainty et al., *J. Pharmacol.* 100:767 (1990); Rhee et al., *Neurotox.* 16:179 (1995); Anderson, *Endocrinol.* 114:364 (1984); Downing, and Sherwood, *Endocrinol.* 116: 1206 (1985)). For example, methods for measuring vasodilatation of aortic rings are well known in the art. As an illustration, aortic rings are removed from four-month old Sprague Dawley rats and placed in a buffer solution, such as modified Krebs solution (118.5 mM NaCl, 4.6 mM KCl, 1.2 mM $MgSO_4.7H_2O$, 1.2 mM $KH_2PO_4$, 2.5 mM $CaCl_2.2H_2O$, 24.8 mM $NaHCO_3$ and 10 mM glucose). One of skill in the art would recognize that this method can be used with other animals, such as rabbits, other rat strains, Guinea pigs, and the like. The rings are then attached to an isometric force transducer (Radnoti Inc., Monrovia, Calif.) and the data are recorded with a Ponemah physiology platform (Gould Instrument systems, Inc., Valley View, Ohio) and placed in an oxygenated (95% $O_2$, 5% $CO_2$) tissue bath containing the buffer solution. The tissues are adjusted to one gram resting tension and allowed to stabilize for about one hour before testing. The integrity of the rings can be tested with norepinepherin (Sigma Co.; St. Louis, Mo.) and carbachol, a muscarinic acetylcholine agonist (Sigma Co.). After integrity is checked, the rings are washed three times with fresh buffer and allowed to rest for about one hour. To test a sample for vasodilatation, or relaxation of the aortic ring tissue, the rings are contracted to two grams tension and allowed to stabilize for fifteen minutes. A Zven polypeptide sample is then added to one, two, or three of the four baths, without flushing, and tension on the rings recorded and compared to the control rings containing buffer only. Enhancement or relaxation of contractility by Zven polypeptides, their agonists and antagonists is directly measured by this method, and it can be applied to other contractile tissues such as gastrointestinal tissues.

As another example, the effects of Zven1 were tested in a standard guinea pig ileum organ bath. The organ bath system is a standard method used to measure contractility in isolated tissue, and the guinea pig ileum is routinely used for recording contractile responses in the intestine ex vivo (Thomas E., et al., *Mol Pharmacol* 44:102-10, 1993). Because the components of the enteric nervous system are located entirely within the gut, it may be removed from the brain and the spinal cord and its reflex behaviors studied. The classical response observed in gastrointestinal tissue from guinea pig intestinal ileum is longitudinal contraction by smooth muscle fibers orientated along the long axis of the gut. As shown in Example 6, Zven1 treatment stimulated smooth muscle contraction in the ileum at picomolar concentrations as low as 0.75 ng/ml, which is equivalent to 75 pM. Additionally, the highest response was observed at the 20 ng/ml zven1 dose. Additional examples showing the effects of the Zven molecules of the present invention are shown in Examples 7, 14, and 15.

The effect of a variant Zven polypeptide, such as Zven1, Zven2, as well as agonists, fragments, variants and/or chimeras thereof, on gastric motility would typically be measured in the clinical setting as the time required for gastric emptying and subsequent transit time through the gastrointestinal tract. Gastric emptying scans are well known to those skilled in the art, and briefly, comprise use of an oral contrast agent, such as barium, or a radiolabeled meal. Solids and liquids can be measured independently. Generally, a test food or liquid is radiolabeled with an isotope (e.g., $^{99m}$Tc), and after ingestion or administration, transit time through the gastrointestinal tract and gastric emptying are measured by visualization using gamma cameras (Meyer et al., *Am. J. Dig. Dis.* 21:296 (1976); Collins et al., *Gut* 24:1117 (1983); Maughan et al., *Diabet. Med.* 13:S6 (1996), and Horowitz et al., *Arch. Intern. Med.* 145:1467 (1985)). The oral administration of phenol red (test meal) to measure gastric emptying and intestinal transit in rodents is a well-documented model (Martinez V, Cuttitta F, Tache Y 1997 Endocrinology 138:3749-3755). Briefly, animals are deprived of food for 18 hours but allowed free access to water. Animals receive oral administration of 0.15 ml of test meal, consisting of a 1.5% aqueous methylcellulose solution containing a non-absorbable dye, 0.05% phenol red (50 mg/100 ml Sigma Chemical Company Catalogue # P4758). The effects of Zven1 on gastric emptying in an in vivo mouse model are shown in Examples 4, 8, 21, and 22. Additional studies can be performed before and after the administration of a promotility agent to quantify the efficacy of the Zven polypeptide.

Radiolabeled or affinity labeled Zven polypeptides can also be used to identify or to localize Zven receptors in a biological sample (see, for example, Deutscher (ed.), *Methods in Enzymol.*, vol. 182, pages 721-37 (Academic Press 1990); Brunner et al., *Ann. Rev. Biochem.* 62:483 (1993); Fedan et al., *Biochem. Pharmacol.* 33:1167 (1984)). Also see, Varthakavi and Minocha, *J. Gen. Virol.* 77:1875 (1996), who describe the use of anti-idiotype antibodies for receptor identification.

9. Production of Antibodies to Zven Proteins

Antibodies to a Zven polypeptide can be obtained, for example, using the product of a Zven expression vector or Zven isolated from a natural source as an antigen. Particularly useful anti-Zven1 and anti-Zven2 antibodies "bind specifically" with Zven1 and Zven2, respectively. Antibodies are considered to be specifically binding if the antibodies exhibit at least one of the following two properties: (1) antibodies bind to Zven1 or Zven2 with a threshold level of binding activity, and (2) antibodies do not significantly cross-react with polypeptides related to Zven1 or Zven2.

With regard to the first characteristic, antibodies specifically bind if they bind to a Zven polypeptide, peptide or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect Zven, but not known polypeptides (e.g., known Wnt inhibitors) using a standard Western blot analysis. Particular anti-Zven1 antibodies bind Zven1, but not Zven2, while certain anti-Zven2 antibodies bind Zven2, but not Zven1.

Anti-Zven1 and anti-Zven2 antibodies can be produced using antigenic Zven1 or Zven2 epitope-bearing peptides and polypeptides. Antigenic epitope-bearing peptides and polypeptides of the present invention contain a sequence of at least four, or between 15 to about 30 amino acids contained within SEQ ID NOs:2 or 5. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with Zven1 or Zven2. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in Zven1 or Zven2 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549-586 (Plenum Press 1990), and Garnier-Robson, Garnier et al., *J. Mol. Biol.* 120: 97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that suitable antigenic peptides of Zven1 include the following segments of the amino acid sequence of SEQ ID NO:2: amino acids 22 to 27 ("antigenic peptide 1"), amino acids 33 to 41 ("antigenic peptide 2"), amino acids 61 to 68 ("antigenic peptide 3"), amino acids 80 to 85 ("antigenic peptide 4"), amino acids 97 to 102 ("antigenic peptide 5"), and amino acids 61 to 85 ("antigenic peptide 6"). The present invention contemplates the use of any one of antigenic peptides 1 to 6 to generate antibodies to Zven1. The present invention also contemplates polypeptides comprising at least one of antigenic peptides 1 to 6.

Similarly, analysis of the Zven2 amino acid sequence indicated that suitable antigenic peptides of Zven2 include the following segments of the amino acid sequence of SEQ ID NO:5: amino acids 25 to 33 ("antigenic peptide 7"), amino acids 53 to 66 ("antigenic peptide 8"), amino acids 88 to 95 ("antigenic peptide 9"), amino acids 98 to 103 ("antigenic peptide 10"), and amino acids 88 to 103 ("antigenic peptide 11"). The present invention contemplates the use of any one of antigenic peptides 7 to 11 to generate antibodies to Zven2. The present invention also contemplates polypeptides comprising at least one of antigenic peptides 7 to 11.

Polyclonal antibodies to recombinant Zven protein or to Zven isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995). The immunogenicity of a Zven polypeptide can be increased through the use of an adjuvant, such as alum (aluminum hydroxide) or Freund's complete or incomplete adjuvant. Polypeptides useful for immunization also include fusion polypeptides, such as fusions of Zven or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-Zven antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-Zven antibodies can be generated. Rodent mono-clonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1-2.6.7 (John Wiley & Sons 1991) ["Coligan"], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a Zven gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-Zven antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of anti-Zven antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology Vol.* 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains, which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli.* The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to Zven polypeptide in vitro, and selecting antibody display libraries in phage or similar vectors (for instance, through use of immobilized or labeled Zven protein or peptide). Genes encoding polypeptides having potential Zven polypeptide binding domains can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides, which interact with a known target that can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the Zven sequences disclosed herein to identify proteins which bind to Zven.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-Zven antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et a., U.S. Pat. No. 5,693,762 (1997).

Polyclonal anti-idiotype antibodies can be prepared by immunizing animals with anti-Zven antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-Zven antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

10. Therapeutic Uses of Zven Polypeptides and Antibodies

The present invention includes the use of anti-Zven molecules, including antagonists, antibodies, binding proteins, variants and fragments, having anti-Zven activity. The invention includes administering to a subject, the anti-Zven moleculeand contemplates both veterinary and human therapeutic uses. Illustrative subjects include mammalian subjects, such as farm animals, domestic animals, and human patients.

Anti-Zven molecules, antagonists, antibodies, binding proteins, variants and fragments, are useful in treating and detecting Inflammatory Bowel Disease (IBD) and Irritable Bowel Syndrome (IBS).

Inflammatory Bowel Disease (IBD) can affect the colon and/or rectum (Ulcerative colitis), or the small and large intestine (Crohn's Disease). The pathogenesis of these diseases is unclear, but they involve chronic inflammation of the affected tissues. Potential therapeutics include anti-Zven molecules, including, anti-Zven1 and anti-Zven2 antibodies, other binding proteins, variants, fragments, chimeras, and other Zven1 and Zven2 antagonists. These molecules could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form, releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress. Thus, the anti-Zven molecules of the present invention can be useful to treat and or detect UC.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanied by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. DSS is regarded as a T cell-independent model because it is observed in T cell-deficient animals such as SCID mice.

The administration of anti-Zven1 or znti-Zven2 antibodies or binding partners to these TNBS or DSS models can be used to ameliorate symptoms and alter the course of gastrointestinal disease. Zven1 and/or Zven2 may play a role in the inflammatory response in colitis, and the neutralization of Zven1 and/or Zven2 activity by administrating antagonists is a potential therapeutic approach for IBD.

Inflammatory reactions cause various clinical manifestations frequently associated with abnormal motility of the gastrointestinal tract, such as nausea, vomiting, ileus or diarrhea. Bacterial lipopolysaccharide (LPS) exposure, for example, induces such an inflammatory condition, which is observed in both humans and experimental animals, and is characterized by biphasic changes in gastrointestinal motility: increased transit in earlier phases and delayed transit in later phases. Since Zven1 plays a role in inflammation, and has biphasic activities at low (prokinetic) and high (inhibitory) doses, it will be beneficial in these inflammatory conditions.

Irritable Bowel Syndrome is one of the most common conditions in the gastrointestinal clinic. Yet, diagnosis and treatment for IBS remain limited. As the expression of Zven1 has been correlated with symptoms of IBS, anti-Zven molecules, including, anti-Zven1 and anti-Zven2 antibodies, other binding proteins, variants, fragments, chimeras, and other Zven1 and Zven2 antagonists are useful in reducing symptoms and treatment of the disease.

Additional characteristic of IBS are impaired gastrointestinal motility, with symptoms often alternating between bouts of diarrhea and constipation, and increased visceral sensitivity to intestinal smooth muscle contractions and distention. As Zven1 and Zven2 are molecules that regulate gastrointestinal contractiliy, gastric emptying and intestinal transit, Zven polypeptides, such as Zven1, Zven2, as well as agonists, fragments, variants and/or chimeras, of the present invention can be particularly useful in an overall treatment for IBS. The biphasic nature of Zven1, i.e., its ability to inhibit motility at high doses, and enhance motility at low doses, suggest that its expression is dys-regulated in IBS, with constipation prone patiens displaying elevated zven1 levels, and diarrhea prone patients displaying lower Zven1 levels.

The administration of anti-Zven1 or znti-Zven2 antibodies or binding partners to a patient with IBD or IBS can be used to ameliorate symptoms and alter the course of gastrointestinal disease. Zven1 and/or Zven2 may play a role in the inflammatory response in colitis, and the neutralization of Zven1 and/or Zven2 activity by administrating antagonists is a potential therapeutic approach for IBD and/or IBS.

Zven polypeptides, such as Zven1, Zven2, as well as agonists, fragments, variants and/or chimeras thereof, can be used to stimulate chemokine production. Chemokines are small pro-inflammatory proteins that have a broad range of activities involved in the recruitment and function of leukocytes. Rat CINC-1, murine KC, and human GROα are members of the CXC subfamily of chemokines. Chemokines, in general, can be divided into groups that are chemotactic predominatly for neutrophils, and also have angiogenic activity, and those that primarily attract T lymphocytes and monocytes. See Banks, C. et al, *J. Pathology* 199: 28-35, 2002. Chemokines in the first group display an ELR (Glu-Leu-Arg) amino acid motif at the $NH_2$ terminus. GROα, for example, contains this motif. GROα also has mitogenic and angiogenic properties and is involved in wound healing and blood vessel formation. (See, for example, Li and Thornhill, *Cytokine*

12:1409 (2000)). As illustrated by Examples 2, 3, and 11, Zven1 and Zven2 stimulated the release of chemokine CINC-1 (Cytokine Induced Neutrophil Chemoattractant factor 1) in cell lines derived from the thoracic aorta of rats, Zven1 stimulated the release of chemokine KC from mice, and chemokine MIP-2 (mouse Macrophage Inflammatory Protein-2) is up-regulated in response to a low dose (intraperitoneal injection) of Zven1. Therefore, Zven polypeptides, such as Zven1, Zven2, as well as agonists, fragments, variants and/or chimeras thereof, can be used to stimulate the production chemokines in vivo. The chemokines can be purified from culture media and used in research or clinical settings. Zven variants can also be identified by the ability to stimulate production of chemokines in vitro or in vivo.

Upregulated chemokine expression correlates with increasing activity of IBD. See Banks, C. et al, *J. Pathology* 199: 28-35, 2002. Chemokines are able to attract inflammatory cells and are involved in their activation. Similarly, MIP-2 expression has been found to be associated with neutrophil influx in various inflammatory conditions. As polypeptides that stimulate the production of chemokines, Zven polypeptides, such as Zven1, Zven2, as well as agonists, fragments, variants and/or chimeras thereof, may be useful in treating Inflammatory Bowel Disease by reducing, inhibiting or preventing chemokine influx in the intestinal tract.

As a protein that can stimulate the production of chemokines, Zven polypeptides, such as Zven1, Zven2, as well as agonists, fragments, variants and/or chimeras thereof, may be useful in treating infections, including fungal, bacterial, viral and parasitic infections. Thus, the administration of a Zven polypeptide, such as Zven1, Zven2, as well as an agonist, fragment, variant and/or a chimera thereof, may be used as an immune booster to a specific tissue site. For example, Zven1 administered to gastrointestinal tissue, or to lung tissue, may be useful alone, or in combination therapy to treat infections.

As shown in Example 3, Zven1 administration can cause neutrophil infiltration. There are many aspects involved in the immune response of a mammal to an injury or infection where neutrophil infiltration would be desirable. As such, Zven polypeptides, such as Zven1, Zven2, as well as agonists, fragments, variants and/or chimeras thereof, will be useful as an agent to induce neutrophil infiltration.

The additonal activity of Zven1 as a modulator of immunity and chemotaxis, inducing neutrophil infiltration, indicates that it may be involved in the early infectious insults that are often the initiator of IBS (Collins et al). By both increasing intestinal motility and inducing neutrophil influx to remove invading pathogens, Zven1 would serve to resolve a gastrointestinal infection such as food poisoning. In some IBS patients, this infectious event is never resolved, leading to a chronic inflammatory state and gastrointestinal motility problems, either constipation or diarhea, or alternating bouts of both. A Zven1 inhibitor could additionally reduce the inflammatory state, by reducing neutrophil numbers in affected inflamed gastrointestinal tissue.

Inflammatory reactions cause various clinical manifestations frequently associated with abnormal motility of the gastrointestinal tract, such as nausea, vomiting, ileus or diarrhea. Bacterial lipopolysaccharide (LPS) exposure, for example, induces such an inflammatory condition, which is observed in both humans and experimental animals, and is characterized by biphasic changes in gastrointestinal motility: increased transit in earlier phases and delayed transit in later phases. Since Zven1 plays a role in inflammation, and has biphasic activities at low (prokinetic) and high (inhibitory) doses, it will be beneficial in these inflammatory conditions.

For disorders related to IBS and IBD, clinical signs of improved function include, but are not limited to, reduction in pain, cramping and sensitivity, reduction in diarrhea and improved stool consistency, reduced abdominal distension, and increased intestinal transit. Improvement can also be measured by a decrease in mean Crohn's Disease Activity Index (CDAI). See Best. W. et al., *Gasttoenterology* 70: 439-44, 1976. Additonally, improved function can be measured by a quality of life assessment as described by Irvine et al. (Irvine, E. et al., *Gasttoenterology* 106: 287-96, 1994.

For disorders related to deficient gastrointestinal function, clinical signs of improved function include, but are not limited to, increased intestinal transit, increased gastric emptying, flatus, and borborygmi, ability to consume liquids and solids, and/or a reduction in nausea and/or emesis For disorders related to hyperactive gastrointestinal contractility, clinincal signs of improved gastrointestinal function include, but are not limited to, slowed gastric emptying, slowed intestinal transit, and/or a reduction in cramps associated with diarrhea.

Zven polypeptides, such as Zven1, Zven2, as well as agonists, fragments, variants and/or chimeras thereof, can also be used to treat gastrointestinal related sepsis. Experimental "sepsis"/endotoxemia is produced in rodents using methods described in Ceregrzyn et al. *Neurogastroenterol. Mot.* 13:605-613 (2001). These animals develop biphasic alterations in gastrointestinal transit. A Zven polypeptide, such as Zven1, Zven2, as well as agonists, fragments, variants and/or chimeras thereof, can be administered orally orally (p.o.), intraperitoneally (i.p.), intraveneously (i.v.), subcutaneously (s.c.), or intramuscularly (i.m.) at either low (prokinetic) or high (inhibitory) concentrations, depending on the phase of the disease. Gastric emptying and/or intestinal transit would then be measured using one of the Major Models described below.

11. Models of Inflammation, Gastric Emptying, and Intestinal Transition in the Bowel Animal Models of Inflammatory Bowel Disease (IBD) (See Wirtz and Neurath. *Int J. Colorectal Dis.* 15: 144-60 (2000)

Spontaneous models of IBD: IBD in humans is believed to occur in individuals with genetic predisposition after exposure to environmental factors. Spontaneous models may offer advantages over inducible models for defining genetic susceptibility factors.

Example of spontaneous model: C3H/HeJBir mice. This is a "research strain" from Jackson Labs that develops a spontaneous pathogen-independent colitis at about 3 wks of age with acute and chronic lesions and ulcerations mainly in the cecum and right side of the proximal colon mucosa. CD4+ T cells have been identified as important components in the pathogenesis. A test compound, such as Zven1 and/or Zven2 and/or variants or antagonists, could be administered to assess its affect on symptoms and lesions.

Inducible models of IBD involve the activation of the mucosal immune system by contact with luminal agents.

Inducible Example 1: Dextran Sodium Sulfate (DSS) (in Rodents)

Feeding mice or rats for several days with DSS polymers in the drinking water induces an acute colitis with bloody diarrhea, ulcerations, histological damage, and infiltration with neutrophils. In susceptible strains, DSS (cycled for 7 d with DSS, and then 7 d with water) results in chronic lesions with infiltrating macrophages, CD4+ T lymphocytes, and fissuring ulcers. Later phases are associated with increased levels of pro-inflammatory cytokines (i.e. IL-2, IL-4, IL-6) and leukotrienes, suggesting the involvement of he adaptive immune system. A test compound, such as Zven1 and/or Zven2 and/or variants or antagonists, could be administered to assess its affect on symptoms and lesions.

Inducible Example 2: Acetic Acid (in Rodents; Rabbits)

The intrarectal administration of diluted acetic acid into rodents or rabbits leads to epithelial injury and increased permeability followed by an acute mucosal/transmural inflammation. This is supposedly a reproducible model that is easy to use and valuable for studying early events of inflammation after mucosal injury and would healing. A test compound, such as Zven1 and/or Zven2 and/or variants or antagonists, could be administered to assess its affect on symptoms and lesions, as well as extent and rate of healing.

Animal models of irritable bowel syndrome (IBS). See Mayer and Collins. *Gastroenterol.* 122:2032-2048 (2002). These models can be divided into those that are mediated primarily by CNS-directed mechanisms ("Stress Memory" models) and those with primary gut-directed etiologies ("Pain Memory" and "Immune Memory" models).

Model of Pain Assessment Associated with Gut Distention (in Rats, Rabbits: Dogs)

Indication: IBD, IBS, Gastroparesis, Ileus, Dyspepsia.

Animals are surgically prepared with electrodes implanted on the proximal colon and striated muscles, and catheters implanted in lateral ventricles of the brain. Rectal distension is performed by inflation of a balloon rectally inserted, and the pressure eliciting a characteristic visceromotor response is measured. A test compound, such as Zven1 and/or Zven2 and/or variants or antagonists, is administered via the appropriate route (p.o., i.p., s.c., i.v., or i.m.) and at the appropriate time (i.e. ~20 min, if i.p. or i.c.v.) prior to distention. Test compound is evaluated for its ability to affect colonic motility, abdominal contractions, and visceral pain.

Additionally, disorders associated with inflammation of the intestine can be treated with the Zven1, Zven2, as variants, fragments, agonists and antagonists thereof described herein. For example, Irritable Bowel Syndrome (IBS) is characterized by a very broad spectrum of symptoms (pain; bouts of diarrhea and/or constipation; abnormal gastrointestinal motility). It is difficult to pinpoint the etiology, and may have components related to stress, genetics, and/or inflammation. Simiarly, the anti-Zven1, and anti-Zven2 molecules of the present invention, including antibodies and binding partners, can be used to treat Inflammatory Bowel Disease, (including colitis and Crohn's disease). IBD is more serious than IBS, and is characterized by diarrhea, pain, and malnutrition. Patients with IBD often have increased risk of gastrointestinal cancer.

As described above, there are a number of in vivo models to measure gastric function. A few of these models are represented below.

Model 1: Method to Measure Rate and Extent of Gastric Emptying and Intestinal Transit Using Phenol Red/Methyl Cellulose in Experimental Mammals Fasted animals are given Zven1 (or other Zven agent, Zven polypeptides, such as Zven1, Zven2, as well as agonists, fragments, variants and/or chimeras thereof) by the appropriate route (p.o., i.p., i.v., s.c., i.m.). At the appropriate time point, a non-nutritive semi-solid meal consisting of methylcellulose and phenol red is administered by gavage, and animals are sacrificed at a set time following this meal administration. Transit is assessed by the recovery and spectrophotometric determination of phenol red from designated regions along the gastrointestinal tract. The period of dye recovery in the gastrointestinal tract may be from 10 to 180 minutes, depending on the indication and intestinal site of interest. This model has been used extensively to evaluate the efficacy of other prokinetic drugs on gastric emptying and/or intestinal transit.

Model 2: Method to Measure Rate and Extent of Intestinal Transit Using Arabic Gum/Charcoal Meal in Experimental Mammals Fasted animals would be given Zven1 (or other Zven agent, Zven polypeptides, such as Zven1, Zven2, as well as agonists, fragments, variants and/or chimeras thereof) by the appropriate route (i.p., i.v., s.c., i.m., p.o.). At the appropriate time point, a semi-solid meal consisting of gum arabic and charcoal is administered by gavage, and animals are sacrificed at a set time following this meal administration (Puig and Pol. *J. Pharmacol. Experiment. Therap.* 287:1068 (1998)). Transit is assessed by the distance that the charcoal meal traveled as a fraction of the total distance of the intestine. The period of transit measurement in the gastrointestinal tract may be from 10 to 180 minutes, depending on the indication and intestinal site of interest. This model has been used extensively to evaluate the efficacy of prokinetic drugs on intestinal transit.

Model 3: Method to Measure Rate and Extent of Gastric Emptying Using Polystyrene Beads (Undigestible Solids) in Experimental Rodents Gastric emptying is evaluated by determining the emptying of polystyrene beads of a specific diameter (e.g. 1 mm for rats) from the stomach of fasted (24 h) male or female experimental rodents in response to Zven1 (or another Zven agent, Zven polypeptides, such as Zven1, Zven2, as well as agonists, fragments, variants and/or chimeras thereof) via p.o., i.p., s.c., i.v. or i.m. route of administration. Polystyrene beads are administered by gavage and assessed for emptying as previously described (Takeuchi et al. *Digest. Dis. Sci.* 42;251-258 (1997)). Animals are sacrificed at a specified time after pellet administration (e.g. 20-180 min), and the stomachs are removed. The number of the pellets remaining in the stomach are counted. In control studies, 90% of pellets would be expected to remain in the stomach after 30 min, and fewer than 10% in the stomach after 3 h. This model has been used extensively to evaluate the gastric emptying efficacy of prokinetic drugs in experimental rodents.

Model 4: Method to Measure Rate and Extent of Gastric Emptying of a Liquid or Solid Test Meal in Experimental Mammals Using Acetaminophen as the Tracer Fasted animals are given a liquid or solid test meal containing acetominophen as the tracer. The test compound (e.g. Zven1) is administered p.o., i.v., i.p., s.c., or i.m. either before or after test meal administration. Blood samples are obtained at intervals between 0 and 120 min, and the plasma concentration of acetaminophen (which is a measure of gastric emptying) is measured by HPLC. This is described, for example, in Trudel et al *Peptides* 24:531-534 (2003).

Model 5: Method to Measure Gastric Emptying of a Solid Meal in Experimental Rodents Mice or rats ("rodents") are separated into four groups (Zven1-; positive control-[erythromycin, metoclopramide, or cisapride]; negative control-[caerulein]; and vehicle-treated groups). Each group contains approximately 10 animals. They are deprived of food for 24 hours, but have free access to water during fast period. Animals are housed one per cage, with floor grids placed in the cages to prevent contact with the bedding or feces. The fasted animals are treated with one of the above agents via one of the following routes of administrations: oral; i.p., i.v., s.c., or i.m.). Animals are introduced to pre-weighed Purina chow individually for a set period of time (e.g. 1 hr) in their home cages (with bedding removed) at the appropriate time point following or prior to administration of test agent. At the end of the feeding period, animals are housed in their home cages without food and water for an additional set period of time. They are then euthanized, the abdominal cavity opened, and stomach removed after clamping the pylorus and cardia. The stomach is weighed, opened, and washed of the gastric content by tap water. The gastric wall is wiped dry, and the empty stomach is weighed again. Gastric contents are collected, dried, and weighed. The amount of food contained in the stomach (as measured in grams) is calculated as the difference between the total weight of the stomach with content and the weight of the stomach wall after the contents are removed. The weight of the pellet and spill in the cage is also measured at the end of the feeding period. The solid food ingested by the animals is determined by the difference between the weight of the Purina chow before feeding and the weight of the pellet and spill at the end of the feeding period. The gastric emptying for the designated period is calculated according to the equation: % of gastric emptying=(1−gastric content/food intake)×100. This model has been used extensively in the literature to assess gastric emptying of a solid meal (Martinez et al. *J. Pharmacol. Experiment. Ther.* 301: 611-617 (2002)).

Model 6: Method to Measure Rate and Extent of Gastric Emptying of a Solid Test Meal in Experimental Mammals Fasted animals receive barium sulfate spheroids with a standard meal, followed by administration of the test compound such as Zven polypeptides, such as Zven1, Zven2, as well as agonists, fragments, variants and/or chimeras thereof (via p.o., i.v., i.p., s.c., or i.m) either before or after the meal. Gastric emptying is measured by means of X-ray location, with passage being monitored at least every 15min-2 h. This method is described, for example, in Takeda et al. *Jpn. J. Pharmacol.* 81:292-297 (1999).

Model 7: Method to Measure Colonic Propulsive Motility in Experimental Rodents.

This is used to demonstrate and characterize the pharmacological effects of compounds on colonic propulsive motility in experimental rodents as described (Martinez et a. *J. Pharmacol. Experiment. Ther.* 301: 611-617 (2002)). The test is based on the reflex expulsion of a glass bead from the distal colon, which is indicative of drug effects on the reflex arc. This test is useful in evaluating whether diarrhea is a side effect. Mice or rats are fasted for one hour prior to administrations of the test compound, such Zven polypeptides, such as Zven1, Zven2, as well as agonists, fragments, variants and/or chimeras thereof, or vehicle by the appropriate route (i.p., s.c., i.m., p.o., i.v.), followed 30 minutes (or other appropriate time) later by the insertion of a glass bead into the distal colon. Rodents are marked for identification and placed in large glass beakers (or other) for observation. The time required for expulsion of the bead is noted for each rodent.

Model 8: Model to Measure Gastrointestinal Motor Activity in Dogs.

Dogs are anesthetized and the abdominal cavity opened. Extraluminal force transducers (sensor to measure contraction) are sutured onto five (5) sites, i.e., the gastric antrum, 3 cm proximal to the pyloric ring, the duodenum, 5 cm distal to the pyloric ring, the jejunum, 70 cm distal to the pyloric ring, the ileum, 5 cm proximal to the ileum-colon junction, and the colon, 5 cm distal to the ileum-colon junction. The lead wires of these force transducers are taken out of the abdominal cavity and then brought out through a skin incision made between the scapulae, at which a connector is connected. After the operation, a jacket protector is placed on the dog to protect the connector. Measurement of the gastrointestinal motor activity is started two weeks after the operation. For ad libitum measurement, a telemeter (electrowave data transmitter) is connected with the connector to determine the contractive motility at each site of the gastrointestinal tract. The data is stored in a computer via a telemeter for analysis. A test compound, such as Zven polypeptides, such as Zven1, Zven2, as well as agonists, fragments, variants and/or chimeras thereof, is administered via the appropriate route (p.o., i.v., i.p., s.c., i.m.) at the appropriate time point to assess its ability to affect gastrointestinal motor activity. This can be performed in normal dogs or dogs in which gastroparesis/ileus has been induced. The above method is a modification of those in Yoshida. and Ito. *J. Pharmacol. Experiment. Therap.* 257, 781-787 (1991) and Furuta et al. *Biol. Pharm. Bull.* 25:103-1071 (2002).

Model to Assess Emesis (in Ferrets).

Indication: Emesis (Primary or as a Result of Gastroparesis)

The anti-emetic activity of a test compound is tested by its ability to inhibit cisplatin- or syrup of ipecac-induced emesis in the ferret (since mice and rats can not vomit). In this model the onset of retching and vomiting occurs approximately 1 h after the administration of cisplatin (200 mg/m.sup.2 i.p.). At the first retch in response to cisplatin, the test compound, Zven polypeptides, such as Zven1, Zven2, as well as agonists, fragments, variants and/or chimeras thereof, is administered (e.g. i.p., p.o., i.v., s.c., i.c.v.) and its effect on emesis determined by comparison with appropriate controls (e.g. water). If using ipecac to induce emesis, the test compound may be given at appropriate time points prior to the ipecac. Latency to the first retch, the first vomit and the number of retching and vomiting episodes are recorded over 60 min. Data are expressed as the mean latency (in min) to first retch or vomit; the mean number of emetic episodes per ferret based on animals that did not exhibit emesis as well as those that did, and the mean number of retches/vomits exhibited by animals that remained responsive to ipecac ("responders"). Ferrets that fail to exhibit emesis are omitted from the latter calculation. [i.e. (.+−.) cis-3-(2-methoxybenzylamino)-2-phenyl piperidine exhibited anti-emetic activity when administered at a dose of 3 mg/kg i.p.]

High chemokine levels and neutrophil infiltrates are characteristics of local acute inflammation. Epithelial cell damage and infiltration by neutrophils is especially prominent in the local inflammatory process of ulcerative colitis. Zven1 antagonists or Zven2 antagonists, therefore, can be used as anti-inflammatory agents. As an illustration, a Zven1 antagonist can be used as an anti-inflammatory agent to treat inflammatory bowel diseases associated with increased neutrophil infiltration, or chemokine expression (e.g., Crohn's disease, ulcerative colitis, and irritable bowel syndrome). A Zven1 antagonist can also be used to treat inflammation of the brain (e.g., associated with encephalomyelitis, multiple sclerosis, and the like). An illustrative Zven1 antagonist is an antibody or antibody fragment that binds with a polypeptide having the amino acid sequence of amino acid residues 23 to 108 of SEQ ID NO:2, with a polypeptide having the amino acid sequence of amino acid residues 28 to 108 of SEQ ID NO:2, or with a polypeptide having the amino acid sequence of amino acid residues 20 to 105 of SEQ ID NO:5.

Neuropathy and sensory deficiency involve pain and loss of sensitivity, and can be related to such diseases as, diabetes, multiple sclerosis, and hypertension, for example. As a protein that is expressed in the brain, antagonists of zven1 may be useful to treat pain and sensory deficiencies. For example, zven1 antagonists can be delivered topically, centrally, or systemically, to treat diabetic neuropathy.

Zven1 polypeptides, and other Zven1 agonists, can be used to enhance the immune function in, for example, patients with various forms of cancer, HIV infection, or an immune disorder, such as chronic granulomatous disease or Chedick Higashi Syndrome. Zven1 polypeptides, and other Zven1 agonists, can also be used to alleviate pain, such as visceral pain or severe headache (e.g., migraine).

As shown in Example 5, Zven1 and Zven2 can stimulate angiogenesis. Accordingly, Zven1, Zven2, Zven1 agonists, and Zven2 agonists can be used to induce growth of new blood vessels. These molecules can be administered to a mammalian subject alone or in combination with other angiogenic factors, such as vascular endothelial growth factor.

Zven polypeptides, such as Zven1, Zven2, as well as agonists, fragments, variants and/or chimeras thereof, can also be used to increase sensitization in mammals. For example, an ortholog of Zven1 and Zven2, Bv8, was used to stimulate the PK-R1 and PK-R2 receptors in rats resulting in sensitization of peripheral nociceptors to thermal and mechanic stimuli. See Negri, L. et al., *Brit. J. Pharm.* 137: 1147-1154, 2002. Thus, the Zven1 and Zven2 polypeptides of the present invention, including agonists, can be used to increase sensitization (pain, heat, or mechanical) when delivered locally or topically, systemically, or centrally. Also, the polypeptides of the present invention can be administered to enhance the sensitivity of brain cells in order to improve the function out of the surviving neurons to neurotransmitters and therefore might be effective in Parkinson's or Alzheimers disease. Zven1 polypeptides, and other Zven1 agonists, can also be used to alleviate pain, such as visceral pain or severe headache (e.g., migraine).

Similarly, where a patient has an increased sensitization to pain, antagonists to Zven1 and Zven2 can be used to decrease the sensation of pain in a patient with neuropathy. For example a patients with diabetic neuropathy have chronic, enhanced pain, the antagonist to zven1 may be useful to limit, prevent or decrease the pain.

Using telemetry in conscious male Sprague-Dawley rats, there were no significant changes in blood pressure or heart rate in response to an i.v. dose of 200 ug/kg Zven1. Stool consistency from these rats did not appear to be different during the 24 h period following Zven1 administration. Rats do not appear to be affected by these doses of Zven1. There were no reported outward affects when mice were administered 10,000 ug/kg Zven1 via an i.p. injection.

The Zven polypeptides of the present invention, such as Zven1, Zven2, as well as agonists, fragments, variants and/or chimeras thereof, can also be used as a supplement to food. Zven2 polypeptides have been purified from bovine milk. See Masuda Y. et al., *Bioc. and Biophys. Res. Comm.* 293:396-402, 2002. Additionally, increased gastrointestinal contractility can be conducive to improved metabolism and weight gain. As a protein that can be administered orally, Zven1 or Zven2, or a combination of agonists, variants, and/or fragments, can be useful as a supplement or adjuvant to a feeding program wherein the mammalian subject suffers from a lack of appetite and/or weight gain. Such conditions are known, for example, as failure to thrive, cachexia, and wasting syndromes. The polypeptides of the present invention may also be useful adapting an infant mammal to digesting more conventional types of food.

Generally, the dosage of administered polypeptide, protein or peptide will vary depending upon such factors as the patient's age, weight, height, sex, general medical condition and previous medical history. Typically, it is desirable to provide the recipient with a dosage of a molecule having anti-Zven activity, which is in the range of from about 1 pg/kg to 10 mg/kg (amount of agent/body weight of patient), although a lower or higher dosage also may be administered as circumstances dictate.

Zven1 polypeptides that were heated to 56 degrees C. for 30 minutes maintained some activity, when measured by a reporter assay. See Example 10. Thus, the polypeptides of the present invention may be effectively delivered orally.

Administration of a molecule having Zven activity to a subject can be intravenous, intraarterial, intraperitoneal, intramuscular, subcutaneous, intrapleural, intrathecal, by perfusion through a regional catheter, inhalation, as a suppository, or by direct intralesional injection. When administering therapeutic proteins by injection, the administration may be by continuous infusion or by single or multiple boluses. Alternatively, Zven polypeptides, such as Zven1, Zven2, as well as agonists, fragments, variants and/or chimeras thereof, can be administered as a controlled release formulation.

Additional routes of administration include oral, dermal, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising such as Zven1, Zven2, as well as agonists, fragments, variants and/or chimeras thereof, can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer such as Zven1, Zven2, as well as agonists, fragments, variants and/or chimeras thereof, (Potts et al., *Pharm. Biotechnol.* 10:213 (1997)).

Zven proteins can also be applied topically as, for example, liposomal preparations, gels, salves, as a component of a glue, prosthesis, or bandage, and the like.

Since chemokines can promote and accelerate tissue repair, such as Zven1, Zven2, as well as agonists, fragments, variants and/or chimeras thereof, can have a beneficial role in resolving disease. For example, topical administration is useful for wound healing applications, including the prevention of excess scaring and granulation tissue, prevention of keyloids, and prevention of adhesions following surgery.

A pharmaceutical composition comprising molecules having Zven1 or Zven2 activity can be furnished in liquid form, in an aerosol, or in solid form. Proteins having Zven1 or Zven2 activity can be administered as a conjugate with a pharmaceutically acceptable water-soluble polymer moiety. As an illustration, a Zven1-polyethylene glycol conjugate is useful to increase the circulating half-life of the interferon, and to reduce the immunogenicity of the polypeptide. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, Pharmaceutical Dosage Forms and Drug Delivery Systems, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

A pharmaceutical composition comprising a protein, polypeptide, or peptide having Zven1 or Zven2 activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, molecules having anti-Zven1 or anti-Zven2 activity and a pharmaceutically acceptable carrier are administered to a patient in a therapeutically effective amount. A combination of a protein, polypeptide, or peptide having Zven activity and a pharmaceutically acceptable carrier is said to be administered in a "therapeutically effective amount" if the amount administered is physiologically significant. An agent is physiologically significant if its presence results in a detectable change in the physiology of a recipient patient.

For example, the present invention includes methods of increasing or decreasing gastrointestinal symptoms related to IBD and IBS, such as inflammation, contractility, gastric emptying, and/or intestinal transt, comprising the step of administering a composition comprising an anti-Zven, such as antagonists, antibodies, binding proteins, variants and fragments polypeptide, to the patient. In an in vivo approach, the composition is a pharmaceutical composition, administered in a therapeutically effective amount to a mammalian subject.

A pharmaceutical composition comprising molecules having anti-Zven activity can be furnished in liquid form, or in solid form. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

Zven1 or Zven2 pharmaceutical compositions may be supplied as a kit comprising a container that comprises Zven1 or Zven2, a Zven1 or Zven2 agonist, or a Zven1 or Zven2 antagonist (e.g., an anti-Zven1 or Zven2 antibody or antibody fragment). For example, Zven1 or Zven2 can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the Zven1 or Zven2 composition is contraindicated in patients with known hypersensitivity to Zven1 or Zven2.

12. Therapeutic Uses of Zven Nucleotide Sequences

The present invention includes the use of Zven nucleotide sequences to provide Zven amino acid sequences to a subject in need of proteins, polypeptides, or peptides having Zven activity, as discussed in the previous section. In addition, a therapeutic expression vector can be provided that inhibits Zven gene expression, such as an anti-sense molecule, a ribozyme, or an external guide sequence molecule.

There are numerous approaches to introduce a Zven gene to a subject, including the use of recombinant host cells that express Zven, delivery of naked nucleic acid encoding Zven, use of a cationic lipid carrier with a nucleic acid molecule that encodes Zven, and the use of viruses that express Zven, such as recombinant retroviruses, recombinant adeno-associated viruses, recombinant adenoviruses, and recombinant Herpes simplex viruses [HSV] (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses a Zven gene, and then transplanted into the subject.

In order to effect expression of a Zven gene, an expression vector is constructed in which a nucleotide sequence encoding a Zven gene is operably linked to a core promoter, and optionally a regulatory element, to control gene transcription. The general requirements of an expression vector are described above.

Alternatively, a Zven gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399, 346). Within various embodiments, either the viral vector itself, or a viral particle which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant HSV can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

Alternatively, an expression vector comprising a Zven gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration of Zven nucleic acid molecules. For example, Aihara and Miyazaki, *Nature Biotechnology* 16:867 (1998), have demonstrated the use of in vivo electroporation for gene transfer into muscle.

In an alternative approach to gene therapy, a therapeutic gene may encode a Zven anti-sense RNA that inhibits the expression of Zven. Suitable sequences for Zven anti-sense molecules can be derived from the nucleotide sequences of Zven disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with Zven mRNA.

In another approach, expression vectors can be constructed in which a regulatory element directs the production of RNA transcripts capable of promoting RNase P-mediated cleavage of mRNA molecules that encode a Zven gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., *Science* 263:1269 (1994), Pace et al., international publication No. WO 96/18733, George et al., international publication No. WO 96/21731, and Werner et al., international publication No. WO 97/33991). Preferably, the external guide sequence comprises a ten to fifteen nucleotide sequence complementary to Zven mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a Zven nucleotide acid sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, *Remington's Pharmaceutical Sciences,* 19th Ed. (Mack Publishing Co. 1995), and *Gilman's the Pharmacological Basis of Therapeutics,* 7th Ed. (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

13. Detection of Zven Gene Expression with Nucleic Acid Probes

Nucleic acid molecules can be used to detect the expression of a Zven1 or Zven2 gene in a biological sample. Such probe molecules include double-stranded nucleic acid molecules comprising the nucleotide sequence of SEQ ID NO:1, or a fragment thereof, as well as single-stranded nucleic acid molecules having the complement of the nucleotide sequence of SEQ ID NO:1, or a fragment thereof. Probe molecules may be DNA, RNA, oligonucleotides, and the like.

Illustrative probes comprise a portion of the nucleotide sequence of nucleotides 66 to 161 of SEQ ID NO:1, the nucleotide sequence of nucleotides 288 to 389 of SEQ ID NO:1, or the complement of such nucleotide sequences. An additional example of a suitable probe is a probe consisting of nucleotides 354 to 382 of SEQ ID NO:1, or a portion thereof. As used herein, the term "portion" refers to at least eight nucleotides to at least 20 or more nucleotides.

For example, nucleic acid molecules comprising a portion of the nucleotide sequence of SEQ ID NO:1 or of SEQ ID NO:4, can be used to detect activated neutrophils. Such molecules can also be used to identity therapeutic or prophylactic agents that modulate the response of a neutrophil to a pathogen.

In a basic detection assay, a single-stranded probe molecule is incubated with RNA, isolated from a biological sample, under conditions of temperature and ionic strength that promote base pairing between the probe and target Zven1 RNA species. After separating unbound probe from hybridized molecules, the amount of hybrids is detected.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in *Methods in Gene Biotechnology*, pages 225-239 (CRC Press, Inc. 1997)). Nucleic acid probes can be detectably labeled with radioisotopes such as $^{32}$P or $^{35}$S. Alternatively, Zven RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Zven1 oligonucleotide probes are also useful for in vivo diagnosis. As an illustration, $^{18}$F-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

One variation of PCR for diagnostic assays is reverse transcriptase-PCR (RT-PCR). In the RT-PCR technique, RNA is isolated from a biological sample, reverse transcribed to cDNA, and the cDNA is incubated with Zven1 primers (see, for example, Wu et al. (eds.), "Rapid Isolation of Specific cDNAs or Genes by PCR," in *Methods in Gene Biotechnology*, pages 15-28 (CRC Press, Inc. 1997)). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Zven1 anti-sense oligomers. Oligo-dT primers offer the advantage that various mRNA nucleotide sequences are amplified that can provide control target sequences. Zven1 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Zven1 probe, and examined by autoradiography. Additional alternative approaches include the use of digoxigenin-labeled deoxyribonucleic acid triphosphates to provide chemiluminescence detection, and the C-TRAK calorimetric assay.

Another approach for detection of Zven expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniqes* 20:240 (1996)). Alternative methods for detection of Zven1 sequences can utilize approaches such as nucleic acid sequence-based amplification (NASBA), cooperative amplification of templates by cross-hybridization (CATCH), and the ligase chain reaction (LCR) (see, for example, Marshall et al, U.S. Pat. No. 5,686,272 (1997), Dyer et al., *J. Virol. Methods* 60:161 (1996), Ehricht et al., *Eur. J. Biochem.* 243:358 (1997), and Chadwick et al., *J. Virol. Methods* 70:59 (1998)). Other standard methods are known to those of skill in the art.

Zven1 probes and primers can also be used to detect and to localize Zven1 gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259-278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279-289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

Example 14, below, shows a method that can be used to detect and monitor IBD in patient samples. As discussed above, biological samples, including biopsy specimens can be screened for the presence of the polynucleotide sequences of SEQ ID NO:1 or SEQ ID NO:4, or a fragment thereof, to determine if Zven1 or Zven2 is upregulated in the sample.

14. Detection of Zven1 Protein with Anti-Zven 1 Antibodies

The present invention contemplates the use of anti-Zven1 antibodies to screen biological samples in vitro for the presence of Zven1, and particularly for the upregulation of Zven1. In one type of in vitro assay, anti-Zven1 antibodies are used in liquid phase. For example, the presence of Zven1 in a biological sample can be tested by mixing the biological sample with a trace amount of labeled Zven1 and an anti-Zven1 antibody under conditions that promote binding between Zven1 and its antibody. Complexes of Zven1 and anti-Zven1 in the sample can be separated from the reaction mixture by contacting the complex with an immobilized protein which binds with the antibody, such as an Fc antibody or *Staphylococcus* protein A. The concentration of Zven1 in the biological sample will be inversely proportional to the amount of labeled Zven1 bound to the antibody and directly related to the amount of free-labeled Zven1. Anti-Zven2 antibodies can be used in the same or a similar fashion.

Alternatively, in vitro assays can be performed in which anti-Zven1 antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-Zven1 antibodies can be used to detect Zven1 in tissue sections prepared from a biopsy specimen. Such immunochemical detection can be used to determine the relative abundance of Zven1 and to determine the distribution of Zven1 in the examined tissue. General immunochemistry techniques are well established (see, for example, Ponder, "Cell Marking Techniques and Their Application," in *Mammalian Development: A Practical Approach*, Monk (ed.), pages 115-38 (IRL Press 1987), Coligan at pages 5.8.1-5.8.8, Ausubel (1995) at pages 14.6.1 to 14.6.13 (Wiley Interscience 1990), and Manson (ed.), *Methods In Molecular Biology, Vol.* 10: *Immunochemical Protocols* (The Humana Press, Inc. 1992)).

Immunochemical detection can be performed by contacting a biological sample with an anti-Zven1 antibody, and then contacting the biological sample with a detectably labeled molecule that binds to the antibody. For example, the detectably labeled molecule can comprise an antibody moiety that binds to anti-Zven1 antibody. Alternatively, the anti-Zven1 antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-Zven1 antibody can be conjugated with a detectable label to form an anti-Zven1 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-Zven1 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Zven1 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Zven1 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Zven1 immunoconjugates can be detectably labeled by linking an anti-Zven1 antibody component to an enzyme. When the anti-Zven1-enzyme conjugate is incubated in the presence of the appropriate substrate, the enzyme moiety reacts with the substrate to produce a chemical moiety, which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels, which can be employed in accordance with the present invention. The binding of marker moieties to anti-Zven1 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990),Stein et al., *Cancer Res.* 50:1330 (1990),and Coligan, supra.

Moreover, the convenience and versatility of immunochemical detection can be enhanced by using anti-Zven1 antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Immunochemical Applications of Avidin-Biotin Technology," in *Methods In Molecular Biology, Vol.* 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

In a related approach, biotin- or FITC-labeled Zven1 can be used to identify cells that bind Zven1. Such can binding can be detected, for example, using flow cytometry.

The present invention also contemplates kits for performing an immunological diagnostic assay for Zven1 gene expression. Such kits comprise at least one container comprising an anti-Zven1 antibody, or antibody fragment. A kit may also comprise a second container comprising one or more reagents capable of indicating the presence of Zven1 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that Zven1 antibodies or antibody fragments are used to detect Zven1 protein. For example, written instructions may state that the enclosed antibody or antibody fragment can be used to detect Zven1. The written material can be applied directly to a container, or the written material can be provided in the form of a packaging insert.

Diagnosis of IBS to date has been limited to using criteria that correlate with symptoms. For example, the major criteria include the Manning criteria and the Rome criteria. See Farhadi, A. et al., *Expert Opin. Investig. Drugs* 10(7): 1211-1222, 2001. The Manning criteria consider: 1) pain that is improved after bowel movement; 2) looser stool at the onset of pain; 3) more frequent stool at the onset of pain; and 4) visible bowel distension. The Rome criteria consider: 1) relief upon defacation; 2) onset associated with change in frequency of stool; and 3) onset associated with change in form (appearance) of stool. An improved method of detecting and monitoring IBS can be the use of anti-Zven antibodies, including anti-Zven1 and anti-Zven2 antibodies to screen biological samples from patients with IBS. Example 15, below, shows a method that can be used to detect and monitor IBD in patient samples. As discussed above, biological samples, including biopsy specimens can be screened for the presence of the polypeptide sequences of SEQ ID NO:2 or SEQ ID NO:5, or a fragment thereof, to determine if Zven1 or Zven2 is upregulated in the sample. As such Zven polypeptides and nucleic acids of the present invention can be used as a diagnostic marker for Irritable Bowel Syndrome.

The present invention, thus generally described, will be understood more readily by reference to the following examples, which are provided by way of illustration and are not intended to be limiting of the present invention. The examples describe studies using Zven1 protein produced in baculovirus with a C-terminal Glu-Glu tag, following the methods generally described above. Zven2 ("endocrine-gland-derived vascular endothelial growth factor") protein was purchased from Peprotech, Inc. (Rocky Hill, N.J.).

15. Examples

Example 1

Stimulation of Responses in Wky12-22 Cells

Wky12-22 cells were derived from the medial layer of the thoracic aorta of Wistar-Kyoto rat pups, as described by Lemire et al., *American Journal of Pathology* 144:1068 (1994). These cells respond to both Zven1 and Zven2 in a reporter luciferase assay following transfection with NFkB/Ap-1 reporter construct. A control cell line, Wky3M-22, derived from the same tissue in adult rat did not signal. Activity was detected at concentrations ranging from 1-100 ng/ml of Zven1 or Zven2 (approximately 0.1 nM-10 nM). These data suggest that Wky12-22 cells carry the Zven1 receptor, and that Zven1 and Zven2 activate the NfKb/Ap-1 transcription factor.

In one experiment, Wky12-22 cells were loaded with the fluorescent dye Fura. The emission peak of Fura shifts when bound to calcium. Intracellular calcium release is detected by monitoring the wavelength shift. Zven1 induced intracellular calcium release at concentrations of 1-1000 ng/ml. Zven2 induced a similar response.

Extracellular signal-regulated kinase/mitogen-activated protein kinase (ERK-Map kinase) activity was measured in Wky12-22 cells in response to Zven1 treatment. Cells were incubated in Zven1 at concentrations ranging from 1 to 1,000 ng/ml for thirty minutes. Cells were fixed and stained for phosphorylated ERK-Map kinase using the Arrayscan, which measures the fluorescent intensities in the cytosol and the nucleus of the treated cell. The difference in fluorescence of the nucleus and the cytosol were quantified and plotted. Zven1 induced ERK-Map kinase activity with an $EC_{50}$ of 0.50 nM (approximately 5 ng/ml).

The binding of Zven1 to Wky12-22 cells was assessed using $I^{125}$-radiolabeled Zven1. Wky12-22 cells were seeded at low cell density and cultured for three to four days until they reached about 70% confluency. The cells were placed on ice, the medium was removed, and the monolayers were washed. The cells were incubated with increasing amounts of $I^{125}$-Zven1 in the absence (total binding) and presence (nonspecific binding) of a large excess of unlabeled Zven1. After various times at 4° C., the binding media were removed, the monolayers were washed, and the cells were solubilized with a small volume of 1.0 N NaOH. Cell associated radioactivity was determined in a gamma counter. The specific binding of $I^{125}$-Zven1 was calculated as the difference between the total and nonspecific values. The measured radioactivity was normalized to cell number that was determined on a set of parallel cultures. Nonlinear regression using a two-site model was used to fit the binding data for determination of Kd and Bmax. The high affinity site exhibited a Kd of 1.5 nM and a Bmax of 350 fmol bound/$10^6$ cells whereas the low affinity site showed a Kd of 31 nM with a Bmax of 1025 fmol bound/$10^6$ cells.

The results of these studies show that a neonatal rat aortic cell expresses the Zven1 receptor while equivalent adult rat cells do not. This suggests that Zven1 is involved with heart development and vasculogenesis. Zven1 signals through NFkB/Ap1 and induces chemokine release only in the neonatal cells, suggesting that it may trigger a mitogenic response in fetal or neonatal heart. Zven1 may be a required factor necessary for the induction of vasculogenesis/angiogenesis in cardiac stem cells. Zven1 induces intracellular calcium release in the Wky12-22 cell line, an effect consistent with chemokine activity. Consistent with its mitogenic activity, Zven1 activates a mitogen activated protein kinase.

Example 2

Zven1 and Zven2 Stimulate Chemokine Release In Vitro

Confluent Wky12-22 or Wky3M22 cells were incubated with varying concentrations of Zven1 for twenty-four hours. Conditioned media were collected and assayed for the chemokine CINC-1 using a commercially-available rat cytokine multiplex kit (Linco Research, Inc.; St. Charles, Mo.). CINC-1, thought to be equivalent to human growth-related oncogene-α (GRO-α), was detected at levels ranging from 1.8-5 ng/ml in cells treated with 0.1 to 100 ng/ml of Zven1 respectively. Zven2 induced an equivalent level of CINC-1 release from Wky12-22 cells. CINC-1 was not detected in either the control Wky3M-22 cell line derived from adult rat aorta, or non-treated controls.

Example 3

Zven1 Induces a Chemotactic Response and Stimulates Chemokine Release and Neutrophil Infiltration In Vivo Four groups of ten mice (BALB57/BL6 females at eight weeks of age) were either not treated, or injected with vehicle buffer control, 0.1 μg of Zven1 or 1 μg of Zven1 . Four hours later, peritoneal lavage fluid was collected, concentrated, and the cell pellets were resuspended. The relative cell populations were enumerated using the Cell Dyne, and cytospins were prepared for CBC/diff counts. The non-treated and buffer control animals had approximately 2% neutrophils in their lavage fluid, while the 0.1 µg treated animals had approximately 30% neutrophils, indicating an approximate 15-fold increase in neutrophils in the peritoneum of the Zven1-treated animals. The 1 µg Zven1-treated animals had neutrophil levels consistent with the non-treated controls, suggesting a bi-phasic Zven1 response. In sum, Zven1 induced neutrophil infiltration into the peritoneum following intraperitoneal injection.

Murine KC, the ortholog of GROα in mice, was measured in serum and lavage fluids obtained from the four groups of mice using an ELISA kit (R&D Systems Inc.; MN). The 0.1 µg Zven1-treated (low dose) mice had approximately 45 picograms/ml KC in their peritoneal fluid, which was significantly higher than the non-treated controls, the vehicle controls, and the 1.0 µg Zven1-treated (high dose) mice.

Serum levels of KC in the 0.1 µg Zven1-treated mice were considerably higher than the non-treated, the 1.0 µg Zven1-treated, and the vehicle-treated mice. The 0.1 µg Zven1-treated mice had KC levels of approximately 185 picograms/ml, which is a six-fold increase.

TABLE 5

Murine KC in Zven1-treated mice following IP injection

| | Concentration of Murine KC (picogram/ml) | | | |
|---|---|---|---|---|
| | Non-treated animals | Vehicle Control | 0.1 µg Zven1/animal | 1.0 µg Zven1/animal |
| Lavage Fluid | 10 | 21 | 45 | 8 |
| Serum | 30 | 38 | 185 | 50 |

These results are consistent with the stimulation of chemokine release in vitro shown in Example 2. Furthermore these results correlate with the observed neutriphil infiltration in the peritoneum in the 0.1 µg Zven1-treated (low dose) mice.

Example 4

Zven1 Effect on Gastric Emptying

Seven mice received an intraperitoneal injection of approximately 200 µg of Zven1 (10 µg/g body weight) or vehicle control followed by 7.5 mg phenol red. Gastric function was measured by monitoring phenol red transport through the gut after twenty minutes. The general behavior of Zven1 treated animals was observed and was consistent with the behavior of the control animals. In the Zven1-treated mice, gastric transit time was reduced by approximately 50%.

These results show that, at high doses following intraperitoneal injection, Zven1 reduces gastric transit. Zven1 administration did not appear to have any immediate toxic effects. This reduction in transit may be the result of a massive muscle contraction at such high doses. Zven1 may well increase motility in vivo at low doses, and inhibit motility at high doses.

Example 5

Stimulation of Angiogenesis by Zven1 and Zven2

Thoracic aortas were removed from twelve-day, five-week, and three-month old Wistar rats. The tissues were flushed with Hanks basic salt solution to remove any blood cells and adventitial tissues were removed. Aortic rings were prepared and plated on Matrigel coated plates in serum free modified MCDB media from Clonetics plus antibiotics, penicillin-streptomycin. Varying concentrations of Zven1 and Zven2 were added to culture dish approximately thirty minutes after plating. Proliferation was measured visually and individual rings were photographed to record results. Both Zven1 and Zven2 induced a proliferative response at concentrations ranging from 1 to 100 ng/ml. This mitogenic effect was observed in aortas from the animals at all three ages. Zven1 was also tested in the rat corneal model of anigiogenesis where no effect was noted. The observed angiogenic effect in the aortic ring cultures may be due to the mitogenic effects of the GROα homologue.

Example 6

Baculovirus Expression of Zven1

An expression vector containing a GLU-GLU tag, pzBV32L:zven1cee, was designed and prepared to express zven1cee polypeptides in insect cells.

A. Expression Vector:

An expression vector, pzBV32L:zven1cee, was prepared to express human zven1 polypeptides having a carboxy-terminal Glu-Glu tag, in insect cells as follows.

A 371 bp fragment containing sequence for zven1 and a polynucleotide sequence encoding EcoR1 and Xba1 restriction sites on the 5' and 3' ends, respectively, was generated by PCR amplification using PCR SuperMix (Gibco BRL, Life Technologies) and appropriate buffer from a plasmid containing zven1 cDNA (zven1-zyt-1.contig) using primers ZC29463 (SEQ ID NO:23) and ZC29462 (SEQ ID NO:24). (Note: the zven1 sequence and the Xba1 site was out of frame. An additional 2 bases, CC-antisense, were added to put in frame, which coded for an additional Gly between the zven1 sequence and the CEE tag.) The PCR reaction conditions were as follows: 1 cycle of 94° C. for 3 minutes, followed by 25 cycles of 94° C. for 30 seconds, 50° C. for 30 seconds, and 68° C. for 30 seconds; followed by a 4° C. hold. The fragment was visualized by gel electrophoresis (1% Agarose-1 µl of 10 mg/ml EtBr per 10 ml of agarose). A portion of the PCR product was digested with EcoR1 and Xba1 restriction enzymes in appropriate buffer, then run on an agarose gel. DNA corresponding to the EcoR1/Xba1 digested zven1 coding sequence was excised, purified using Qiagen Gel Extraction kit (#28704), and ligated into an EcoR1/XbaI digested baculovirus expression donor vector, pZBV32L. The pZBV32L vector is a modification of the pFastBac1™ (Life Technologies) expression vector, where the polyhedron promoter has been removed and replaced with the late activating Basic Protein Promoter. In addition, the coding sequence for the Glu-Glu tag (SEQ ID NO:10) as well as a stop signal is inserted at the 3' end of the multiple cloning region. About 216 nanograms of the restriction digested zven1 insert and about 300 ng of the corresponding vector were ligated overnight at 15° C. One µl of ligation mix was electroporated into 35 µl DH10B cells (Life Technologies) at 2.1 kV. The electroporated DNA and cells were diluted in 1 ml of LB media, grown for 1 hr at 37° C., and plated onto LB plates containing 100 µg/ml ampicillin. Clones were analyzed by restriction digests and one positive clone was selected and streaked on AMP+ plates to get single colonies for confirmation by sequencing.

Sequencing revealed the presence of a initiation codon upstream of the actual start codon which would possibly interfere with proper translation. Therefore, the upstream codon was removed using a Quick-change mutagenesis kit from Stratagene (La Jolla, Calif.). This was accomplished by designing forward and reverse primers that changed the upstream initiation ATG to a ATC, thereby also eliminating a Nco restriction digest site and creating a Sma1 site instead. The new mutagenized plasmid containing the Sma1 and Xba1 cleavage sites at the 5' and 3' ends of the zven1 sequence was then electroporated into DH10B cells as before, analyzed by restriction digests, this time with Sma1 and Xba1, and a positive clone was selected and streaked on AMP+ plates to get a single colony for confirmation by sequencing as before. A clone for the Zven1 polynucleotide sequence could also be cloned without the upstream initiation codon.

One to 5 ng of the positive clone donor vector was transformed into 100 μl DH10Bac Max Efficiency competent cells (GIBCO-BRL, Gaithersburg, Md.) according to manufacturer's instruction, by heat shock for 45 seconds in a 42° C. waterbath. The transformed cells were then diluted in 980 μl SOC media (2% Bacto Tryptone, 0.5% Bacto Yeast Extract, 10 ml 1M NaCl, 1.5 mM KCl, 10 mM $MgCl_2$, 10 mM $MgSO_4$ and 20 mM glucose) out-grown in shaking incubator at 37° C. for four hours and plated onto Luria Agar plates containing 50 μg/ml kanamycin, 7 μg/ml gentamicin, 10 μg/ml tetracycline, IPTG and Blue Gal. The plated cells were incubated for 48 hours at 37° C. A color selection was used to identify those cells having zven1cee encoding donor insert that had incorporated into the plasmid (referred to as a "bacmid"). Those colonies, which were white in color, were picked for analysis. Bacmid DNA was isolated from positive colonies using standard isolation technique according to Life Technologies directions. Clones were screened for the correct insert by amplifying DNA using primers to the transposable element in the bacmid via PCR. The PCR reaction conditions were as follows: 35 cycles of 94° C. for 45 seconds, 50° C. for 45 seconds, and 72° C. for 5 minutes; 1 cycle at 72° C. for 10 min.; followed by 4° C. soak. The PCR product was run on a 1% agarose gel to check the insert size. Those having the correct insert size were used to transfect Spodoptera frugiperda (Sf9) cells. The polynucleotide sequence is shown in SEQ ID NO:25. The corresponding amino acid sequence is shown in is shown in SEQ ID NO:26.

B. Transfection in Insect Cells:

Sf9 cells were seeded at $1 \times 10^6$ cells per 35 mm plate and allowed to attach for 1 hour at 27° C. Five micrograms of bacmid DNA was diluted with 100 μl Sf-900 II SFM medium (Life Technologies, Rockville, Md.). Fifteen μl of lipofectamine Reagent (Life Technologies) was diluted with 100 μl Sf-900 II SFM. The bacmid DNA and lipid solutions were gently mixed and incubated 30-45 minutes at room temperature. The media from one plate of cells was aspirated. Eight hundred microliters of Sf-900 II SFM was added to the lipid-DNA mixture. The DNA-lipid mix was added to the cells. The cells were incubated at 27° C. overnight. The DNA-lipid mix was aspirated the following morning and 2 ml of Sf-900 II media was added to each plate. The plates were incubated at 27° C., 90% humidity, for 168 hours after which the virus was harvested.

C. Primary Amplification

Sf9 cells were seeded at $1 \times 10^6$ cells per 35 mm plate and allowed to attach for 1 hour at 27° C. They were then infected with 500 μl of the viral stock from above and incubated at 27° C. for 4 days after which time the virus was harvested according to standard methods known in the art.

D. Secondary Amplification

Sf9 cells were seeded at $1 \times 10^6$ cells per 35 mm plate and allowed to attach for 1 hour at 27° C. They were then infected with 20 μl of the viral stock from above and incubated at 27° C. for 4 days after which time the virus was harvested according to standard methods known in the art.

E. Tertiary Amplification

Sf9 cells were grown in 80 ml Sf-900 II SFM in 250 ml shake flask to an approximate density of $1 \times 10^6$ cells/ml. They were then infected with 200 μl of the viral stock from above and incubated at 27° C. for 4 days after which time the virus was harvested according to standard methods known in the art.

F. Expression of Zven1cee

Third round viral stock was titered by a growth inhibition curve and the culture showing an MOI of "1" was allowed to proceed for 48 hrs. The supernatant was analyzed via Western blot using a primary monoclonal antibody specific for the n-terminal Glu Glu epitope and a HRP conjugated Gt anti Mu secondary antibody. Results indicated a band of the predicted molecular weight.

A large viral stock was then generated by the following method: Sf9 cells were grown in 1 L Sf-900 II SFM in a 2800 ml shake flask to an approximate density of $1 \times 10^6$ cells/ml. They were then infected with viral stock from the $3^{rd}$ round amp. and incubated at 27° C. for 72 hrs after which time the virus was harvested. Larger scale infections were completed to provide material for downstream purification.

Example 7

Expression in *E. coli*

A. Generation of the Native Zven1 Expression Construct

A DNA fragment of native Zven1 (SEQ ID NO:11) was isolated using PCR. Primer zc #40,821 (SEQ ID NO:12) containing 41 bp of vector flanking sequence and 24 bp corresponding to the amino terminus of Zven1, and primer zc#40,813 (SEQ ID NO:13) contained 38 bp corresponding to the 3' end of the vector which contained the zven1 insert. Template was pZBV32L:zven1cee. The PCR conditions were as follows: 25 cycles of 94° C. for 30 seconds, 50° C. for 30 seconds, and 72° C. for 1 minute; followed by a 4° C. soak. A small sample (2-4 μL) of the PCR sample was run on a 1% agarose gel with 1XTBE buffer for analysis, and the expected band of approximately 500 bp fragment was seen. The remaining volume of the 100 μL reaction was precipitated with 200 μL absolute ethanol. Pellet was resuspended in 10 μL water to be used for recombining into Sma1 cut recipient vector pTAP238 to produce the construct encoding the zven1 as disclosed above. The clone with correct sequence was designated as pTAP432. It was digested with Not1/Nco1 (10 μl DNA, 5 μl buffer 3 New England BioLabs, 2 μL Not 1, 2 μL Nco 1, 31 μL water for 1 hour at 37° C.) and religated with T4 DNA ligase buffer (7 μL of the previous digest, 2 μL of 5× buffer, 1 μL of T4 DNA ligase). This step removed the yeast sequence, CEN-ARS, to streamline the vector. The DNA was diagnostically digested with Pvu 2 and Pst 1 to confirm the absence of the yeast sequence. DNA was transformed into *E. coli* strain W3110/pRARE.

B. Expression of the Native Zven1 in *E. coli*

*E. coli* was inoculated into 100 ml Superbroth II medium (Becton Dickinson, Franklin Lakes, N.J.) with 0.01% Antifoam 289 (Sigma), 30 μg/ml kanamycin, 35 μg/ml chloramphenicol and cultured overnight at 37° C. A 5 ml inoculum was added to 500 ml of the same medium in a 2 L culture flask which was shaken at 250 rpm at 37° C. until the culture attained an $OD_{600}$ of 4. IPTG was then added to a final concentration of 1 mM and shaking was continued for another 2.5 hours. The cells were centrifuged at 4,000×g for 10 min at 4° C. The cell pellets were frozen at −80° C.

Example 8

Codon Optimization

A. Generation of the Codon Optimized Zven1 Expression Construct

Native human Zven1 gene sequence could not be expressed in *E. coli* strain W3110. Examination of the codons used in the Zven1 coding sequence indicated that it contained an excess of the least frequently used codons in *E. coli* with a CAI value equal to 0.211. The CAI is a statistical measure of synonymous codon bias and can be used to predict the level of protein production (Sharp et al., *Nucleic Acids Res.* 15(3): 1281-95, 1987). Genes coding for highly expressed proteins tend to have high CAI values (>0.6), while proteins encoded by genes with low CAI values ($\leq$0.2) are generally inefficiently expressed. This suggested a reason for the poor production of Zven1 in *E. coli*. Additionally, the rare codons are clustered in the second half of the message leading to higher probability of translational stalling, premature termination of translation, and amino acid misincorporation (Kane J F. *Curr. Opin. Biotechnol.* 6(5):494-500, 1995).

It has been shown that the expression level of proteins whose genes contain rare codons can be dramatically improved when the level of certain rare tRNAs is increased within the host (Zdanovsky et al., ibid., 2000; Calderone et al., ibid., 1996; Kleber-Janke et al., ibid., 2000; You et al,. ibid., 1999). The pRARE plasmid carries genes encoding the tRNAs for several codons that are rarely used *E. coli* (argU, argW, leuW, proL, ileX and glyT). The genes are under the control of their native promoters. Co-expression with pRARE enhanced Zven1 production in *E. coli* and yielded approximately 100 mg/L. Co-expression with pRARE also decreased the level of truncated zven1 in *E. coli* lysate. These data suggest that re-resynthesizing the gene coding for zven1 with more appropriate codon usage provides an improved vector for expression of large amounts of zven1.

The codon optimized zven1 coding sequence (SEQ ID NO:14) was constructed from six overlaping oligonucleotides: zc45,048 (SEQ ID NO:15), zc45,049 (SEQ ID NO:16), zc45,050 (SEQ ID NO:17), zc45,051 (SEQ ID NO:18), zc45,052 (SEQ ID NO:19) and zc45,053 (SEQ ID NO:20). Primer extension of these overlapping oligonucleotides followed by PCR amplication produced a full length zven1 gene with codons optimized for expression in *E. coli*. The final PCR product was inserted into expression vector pTAP237 by yeast homologous recombination. The expression construct was extracted from yeast and transformed into competent *E. coli* DH10B. Clones resistance to kanamycin were identified by colony PCR. A positive clone was verified by sequencing and subsequently transformed into production host strain W3110. The expression vector with the optimized zven1 sequence was named pSDH187. The resulting gene was expressed very well in *E. coli*. Expression levels with the new construct increased to around 150 mg/L.

B. Expression of the Codon Optimized Zven1 in *E. coli*

*E. coli* was inoculated into 100 ml Superbroth II medium (Becton Dickinson) with 0.01% Antifoam 289 (Sigma), 30 µg/ml kanamycin and cultured overnight at 37° C. A 5 ml inoculum was added to 500 ml of same medium in a 2 L culture flask which was shaken at 250 rpm at 37° C. until the culture attained an $OD_{600}$ of 4. IPTG was then added to a final concentration of 1 mM and shaking was continued for another 2.5 hours. The cells were centrifuged at 4,000×g for 10 min at 4° C. The cell pellets were frozen at −80° C. until use at a later time.

Example 9

Purification and Refolding of Zven1 Produced in *E. coli*

A. Inclusion Body Isolation:

Following induction of protein expression in either batch ferment or shaker flask culture, the *E. coli* broth was centrifuged in 1 liter bottles at 3000 RPM in a Sorvall swinging bucket rotor. Additional washing of the cell paste to remove any broth contaminants was performed with 50 mM Tris pH 8.0 containing 200 mM NaCl and 5 mM EDTA until the supernate was clear.

The cell pellets were then suspended in ice cold lysis buffer (50 mM Tris pH 8.0; 5 mM EDTA; 200 mM NaCl, 10% sucrose (w/v); 5 mM DTT; 5 mM Benzamidine;) to 10-20 Optical Density units at 600 nm. This slurry was then subjected to 2-3 passes at 8500-9000 psi in a chilled APV 2000 Lab Homogenizer producing a disrupted cell lysate. The insoluble fraction (inclusion bodies) was recovered by centrifugation of the cell lysate at 20,000×G for 1 hour at 4° C.

The inclusion body pellet (resulting from the 20,000×G spin) was re-suspended in wash buffer (50 mM Tris pH 8 containing 200 mM NaCl, 5 mM EDTA, 5 mM DTT, 5 mM Benzamidine) at 10 ml wash buffer per gram inclusion bodies, and was completely dispersed utilizing an OMNI international rotor stator generator. This suspension was centrifuged at 20,000×G for 30 minutes at 4° C. The wash cycle was repeated 3-5 times until the supernatant was clear.

The final washed pellet was solubilized in 8M Urea, 50 mM Borate buffer at pH 8.6 containing 0.1M Sodium Sulfite and 0.05 M Sodium Tetrathionate at pH 8.2. The solubilization and sulfitolysis reaction was allowed to proceed at 4° C. overnight with gentle shaking. The resulting pinkish colored solution was centrifuged at 35,000×g for 1 hour at 4° C. and the clarified supernate, containing the soluble Zven1, was 0.45 um filtered.

B. Zven1 Refolding:

The solubilized Zven1 was refolded by drop-wise dilution into ice cold refolding buffer containing 55 mM Borate pH 8.6, 1.0 M Arginine, 0.55 M Guanidine HCL, 10.56 mM NaCl, 0.44 mM KCl, 0.055% PEG, 10 mM reduced Glutathione and 1.0 mM oxidized Glutathione at a final zven1 concentration of 100-150 ug/ml. Once diluted, the mixture was allowed to stir slowly in the cold room for 48-72 hours.

C. Product Recovery & Purification:

After refolding, the solution was clarified by centrifugation at 22,000×G, 1 hour, 4° C. and/or by filtration using a 0.45 micron membrane. The clarified supernate, containing refolded zven1, was adjusted to 50 mM acetate and the pH adjusted to 4.5 with addition of HCl. The pH adjusted material was captured by cation exchange chromatography on a Pharmacia Streamline SP column (33 mm ID×65 mm length) equilibrated in 50 mM acetate pH 4.5 buffer. The load flow rate was 10 ml/min with inline dilution proportioning 1:5 in 50 mM acetate buffer at pH 4.5. This dilution lowers the ionic strength enabling efficient binding of the target to this matrix. After sample loading was complete, the column was washed to baseline absorbance with equilibration buffer prior to step elution with 50 mM acetate pH 4.5 buffer containing 1 M NaCl.

The eluate pool from the cation exchange step was brought to 1% Acetic acid, pH 3.0 and Loaded to a column (22 mm×130 mm) containing Toso Hass Amberchrom CG71m reverse phase media equilibrated in 1% acetic acid, pH 3.0 at a flow rate of 10 ml/min. Upon washing to baseline absorbance, the column was eluted with a 20 column volume gradient formed between equilibration buffer and 99% (V/V) acetonitrile, 1% (V/V) acetic acid.

The eluate pool from the reverse phase step was subjected to another round of cation exchange chromatography. The pool was directly loaded on to a Toso Haas SP 650 S column (10 mm×50 mm) equilibrated in 50 mM acetete pH 4.5 buffer at a flow rate of 3 ml/min. Upon completing the sample load, and washing to baseline absorbance, the column was step eluted with 50 mM acetate pH 3.0 buffer containing 1.0 M NaCl. The protein eluate pool was concentrated against a 3 k Da cutoff ultrafiltration membrane using an Amicon concentration unit in preparation for the final purification and buffer exchange size exclusion step.

D. Size Exclusion Buffer Exchange and Formulation:

The concentrated cation pool was injected onto a Pharmacia Superdex Peptide size exclusion column (Pharmacia, now Pfizer, La Jolla, Calif.) equilibrated in 25 mM Histidine; 120 mM NaCl at pH 6.5. The symetric eluate peak containing the product was pooled, 0.2 micron sterile-filtered, aliquoted and stored at −80° C.

Example 10

Activity of Zven1 and Zven2 in a Reporter Assay

A. Cell Lines

Rat2 fibroblast cells (ATCC #CRL-1764, American Type Culture Collection, Manassass, Va.) were transfected with a SRE luciferase reporter construct and selected for stable clones. These were then transfected with constructs for either GPCR73a receptor (SEQ ID NO:21) or GPCR73b receptor (SEQ ID NO:22).

B. Assay Procedure

Cells were trypsinized and seeded in Corning 96-well white plates at 3,000 cells/well in media containing 1% serum and incubated overnight at 37° C. and 5% $CO_2$. Media was removed and samples were added in triplicate to cells in media containing 0.5% BSA and incubated for four hours at 37° C. and 5% $CO_2$. After media was removed the cells were lysed and luciferase substrate was added according to the Promega luciferase assay system (Promega Corp., Madison, Wis.)

C. Data and Conclusions

All data were reported as fold-induction of the RLU (relative light units) from the meter divided by the basal signal (media only). Zven1 was prepared in house. Zven2 used in the assay was purchased from PeproTech Inc. (Rocky Hill, N.J.).

Tables 8 and 9 show that Zven1 was more active than Zven2 in a dose-dependent with cells expressing the GPCR73a receptor.

TABLE 8

| GPCR 73a Fold-induction | | |
|---|---|---|
| conc. (ng/ml) | Zven1 (*E. coli* produced) | Zven2 |
| 1000 | 17.8 | 20 |
| 320 | 20.7 | 24.4 |
| 100 | 19 | 11.4 |
| 32 | 15 | 5.8 |
| 10 | 8.4 | 2.5 |
| 3.2 | 4 | 1.6 |
| 1 | 1.9 | 1.2 |

TABLE 9

| GPCR73a Fold-induction | | |
|---|---|---|
| conc. (ng/ml) | Zven1 (*E. coli* produced) | Zven2 |
| 1000 | 13.9 | 15 |
| 320 | 22 | 20.5 |
| 100 | 17.6 | 11.4 |
| 32 | 14.1 | 7.2 |
| 10 | 10.2 | 2.6 |
| 3.2 | 7.6 | 1.3 |
| 1 | 4.1 | 0.95 |

Tables 10 and 11 show that Zven1 and Zven2 were similar in activity with the cells expressing the GPCR73b receptor. Activity of both molecules was lower in the cells expressing the GPCR73b receptor. It is not known if the GPCR73b receptor numbers were equivalent in both cell lines.

TABLE 10

| GPCR73b Fold-induction | | |
|---|---|---|
| conc. (ng/ml) | Zven1 (*E. coli* produced) | Zven2 |
| 1000 | 7.1 | 8.4 |
| 320 | 6.3 | 8.3 |
| 100 | 4.7 | 5.6 |
| 32 | 3 | 2.8 |
| 10 | 1.9 | 1.8 |
| 3.2 | 1.3 | 1.3 |
| 1 | 0.7 | 1.1 |

TABLE 11

| GPCR73b Fold-induction | | |
|---|---|---|
| conc. (ng/ml) | Zven1 (*E. coli* produced) | Zven2 |
| 1000 | 4.8 | 6.1 |
| 320 | 5.2 | 5.8 |
| 100 | 4.4 | 4.1 |
| 32 | 2.6 | 2.7 |
| 10 | 1.7 | 1.8 |
| 3.2 | 1.2 | 1.4 |
| 1 | 1 | 1.1 |

Table 12 shows that Baculovirus-expressed Zven1 that has been heated at 56° C. for 30 minutes may have reduced activity than fresh Zven1.

TABLE 12

| GPCR73a Fold-induction | | |
|---|---|---|
| conc. (ng/ml) | Fresh Zven1 | Heated Zven1 |
| 100 | 20.5 | 18.6 |
| 32 | 18.7 | 14.8 |
| 10 | 13.1 | 10 |
| 3.2 | 7.1 | 3.7 |
| 1 | 2.5 | 1.8 |

Example 11

MIP-2 Detection in Lavage Fluids and Serum of Mice Following IP (Intraperitoneal) Injection of Zven1

As discussed in Example 3, above, mouse KC is the mouse homolog of human GROα, and CINC-1 is the rat homolog. Similarly, increased MIP-2 expression has been found to be associated with neutrophil influx in various inflammatory conditions. See Banks, C. et al, *J. Path.* 199: 28-35, 2003.

Similar to the methods used in Example 3, four groups of ten mice were injected with Zven1 at 5 and 50 ug/kg, a vehicle control, or no treatment. These mice weighed approximately 20 grams, so the dose was 5 µg/kg. MIP-2 levels were measured in both peritoneal lavage fluid and serum using a Quantikine M Murine mouse MIP-2 ELISA kit (R and D Systems, Minneapolis, Minn.). Test results are shown in Table 16.

TABLE 16

| | MIP-2 picograms/ml | |
|---|---|---|
| | Serum | Lavage Fluid |
| Non-treated control | 6.2 +/− 1.3 | 5.9 +/− 0.7 |
| Vehicle | 6.7 +/− 1.3 | 16.7 +/− 2.2 |
| 5 ug/kg Zven1 | 14.3 +/− 2.7 | 21.5 +/− 3.7 |
| 50 ug/kg Zven1 | 7.7 +/− 1.8 | 8.7 +/− 1.2 |

Data = mean +/− SEM

Conclusions: MIP-2 is up-regulated in serum and lavage fluid in response to a low, (5 ug/kg), IP injection of zven1. Concentrations in serum are approximately 2-fold higher in the zven1 treated animals. There is a lesser effect in lavage fluid, but that is due to the fact that some activation took place in the vehicle treated animals over non-treated control animals. At the higher (50 ug/kg dose) no effect was observed suggesting that at elevated doses there is no chemotactic effect. These results correlate with the neutrophil numbers, where in, neutrophil infiltration was observed only in the animals administered the lower (5 ug/kg) dose of Zven1.

Example 12

Production of Zven1 Polyclonal Antibodies

Polyclonal antibodies were prepared by immunizing 2 female New Zealand white rabbits with the purified recombinant protein huzven1-CEE-Bv (SEQ ID NO:24) The rabbits were each given an initial intraperitoneal (ip) injection of 200 µg of purified protein in Complete Freund's Adjuvant followed by booster ip injections of 100 µg peptide in Incomplete Freund's Adjuvant every three weeks. Seven to ten days after the administration of the second booster injection (3 total injections), the animals were bled and the serum was collected. The animals were then boosted and bled every three weeks.

Polyclonal antibodies were purified from the immunized rabbit serum using a 5 ml Protein A sepharose column (Pharmacia LKB). Following purification, the polyclonal antibodies were dialyzed with 4 changes of 20 times the antibody volume of PBS over a time period of at least 8 hours. Huzven1-specific antibodies were characterized by ELISA using 500 ng/ml of the purified recombinant protein huzven1-CEE-Bv (SEQ ID NO:24) as the antibody target. The lower limit of detection (LLD) of the rabbit anti-huzven1 purified antibody was 1 ng/ml on its specific purified recombinant antigen huzven1-CEE-Bv.

Example 13

Detection of Zven1 Protein

The purified polyclonal huzven1 antibodies were characterized for their ability to bind recombinant human Zven1 polypeptides using the ORIGEN(®) Immunoassay System (IGEN Inc, Gaithersburg, Md.). In this assay, the antibodies were used to quantitatively determine the level of recombinant huzven1 in rat serum samples. An immunoassay format was designed that consisted of a biotinylated capture antibody and a detector antibody, which was labeled with ruthenium (II) tris-bipyridal chelate, thereby sandwiching the antigen in solution and forming an immunocomplex. Streptavidin-coated paramagnetic beads were then bound to the immunocomplex. In the presence of tripropylamine, the ruthenylated Ab gave off light, which was measured by the ORIGEN analyzer. Concentration curves of 0.1-50 ng/ml huzven1 made quantitation possible using 50 microliters of sample. The resulting assay exhibited a lower limit of detection of 200 pg/ml huzven1 in 5% normal rat serum.

Example 14

Zven1 and Inflammatory Bowel Disease (IBD)

The purpose was to determine if Zven1 expression was up-regulated in IBD, intestinal tissue biopsies from six ulcerative colitis (UC) patients, seven Crohn's disease patients, and four normal donor controls were analyzed using Taqman RTPCR. Tissue biopsies were obtained from two sites in the intestine from each individual donor, one site with no or low amounts of inflammation and one diseased site. In some instances, no unaffected areas could be found. Sites of biopsy obtainment included: Cecum, rectum, transverse, ascending, and descending colon, terminal ileum, and signum.

Immediately following biopsy, tissues were flash frozen in liquid nitrogen. Tissue was crushed and resuspended in lysis buffer: 2% SDS, 20 mM Tris (pH 7.4), and 2% Phosphotase Inhibitor Cocktail (Sigma, Saint Louis, Mo.). RNA was prepared using RNeasy kits from (Qiagen, Valencia, Calif.), following manufacturer's instructions. Taqman EZ RT-PCR Core Reagent Kit (Applied Biosystems, Foster City, Calif.) was used to determine Zven1 expression levels.

Following manufacturer's instructions a Zven1 standard curve was prepared using human testis RNA at different concentrations (250 ng/µl, 50 ng/µl, 12.5 ng/µl and 3.125 ng/µl). These standard curve dilutions were first used to test the primers designed for Zven1 gene and for a housekeeping gene (human glucuronidase (GUS). Once the working conditions of primer and standard curve were established, intestinal disease RNA samples were tested. The RNA samples were thawed on ice and then were diluted to 50 ng/µl in RNase-free water (Invitrogen, Cat #750023). Diluted samples were kept on ice all the time.

Using the TaqMan EZ RT-PCR Core Reagent Kit (Applied Biosystems, Cat#N808-0236), master mix was prepared for both Zven1 and for a housekeeping gene (GUS). To assay samples in triplicate, 3.5 µl of each RNA samples were aliquoted. For positive controls, 3.5 µl each standard curve dilutions were used in place of sample RNA. For the negative control, 3.5 µl RNase-free water was used for a no template control. For endogenous controls (human GUS message), 3.5 µl of both standard curve dilutions and the sample RNAs were aliquoted. Then 84 µl of PCR master mix was added and mixed well by pipetting. A MicroAmp Optical 96-well Reaction Plate (Applied Biosystems Cat# N801-0560) was placed on ice and 25 μl of RNA/master mix was added in triplicates to the appropriate wells. Then MicroAmp 12-Cap Strips (Applied Biosystems Cat# N801-0534) were used to cover entire plate. The plate was then spun for two minutes at 3000 RPM in the Qiagen Sigma 4-15 centrifuge.

The samples were run on a PE-ABI 7700 (Perkin Elmer, now EG&G, Inc. Wellesley, Mass.). Sequence Detector was launched and the default was set to Real Time PCR. Fluorochrome was set to FAM. Plate template was set to indicate where standards and where unknown test samples were.

Expression for each sample was reported as a Ct value. The Ct value was the point at which the fluorochrome level or RT-PCR product (a direct reflection of RNA abundance) was amplified to a level, which exceeds the threshold or background level. The lower the Ct value, the higher the expression level, since RT-PCR of a highly expressing sample results in a greater accumulation of fluorochrome/product which crosses the threshold sooner. A Ct value of 40 indicates that there was no product measured and should result in a mean expression value of zero. The Ct was converted to relative expression value based on comparison to the standard curve. For each sample was being tested, the amount of Zven1 and GUS expression level was determined from the appropriate standard curve. Then these calculated Zven1 expression values were divided by the GUS expression value for each sample in order to obtain a normalized Zven1 expression value for each sample.

Results: In the four normal donor tissues, Zven1 relative expression was extremely low (mean 0.07+/−0.07 SEM). In both UC and Crohn's diseased tissues, Zven1 expression was significantly elevated compared to the expression seen in normal donors. Mean relative Zven1 expression in UC and Crohn's patients with minimally inflamed tissue was: 4.9+/−10 SEM in UC, and 1.45+/−0.8 SEM in Crohn's.

Mean fold-increase over normal donors was 70-fold in UC and 20.7-fold in Crohn's. In the inflamed tissue samples, Zven1 expression was even higher. Mean fold Zven 1 expression in inflamed UC tissue was 15.8+/−18.5 SEM and 40.8+/−92.8 SEM in Crohn's disease inflamed tissue. Mean fold increase in Zven1 expression over normals in UC was 213-fold and in Crohn's was 583-fold.

All thirteen UC and Crohn's donor inflamed intestinal tissue biopsies had Zven1 expression levels higher than the mean normal donor biopsies.

Conclusions: Zven1 has been shown to induce chemokine release both in vitro and in vivo. See Examples 2 and 3 above. Furthermore, following IP injection in mice, two potent chemokines, mouse KC (as shown in Example 3) and MIP-2 (as shown in Example 11) can be measured in the peritoneum and the blood stream, accompanied by an influx of neutrophils. Additionally, as shown in this Example, Zven1 was up-regulated in intestinal tissues obtained from inflammatory bowel disease patients suggesting that it may be involved in the inflammatory process and the progression of IBD.

These results are consistent with studies that show that chemokines are chemotactic cytokines that are able to promote leukocyte migration to areas of inflammation and have recently been implicated in the pathophysiology of many disease states, including IBD. Mucosal changes in IBD were characterized by ulcerative lesions accompanied by prominent cellular infiltrates in the bowel.

Example 15

Measurements of Zven1 in Irritable Bowel Syndrome

In order to determine if Zven1 expression is dys-regulated in IBS, circulating levels were measured in plasma samples from women approximately 20-45 years of age that were carefully screened for the presence of current IBS symptoms. Samples were obtained from donors displaying mild or moderate IBS symptoms. An equal number of healthy control donor plasmas were also obtained. The non-symptomatic group denied any history of IBS or IBS-like GI symptoms or poor sleep. In addition, all studies were performed within the same menstrual cycle phase to control for potential cycle phase differences. A total of twelve plasma samples were obtained during the night for the measurement of stress related hormones and Zven1 (prokineticin 2). Blood was drawn at 8:00 p.m. (20 hours), and hourly there after until 7:00 a.m. (7 hours).

A. Platelet-Rich Plasma Preparation:

Approximately 4.5 ml of blood was collected into EDTA tubes and mixed by gentle inversion. Samples were stored on ice until all samples have been collected. Blood was centrifuged for 10 minutes at 200×g at 4° with brake off. The plasma fraction was decanted and aliquoted into tubes and frozen at −80° C.

Samples were stored frozen until the day they were assayed for Zven1 levels. Upon thawing, samples were spun at 13,000 rpm for 5 minutes at room temperature to remove any debris. Plasmas were diluted 1:4 in ELISA-B buffer (1% BSA in ELISA-C buffer) and each individual sample was run in triplicate.

B. ELISA:

A sandwich based ELISA protocol was used to assay the plasma samples for circulating zven1. Nunc-Immuno 96-well Maxisorp Surface ELISA plates were coated with a polyclonal rabbit anti-human antibody at a concentration of 1.06 μg/ml, which was prepared in ELISA-A buffer (0.1 M $Na_2CO_3$, pH 9.6). Then plates were sealed and incubated overnight at 4° C.

The next day, the plates were washed 5 times with ELISA-C buffer (1×PBS, 0.05% v/v Tween 20) and then they were blocked twice with SuperBlock (Pierce, Cat #37515) at room temperature for 5 minutes. Plates were washed 5 times with ELISA-C buffer before adding the samples and the standards to the plate.

For standard curve preparation, pooled platelet-rich plasma was prepared. Briefly, blood from four healthy individuals was drawn into EDTA containing tubes. Blood was spun at 200×g at 4° C. for 10 minute. Plasma from all four donors was pooled and aliquots were kept at −80° C.

On assay day, frozen platelet-rich plasma was thawed and spun for 5 minutes at 10,000 rpm to remove debris. Both standard curve plasma and human patient test plasmas were diluted 1:4 in ELISA-B buffer. E. coli produced Zven1 protein was spiked into the standard curve plasma at known concentrations to prepare a standard curve. Dilution series ran from 25 ng/ml to 0.08 ng/ml.

Both standard curve dilutions and samples were added to the plates in triplicate. Plates were sealed and incubated at 37° C. for 2 hours on a shaker. After the incubation, plates were washed five times with ELISA-C buffer.

For detection, biotinylated rabbit anti-human polyclonal zven-1 antibody was diluted to 500 ng/ml in ELISA-B buffer. The ELISA plates were coated with antibody and incubated at 37° C. for an hour on a shaker. Following the incubation, plates were washed with ELISA-C buffer. Strepavidin horse radish peroxidase SA-HRP (Pierce) was diluted to 250 ng/ml in ELISA-B buffer and added to the plates. Plates were sealed and incubated at 37° C. for an hour on a shaker. After this incubation period, the plates were washed with ELISA-C buffer and Tetra methyl benzidine (TMB) solution (BioFX, Cat# TMBW-10000-01) was added to the plates at room temperature and incubated for 30 minutes on the bench. Color development was stopped with Stop Solution (BioFX 450 Stop Reagent, Cat# STPR-1000-01) and the absorbance at 450 nm minus 540 nm was read on a spectrophotometer (Molecular Devices) within 15 minutes of stop. Protein amounts were calculated from the standard curve using the SoftMax Pro software program.

C. Results:

Control donor samples show lower levels of Zven1. While levels of Zven1 were highest in the samples drawn prior to midnight and after and including the 6:00 a.m, no Zven1 expression was detecting in control donors between midnight and 6:00 a.m. The final concentration of zven1/ml was relatively low, with maximal values reaching levels of approximately 119 picograms/ml.

In the IBS donors, both the amounts of circulating Zven1 were higher than controls, and the pattern of expression was different, with expression observed throughout the night. Maximal Zven1 levels were approximately 9-fold higher, at 917 picograms/ml in the IBS patients. In addition, unlike the control donors, circulating Zven1 was detected in the samples obtained throughout the night (from midnight until 7:00 a.m).

D. Conclusions:

In normal control patients, Zven1 expression follows a circadian pattern, with levels at there highest in the night and in the morning when the digestive process is either active, or commencing. In the IBS patients, this circadian pattern of expression is dys-regulated, suggesting Zven1 is involved in the pathology of IBS and contributes to the IBS syndrome. Zven1's profound effect on gut motility, both in the organ bath and in vivo, also support a connection to the altered intestinal motility symptoms related to IBS. A Zven1 antagonist could relieve the symptoms of constipation (or diarrhea), sleeplessness, abdominal bloating and increased sensitivity to pain sensation experienced in IBS patients.

Example 16

Expression of GPR73a and GPR73b in Rat Gastrointestinal Tract

Rats were fasted overnight and sacrificed. Intestines and stomachs were isolated and four-centimeter tissue sections from the stomach through the end of the colon were immediately flash frozen in liquid nitrogen. Acid-Phenol extraction method was used for RNA isolation. Briefly, tissue sections were grinded in liquid nitrogen then lysed/homogenized in acid guanidium based lysis buffer (4M Guanidine isothyocyanate, 25 mM sodium citrate (pH 7), 0.5% sarcosyl), NaOAc (0.1M final concentration) +βME (1:100). Lysates were spun down; supernatants were mixed with equal volume of acid phenol and 1/10 volume chloroform. After spinning down, equal volume of Isopropanol was added to the aqueous layer. Samples were incubated at −20° C. then pelleted down by spinning. Pellets were washed with 70% EtOH and then resuspended in DEPC treated water.

Taqman EZ RT-PCR Core Reagent Kit (Applied biosystems, Foster City, Calif.) was used to determine GPR73a and GPR73b receptor expression levels. Following manufacturer's instructions, a standard curve was prepared using one of the RNA isolates which had a high quality RNA and which showed expression of both receptors at the same level. Standard curve dilutions of this RNA sample were prepared at the following concentrations: 500 ng/µl, 250 ng/µl, 100 ng/µl and 12.5 ng/µl. These standard curve dilutions were first used to test the primers designed for GPR73a and GPR73b genes and for a housekeeping gene, rodent glyceraldehyde-3-phosphate dehydrogenase (GAPDH). Once the working conditions of primer and standard curve were established, RNA samples isolated from rat were tested.

The RNA samples were thawed on ice and diluted to 100 ng/µl in RNase-free water (Invitrogen, Cat #750023). Diluted samples were kept on ice during the experiment. Using the TaqMan EZ RT-PCR Core Reagent Kit (Applied Biosystems, Cat# N808-0236), master mix was prepared for GPR73a, GPR73b receptors and for the house keeping gene. To assay samples in triplicate, 3.5 µl of each RNA samples were aliquoted. For positive controls, 3.5 µl of each standard curve dilutions were used in place of sample RNA. For the negative control, 3.5 µl RNase-free water was used for the no template control. For endogenous controls (rodent GAPDH message), 3.5 µl of both standard curve dilutions and the sample RNAs were aliquoted. Then 84 µl of PCR master mix was added and mixed well by pipetting.

A MicroAmp Optical 96-well Reaction Plate (Applied Biosystems Cat# N801-0560) was placed on ice and 25 µl of RNA/master mix was added in triplicates to the appropriate wells. Then MicroAmp 12-Cap Strips (Applied Biosystems Cat# N801-0534) were used to cover entire plate. Then the plate was spun for two minutes at 3000 RPM in the Qiagen Sigma 4-15 centrifuge.

The samples were run on a PE-ABI 7700 (Perkin Elmer, now EG&G, Inc. Wellesley, Mass.). Sequence Detector was launched and the default was set to Real Time PCR. Fluorochrome was set to FAM. Plate template was set to indicate where standards and where unknown test samples were.

Expression for each sample is reported as a Ct value. The Ct value is the point at which the fluorochrome level or RT-PCR product (a direct reflection of RNA abundance) is amplified to a level, which exceeds the threshold or background level. The lower the Ct value, the higher the expression level, since RT-PCR of a highly expressing sample results in a greater accumulation of fluorochrome/product which crosses the threshold sooner. A Ct value of 40 means that there was no product measured and should result in a mean expression value of zero. The Ct is converted to relative expression value based on comparison to the standard curve. For each sample tested, the amount of GPR73a, GPR73b and GAPDH expression level was determined from the appropriate standard curve. Then these calculated expression values of GPR73a and GPR73b were divided by the GAPDH expression value of each sample in order to obtain a normalized expression for each sample. Each normalized expression value was divided by the normalized-calibrator value to get the relative expression levels. Using GraphPad Prism software, these normalized values were converted to fractions in which the highest expression level was indicated as 1.

TABLE 15

Normalized values (represented in fractions) for GPR73a and GPR73b expressions in rat.

| Samples | GPR73a normalized value | StDev | N | Samples | GPR73b normalized value | StDev | N |
|---|---|---|---|---|---|---|---|
| Forestomach | 0.067 | 0.057 | 3 | Forestomach | 0.063 | 0.013 | 3 |
| Fundus | 0.003 | 0.023 | 3 | Fundus | 0.106 | 0.033 | 3 |

TABLE 15-continued

Normalized values (represented in fractions) for GPR73a and GPR73b expressions in rat.

| Samples | GPR73a normalized value | StDev | N | Samples | GPR73b normalized value | StDev | N |
|---|---|---|---|---|---|---|---|
| Antrum | 0.000 | 0.016 | 3 | Antrum | 0.000 | 0.004 | 3 |
| Pylorus/Antrum | 0.041 | 0.016 | 3 | Pylorus/Antrum | 0.104 | 0.005 | 3 |
| Duodenum | 0.107 | 0.035 | 3 | Duodenum | 0.205 | 0.037 | 3 |
| Jejunum-1 | 0.102 | 0.035 | 3 | Jejunum-1 | 0.100 | 0.058 | 3 |
| 2 | 0.087 | 0.020 | 3 | 2 | 0.021 | 0.008 | 3 |
| 3 | 0.126 | 0.037 | 3 | 3 | 0.097 | 0.016 | 3 |
| 4 | 0.250 | 0.054 | 3 | 4 | 0.150 | 0.042 | 3 |
| 5 | 0.268 | 0.030 | 3 | 5 | 0.123 | 0.022 | 3 |
| 6 | 0.240 | 0.024 | 3 | 6 | 0.177 | 0.037 | 3 |
| 7 | 0.339 | 0.039 | 3 | 7 | 0.173 | 0.031 | 3 |
| 8 | 0.329 | 0.107 | 3 | 8 | 0.129 | 0.031 | 3 |
| 9 | 0.327 | 0.101 | 3 | 9 | 0.286 | 0.078 | 3 |
| 10 | 0.425 | 0.071 | 3 | 10 | 0.235 | 0.011 | 3 |
| 11 | 0.379 | 0.011 | 3 | 11 | 0.147 | 0.016 | 3 |
| 12 | 0.577 | 0.076 | 3 | 12 | 0.253 | 0.068 | 3 |
| 13 | 0.570 | 0.043 | 3 | 13 | 0.315 | 0.053 | 3 |
| 14 | 0.250 | 0.011 | 3 | 14 | 0.171 | 0.017 | 3 |
| 15 | 0.492 | 0.027 | 3 | 15 | 0.397 | 0.034 | 3 |
| 16 | 0.989 | 0.089 | 3 | 16 | 0.494 | 0.048 | 3 |
| 17 | 0.977 | 0.313 | 3 | 17 | 0.420 | 0.045 | 3 |
| 18 | 1.000 | 0.061 | 3 | 18 | 0.523 | 0.146 | 3 |
| Ileum-1 | 0.797 | 0.080 | 3 | Ileum-1 | 0.630 | 0.141 | 3 |
| 2 | 0.636 | 0.014 | 3 | 2 | 0.434 | 0.080 | 3 |
| 3 | 0.614 | 0.015 | 3 | 3 | 0.441 | 0.115 | 3 |
| 4 | 0.923 | 0.085 | 3 | 4 | 0.871 | 0.288 | 3 |
| 5 | 0.807 | 0.142 | 3 | 5 | 0.739 | 0.017 | 3 |
| 6 | 0.755 | 0.080 | 3 | 6 | 1.000 | 0.246 | 3 |
| Cecum | 0.088 | 0.020 | 3 | Cecum | 0.369 | 0.036 | 3 |
| Proximal | 0.171 | 0.060 | 3 | Proximal | 0.887 | 0.021 | 3 |
| Middle | 0.088 | 0.051 | 3 | Middle | 0.209 | 0.047 | 3 |
| Distal | 0.047 | 0.019 | 3 | Distal | 0.012 | 0.002 | 3 |

Example 17

Zven1 and Monoclonal Antibodies

Rat monoclonal antibodies are prepared by immunizing 4 female Sprague-Dawley Rats (Charles River Laboratories, Wilmington, Mass.), with the purified recombinant protein from Example 6 or Example 7, above. The rats are each given an initial intraperitoneal (IP) injection of 25 □g of the purified recombinant protein in Complete Freund's Adjuvant (Pierce, Rockford, Ill.) followed by booster IP injections of 10 □g of the purified recombinant protein in Incomplete Freund's Adjuvant every two weeks. Seven days after the administration of the second booster injection, the animals are bled and serum is collected.

The Zven1-specific rat sera samples are characterized by ELISA using 1 ug/ml of the purified recombinant protein Zven1 as the specific antibody target.

Splenocytes are harvested from a single high-titer rat and fused to SP2/0 (mouse) myeloma cells using PEG 1500 in a single fusion procedure (4:1 fusion ratio, splenocytes to myeloma cells, "Antibodies: A Laboratory Manual, E. Harlow and D. Lane, Cold Spring Harbor Press). Following 9 days growth post-fusion, specific antibody-producing hybridoma pools are identified by radioimmunoprecipitation (RIP) using the Iodine-125 labeled recombinant protein Zven1 as the specific antibody target and by ELISA using 500 ng/ml of the recombinant protein Zven1 as specific antibody target. Hybridoma pools positive in either assay protocol are analyzed further for their ability to block the cell-proliferative activity ("neutralization assay") of purified recombinant protein Zven1 on Baf3 cells expressing the receptor sequence of GPR73a (SEQ ID NO:27) and/or GPR73b (SEQ ID NO:28).

Hybridoma pools yielding positive results by RIP only or RIP and the "neutralization assay" are cloned at least two times by limiting dilution.

Monoclonal antibodies purified from tissue culture media are characterized for their ability to block the cell-proliferative activity ("neutralization assay") of purified recombinant Zven1 on Baf3 cells expressing the receptor sequences. "Neutralizing" monoclonal antibodies are identified in this manner.

A similar procedure is followed to identify monoclonal antibodies to Zven2 using the amino acid sequence in SEQ ID NO:5.

Example 18

Stimulation of Contractility in Guinea Pig Gastrointestinal Organ Bath Assay

Male Hartley Guinea pigs at six weeks of age weighing approximately 0.5 kg were euthanized by carbon monoxide. Intestinal tissue was harvested as follows: 2-3 cm longitudinal sections of ileum 10 cm rostral of the cecum, and 2-3 cm longitudinal sections of duodenum, jejunum, and proximal and distal colon.

Tissue was washed in Krebs Ringer's Bicarbonate buffer containing 118.2 mM NaCl, 4.6 mM KCl, 1.2 mm $MgSO_4$, 24.8 mM $NaHCO_3$, 1.2 mM $KH_2PO_4$, 2.5 mM $CaCl_2$ and 10 mM glucose. Following a thorough wash, the tissue was mounted longitudinally in a Radnoti organ bath perfusion system (SDR Clinical Technology, Sydney Australia) containing oxygenated Krebs buffer warmed and maintained at 37° C. A one gram pre-load was applied and the tissue strips were allowed to incubate for approximately 30 minutes.

Baseline contractions were then obtained. Isometric contractions were measured with a force displacement transducer and recorded on a chart recorder using Po-ne-mah Physiology Platform Software. The neurotransmitter 5 Hydroxytryptophane (5HT) (Sigma) at 130 μm, and atropine at 5-10 mM were used as controls. Atropine blocks the muscarinic effect of acetylcholine.

Varying doses of Zven1 from 1-400 ng/ml were tested for activity on strips of ileum. Muscle contractions were detected immediately after adding zven1 protein and were recorded at concentrations as low as 1 ng/ml or 100 picomolar. The EC 50 of this response was approximately 10 ng/ml or 1 nM. Zven1 was tested for activity in the presence of 5HT, and a secondary contraction was observed. Zven1 was tested for activity in the presence of 0.1 μM tetrodotoxin (TTX), the nerve action potential antagonist and no reduction in the zven1 effect was observed. Zven1 was also tested for activity in the presence of 100 nM Verapamil, the L-type calcium channel blocker. A significant reduction in the amplitude of the contractile response was observed.

Results of the effect of zven1 on contractions in the ileum are shown in Table 6.

TABLE 6

Summary of Ileum Organ Bath Test Results

| Treatment | Ileum |
|---|---|
| 40 ng/ml Zven1 | +C |
| 40 ng/ml Zven1 + 130 μM 5HT | +C |
| 40 ng/ml Zven1 + 5 mM Atropine | +C |
| 40 ng/ml Zven1 + 1 μM Verapamil | — |
| 40 ng/nL Zven1 + 0.1 μM TTX | +C |

+C = Contraction Observed
— = No zven1 effect observed

Results of the effect of zven1 on contractions in duodenum, jejunum, proximal colon, and distal colon were performed at a concentration of 40 ng/ml did not produce contractions in duodenum, jejunum, or distal colon. However, relaxation of the tissue of the proximal colon was observed when the same concentration of zven1 was added.

Example 19

Effect of Dose on Contractility in Guinea Pig Ileal Organ Bath Assay

All intestinal sections from the guinea pig ileum were obtained and tested using the same protocol and reagents as described in Example 6. Longitudinal strips of guinea pig ileum were mounted in the organ bath and allowed to stabilize for approximately 20 minutes. Acetylcholine (ACH) at a concentration of 10 μg/ml was added to tissue to confirm contractile activity. Two flush and fill cycles were run to wash ACH from the intestinal tissue. Baseline activity was confirmed for approximately 25 minutes. Zven1 was added to the organ bath at a final concentration of 1.0 ng/ml and an approximate 0.5 gram of deflection was recorded. The 1.0 ng/ml zven1 dose was left on the tissue for 5 minutes to allow the tissue to return to baseline levels, and then a 10 ng/ml dose was added. Another contractile response was noted that resulted in a 2.0 gram deflection. The 10 ng/ml dose was left on for another 5 minutes before dosing the tissue with a 20 ng/ml dose of zven1. Another contractile response was observed, yielding an approximate 2.2 gram deflection. Following a 5 minute incubation, the tissue was treated with a 40 ng/ml dose of zven1. The tissue contracted again, with an approximate 2.0 gram deflection. The highest response was observed at the 20 ng/mL zven1 dose.

Example 20

Effect of Zven1 on Gastric Emptying and Intestinal Transit

Eight-week old female C57B1/6 mice were fed a test meal consisting of a methylcellulose solution or a control, and both gastric emptying and intestinal transit was measured by determining the amount of phenol red recovered in different sections of the intestine. The test meal consists of a 1.5% aqueous methylcellulose solution containing a non-absorbable dye, 0.05% phenol red (50 mg/100 ml Sigma Chemical Company Catalogue # P4758). Medium viscosity carboxy methylcellulose from Sigma (Catalogue #C4888) with a final viscosity of 400-800 centipoises was used. One group of animals was sacrificed immediately following administration of test meal. These animals represent the standard group, 100% phenol red in stomach or Group VIII. The remaining animals were sacrificed 20 minutes post administration of test meal. Following sacrifice, the stomach was removed and the small intestine was sectioned into proximal, mid and distal gut sections. The proximal gut consisted approximately of duodenum, the mid gut consisted approximately of duodenum and jejunum, and the distal gut consisted approximately of ileum. All tissues were solubilized in 10 mls of 0.1 N NaOH using a tissue homogenizer. Spectrophotometric analysis was used to determine the OD and hence the level of gastric emptying and gut transit.

Each treatment group consisted of 10 animals, except for the animals being used as a standard group and the caerulein control group where the n=5. The study was broken down into two days, such that one half of all treatment groups are done on two consecutive days. The animals were fasted for 18 hrs in elevated cages, allowing access to water. The average weight of the mice was 16 grams.

Baculovirus-expressed Zven1 protein with a C-terminal Glu-Glu tag formulated in 20 mM MES buffer, 20 mM NaCl, pH 6.5 was diluted into 0.9% NaCl+0.1% BSA using siliconized tubes. (Sigma sodium chloride solution 0.9%, and Sigma BSA 30% sterile TC tested solution, Sigma Chemical Co, St Louis, Mo.). The protein concentration was adjusted so as to be contained in a 0.2 ml volume per mouse. Vehicle animals received an equivalent dose of zven1 formulation buffer based on the highest (775 ng/g) treatment group.

Treatments were administered in a 0.2 ml volume via IP (intraperitoneal) injection two minutes prior to receiving 0.15 ml phenol red test meal as an oral gavage. Twenty minutes post administration of phenol red, animals were euthanized and stomach and intestinal segments removed. The intestine was measured and divided into three equal segments: proximal, mid and distal gut. The amount of phenol red in each sample was determined by spectrophotometric analysis and expressed as the percent of total phenol red in the stomach (Group VIII). These values were used to determine the amount of gastric emptying and gut transit per tissue collected. The CCK analogue caerulein at 40 ng/gram was used as a positive control and was administered five minutes prior to gavage, at which concentration it inhibits gastric emptying. Colormetric analysis of phenol red recovered from each gut segment and stomach was performed as follows. After euthanization, the stomach and intestinal segments were placed into 10 mls of 0.1 N NaOH and homogenized using a polytron tissue homogenizer. The homogenate was incubated for 1 hour at room temperature then pelleted by centrifugation on a table top centrifuge at 150×g for 20 minutes at 4 degrees C. Proteins were precipitated from 5.0 mls of the homogenate by the addition of 0.5 ml of 20% trichloracetic acid. Following centrifugation, 4 mls of supernatant was added to 4 mls of 0.5 N NaOH. A 200 μl sample was read at 560 nm using Molecular Devices Spectra Max 190 spectrophotometer. The amount of gastric emptying was calculated using the following formula: percent gastric emptying=(1−amount phenol red recovered from test stomach/average amount of phenol red recovered from Group VII stomach)×100. The amount of gastric transit was expressed as the percent of total phenol red recovered.

Results are shown in Table 7, below. Since test meal was not detected in the distal gut under any conditions, these data are not included. As expected, caerulein at 40 ng/ml inhibited gastric emptying (93.8% of test meal in stomach after 20 minutes compared to 63.8% with vehicle). Consistent with inhibited gastric emptying, in the caerulein treated group only 2.6% of meal was measured in the proximal gut and 1.2% in the mid gut.

At the lowest zven1 concentration, 0.78 ug/kg body weight, a slight increase in gastric emptying compared to vehicle was observed (56.3% of meal remaining versus 63.8% with vehicle). Consistent with an increase in gastric emptying, increased meal was detected in the proximal gut of the zven1 treated animals compared to vehicle control, 25.5% and 18.4% respectively. At the 7.8 ug/kg dose, zven1 treated animals had 20% less test meal in the stomach (p=0.001), 16.6% more meal in the proximal gut (p=0.004) and 3.5% more meal in the mid gut. The largest effect was observed with the 77.5 ug/kg animals where gastric emptying was increased approximately 2 fold (37.8% test meal in zven1 treated animals and 63.8% in vehicle treated animals p=0.0002). Intestinal transit was also increased significantly as a greater than 2 fold increase in test meal in the mid gut was measured in the zven1 treated animals over vehicle control (37.1% compared to 15% (p=0.004). At the final, 775 ug/kg dose, increased gastric emptying was detected over control 46.6% compared to 63.8%, but the effect was not as great as the 77.5 μg/kg dose. Increased intestinal transit was detected in the mid gut (26% versus 15%), but the effect was not as significant as that observed with the lower 77.5 ug/kg dose. These data suggest that at higher concentrations, zven1 can inhibit gastric emptying and intestinal transport.

Example 21

Zven1 Activity in Organ Bath

Organ bath testing was also perfomed with Zven1 using at a variety of tissues obtained from guinea pigs. A force transducer was used to record the mechanical contraction using IOX software (EMKa technologies, Falls Church, Va.) and Datanalyst software (EMKa technologies, Falls Church, Va.). Tissues analyzed included: duodenum, jejunum, ileum, trachea, esophagus, aorta, stomach, gall bladder, bladder and uterus.

A. Organ Bath Methods

Two month old male guinea pigs (Hartley, Charles River Labs) weighing ~250 to 300 g were fasted with access to drinking water for ~18 hours then euthanized by $CO_2$ asphyxiation. All tissues were rinsed with Krebs buffer (1.2 mM $MgSO_4$, 115 mM NaCl, 11.5 mM glucose, 23.4 mM $NaHCO_3$, 4.7 mM KCl, 1.2 mM $NaH_2PO_4$, and 2.4 mM $CaCl_2$, oxygenated with 95% $O_2$-5% $CO_2$, pH 7.4, temperature 37° C.) then suspended in the 5 ml organ bath and pre-tensioned. All tissues were tested with positive controls to establish their viability prior to running. Positive controls used were CCK-8, acetylcholine (ACH), histamine, or 5HT, and were purchased from Sigma (Saint Louis, Mo.). All tissues were treated with a vehicle control, phosphate buffered saline (PBS), to rule out the possibility of vehicle effects.

1) Tissues that did not Give a Response to Zven1 in the Organ Bath:

Tracheal ring: 3 mm wide tracheal ring (3 cm away from brachial branches) was collected and allowed to equilibrate at 5 gram tension prior to any treatments. The positive control was 20 ug/ml ACH, which gave an approximate 1 gram deflection. No effect seen with Zven1 at 80 ng/ml.

Aortic ring: 3 mm wide aortic ring (immediately adjacent to aortic arch) was collected and allowed to equilibrate at 4 gram tension prior to any treatments. The positive control was 2 mg/ml KCl, which gave an average one gram deflection. Zven1 at 80 ng/ml did not cause a visible effect.

TABLE 7

Description of treatment groups and results

| Treatment Groups | Number of Animals | % Test Meal in Stomach | % Test Meal in Proximal Gut | % Test Meal in Mid Gut |
|---|---|---|---|---|
| Group I Vehicle (Buffer for zven1) | N = 10 | 63.8% ± 3.8% SE | 18.4% ± 2.4% SE | 15% ± 3.3% SE |
| Group II zven1 0.78 μg/kg body weight | N = 10 | 56.3% ± 5.2% SE | 25.5% ± 4.1% SE | 14.6% ± 4% SE |
| *Group III zven1 7.8 μg/kg body weight | N = 10 | 43.7% ± 3.2% SE *p = .001 | 35.0% ± 5.4% SE *p = .004 | 18.5% ± 5.1% SE |
| *Group IV zven1 77.5 μg/kg body weight | N-10 | 37.8% ± 4.5% SE *p = .0002 | 26.6% ± 5.1% SE | 37.1% ± 7.1% SE *p = .004 |
| *Group V zven1 775 μg/kg body weight | N = 10 | 46.6% ± 4.5% SE *p = .009 | 24.0% ± 5.9% SE | 26% ± 4.3% SE *p = .05 |
| Group VI Caerulein (CCK analogue positive control) 40 ng/g body weight | N = 10 | 93.8% ± 1.0% SE | 2.6% ± 0.9% SE | 1.2% ± 0.3% SE |
| Group VII Sham non-treated | N = 5 | 100% | NA | NA |

Esophagus: 2 cm in length esophagus (2 cm away from cardia) was suspended and allowed to equilibrate at 1 gram tension prior to any treatments. Two mg/ml 5HT gave an approximate 1.4 grams deflection. Zven1 at 20 ng/ml had no visible effect.

Gall bladder: Lumenal fluid was aspirated out with 1 ml syringe then longitudinally suspended and allowed to equilibrate at 1 gram tension prior to any treatments. Five ng/ml of ACH gave a 0.4 gram deflection response. No effect was seen with 20 ng/ml zven1.

Bladder: 1.5 cm×0.3 cm longitudinal strip was suspended and allowed to equilibrate to 0.5 gram tension prior to any treatments. Positive controls induced a contractile response, but no activity was seen at a 80 ng/ml Zven1 dose.

2) Tissues that Responded to Zven1:

Stomach/antrum: 1.5 cm×0.3 cm longitudinal strip was suspended and allowed to equilibrate to 0.5 gram tension prior to any treatments. Treatment with either 5 ng/ml ACH or 80 ng/ml CCK 8 resulted in an approximate one gram deflection. Eighty ng/ml Zven1 also produced a contractile response of approximately 0.5 gm deflection.

Duodenum: 2 cm in length duodenum (2 cm away from pylorus) was suspended and allowed to equilibrate at 1 gram tension prior to any treatments. ACH gave an approximate 0.75 gm deflection. Twenty ng/ml Zven1 also gave a contractile response of approximately 0.5 grams deflection.

Jejunum: 2 cm in length jejunum (midpoint between pylorus and ileal-cecal junction) was suspended and allowed to equilibrate at 1 gram tension prior to any treatments. ACH gave an approximate 1.0 gram deflection and 20 ng/ml Zven1 gave an approximate 0.5 gram deflection contractile response.

Ileum: 8 cm in length ileum (2 cm away from ileal-cecal junction) was collected and flushed with Krebs buffer to remove any fecal debris if present then cut into four equal pieces. All tissues were suspended and allowed to equilibrate at 1 gram tension prior to any treatments. The ileum was run at the same time to compare Zven1 effects on the small intestine. ACH gave an approximate 1.5 gram deflection, and 20 ng/ml Zven1 also gave a 1.5 gram deflection.

Proximal Colon: 2 cm in length colon (2 cm away from cecum) was suspended and allowed to equilibrate at 0.5 gram tension prior to any treatments. Zven1 at 20 ng/ml induced a relaxation effect with a decrease in muscle tone and a decrease in the amplitude of the contractions.

Zven1's contractile effects are specific to the gastrointestinal tract. The greatest contractile response is seen in the ileum, with lesser contraction seen in the duodenum, jejunum, and antrum. The relaxation effect in the proximal colon is suggestive of a coordinated effect on gut motility. As the smooth muscle contraction is enhanced in the antrum and the small intestine, the large intestine is preparing to accommodate the approaching meal by relaxing. Coordinated contractile activity between different parts of the gut will result in improved gastrointestinal function.

Example 22

Comparative Activity of Zven1 and Zven2 in the Organ Bath

Both Zven1 and Zven2 have contractile effects on intestinal tissue in the organ bath. Side by side comparisons were made to compare activity in tissue derived from the same animal.

Ileal strips from guinea pig were tested for contractility using methods described above. Zven2 was purchased from PeproTech Inc. (Rocky Hill, N.J.). Activity was compared at 40, 12, and 3 ng/ml concentrations. ACH at 5 ng/ml was used as a positive control. Contractile responses were normalized to the ACH response in each tissue. All three doses were run on separate ileal longitudinal tissue strips obtained from the same animal.

Results: Contractile effects were normalized to the ACH positive control and are expressed as the ratio of Zven1 or Zven2 to ACH in the table below.

TABLE 13

| Conc (ng/ml) | ACH | Zven1 | Zven1 Zven1:ACH | ACH | Zven2 | Zven2 Zven2:ACH |
|---|---|---|---|---|---|---|
| 40 | 1.26 | 1.28 | 1.02 | 1.25 | 0.58 | 0.46 |
| 12 | 2.5 | 2.51 | 1.00 | 2.26 | 0.61 | .027 |
| 3 | 1.38 | .047 | .034 | 1.73 | .027 | .016 |

Conclusions: Zven1 is approximately twice as active as Zven2 when comparing contractility in the ileum.

Example 23

Synergistic Effects of Zven1 and Zven2

In order to determine the combined effects of Zven1 and zven2 on contractile activity, ileal tissues were pre-treated with varying doses of zven2, followed by increasing doses of zven1.

All tissues are stabilized, treated with ACH, and again stabilized prior to pre-treatment with zven2 at concentrations of 0.8, 3.0 or 12 ng/ml. Zven2 was left on tissue for approximately 20 minutes prior to dosing with 20 ng/ml zven1.

Results: Large 3 gram deflection contractions with Zven1 were observed when the tissue was pre-treated with 0.8 ng/ml zven2. These contractions were larger than what is normally observed with a 20 ng/ml dose of zven1, where contractile effects of approximately 1.5 to 2.0 grams deflection are normally observed. Zven2 alone at 0.8 ng/ml has a negligible contractile effect.

Conclusions: These data suggest that by pre-treating with a low dose of zven2, and then treating with zven1, increased motility effects may be obtained.

Example 24

Effect of Zven1 in Post-Operative Ileus In Vivo

Five to 25 male Sprague-Dawley rats (~240 g) per treatment group were used for these POI studies. Animals were fasted for ~22-23 h (with 2 floor grids placed in their cages to prevent them from having access to their bedding) with free access to water. While under gas isoflurane anesthesia, the rat's abdomen was shaved and wiped with betadine/70% ethanol. A midline incision was then made through the skin and linea alba of the abdomen (3-4 cm long), such that intestines were visible and accessible. The cecum was manipulated for 1 min with sterile saline-soaked gauze, using a gentle, pulsatile-like pressure. This procedure was consistent from animal to animal in order to reduce inter-animal ileus variability. The linea alba was sutured with silk suture and the skin closed with wound clips. Animals were kept on water-jacketed heating pads during recovery from surgery and placed back into their cages once they regained full consciousness.

When fully conscious, rats were administered 1.0 ml of the test meal 15 minutes following completion of cecal manipulation (CM); one minute or 20 minutes later, rats were administered 0.8 or 5 ug/kg BW *E. coli*-produced Zven1, or saline/0.1% w/v/BSA via indwelling jugular venous catheter. Zven1 was diluted with saline/0.1% BSA to the desired concentration (based on average BW of rat [~240 g] and a 0.1 ml injection volume for i.v.) immediately prior to study, using siliconized microfuge tubes.

The test meal consisted of 1.5% (w/v) aqueous methylcellulose solution (medium viscosity methylcellulose from Sigma 400 centipoises; catalog # M-0262) along with a non-absorbable dye, 0.05% (50 mg/100 ml) phenol red (Sigma catalog # P-4758; lot #120K3660). Twenty minutes following administration of the test meal, animals were anesthetized under isoflurane and sacrificed by cervical dislocation. The stomach and intestinal segments were removed, and the amount of phenol red in each segment was determined by spectrophotometric analysis (see below) and expressed as the percent of total phenol red recovered per rat. These values are used to determine the amount of gastric emptying and gut transit per tissue collected.

Colorimetric analysis of phenol red recovered from each gut segment and stomach were performed according to a modification of the procedure outlined by Scarpinato and Bertaccini (1980) and Izbeki et al (2002). Briefly, following euthanization, the stomach and intestinal segments were placed into 20 ml of 0.1 N NaOH and homogenized using a Polytron tissue homogenizer. The Polytron was then rinsed with 5 ml of 0.1 N NaOH and added to the previous 20 ml, along with another 15 ml of 0.1 N NaOH. Homogenate was allowed to settle for at least 1 hour at room temperature. Proteins were precipitated from 5 ml of the supernate by the addition of 0.5 ml of 20% trichloracetic acid. Following centrifugation (3000 rpm for 15 min), 1 ml of supernatant was added to 1 ml of 0.5 N NaOH. A 0.2 ml sample (in a 96-well plate) was read at 560 nm using Molecular Devices Spectra Max 190 spectrophotometer. The extent of gastric emptying and intestinal transit were expressed as percent of total phenol red recovered per rat.

Data indicated that Zven1 (0.8 and 5.0 ug/kg, i.v.) significantly increased gastric emptying and upper intestinal transit of this semi-solid, non-nutritive meal by approximately 1.6 to 2.-fold compared to emptying and transit observed in vehicle-treated rats. Efficacy in this model was observed when these doses of Zven1 are administered at either 1 min or 20 min following meal administration.

Example 25

Effect of i.v. and ip. BV- and *E. Coli*-Produced Zven1 on Gastric Emptying and Intestinal Transit of a Phenol Red Semi-Solid Meal in Rats Male Sprague-Dawley rats (~240 g) were used for this study, with 6-12 animals per treatment group. Animals were fasted for ~24 h (with 2 floor grids placed in their cages to prevent them from having access to their bedding) with free access to water. One minute following the administration of 1.0 ml of test meal, rats were administered varying doses of Zven1 (0.01 to 30 ug/kg BW) or saline/0.1% w/v BSA via indwelling jugular venous catheter. For i.p. dosing, Zven1 (0.1 to 100 ug/kg BW) or saline/0.1% BSA was administered either 1 or 10 min prior to or 1 min after the meal. Zven1 was diluted with saline/0.1% BSA to the desired concentration (based on average BW of rat [~240 g] and a 0.1 ml injection volume for i.v. or 0.5 ml injection volume for i.p.) immediately prior to study, using siliconized microfuge tubes. The test meal consisted of 1.5% (w/v) aqueous methylcellulose solution (medium viscosity methylcellulose from Sigma 400 centipoises; catalog # M-0262) along with a non-absorbable dye, 0.05% (50 mg/100 ml) phenol red (Sigma catalog # P-4758; lot #120K3660). Fifteen or 20 min following administration of the test meal, rats were anesthetized under isoflurane and sacrificed by cervical dislocation.

The stomach and intestinal segments were removed, and the amount of phenol red in each sample was determined by spectrophotometric analysis (see below) and expressed as the percent of total phenol red recovered per rat. These values were used to determine the amount of gastric emptying and gut transit per tissue collected.

Colorimetric analysis of phenol red recovered from each gut segment and stomach were performed according to a modification of the procedure outlined by Scarpinato et al *Arch Int. Pharmacodyn.* 246:286-294 (1980) and Piccinelli et al. *Naunyn-Schmiedeberg's Arch. Pharmacol* 279: 75-82 (1973). Briefly, following euthanization, the stomach and intestinal segments were placed into 20 ml of 0.1 N NaOH and homogenized using a Polytron tissue homogenizer. The Polytron was then rinsed with 5 ml of 0.1 N NaOH and added to the previous 20 ml, along with another 15 ml of 0.1 N NaOH. Homogenate was allowed to settle for at least 1 hour at room temperature. Proteins were precipitated from 5 ml of the supernate by the addition of 0.5 ml of 20% trichloracetic acid. Following centrifugation (3000 rpm for 15 min), 1 ml of supernatant was added to 1 ml of 0.5 N NaOH. A 0.2 ml sample (in a 96-well plate) was read at 560 nm using Molecular Devices Spectra Max 190 spectrophotometer. The extent of gastric emptying and intestinal transit were expressed as percent of total phenol red recovered per rat.

Gastric emptying and intestinal transit of this semi-solid meal were increased by approximately two-fold following i.v. administration of 0.1-1.0 µg/kg BW BV- or *E. coli*-produced Zven1. Inhibitory effects of gastric emptying and intestinal transit were observed using higher doses (10-100 ug/kg BW for i.p. dosing; 30 ug/kg BW for i.v. dosing) of BV- and *E. coli*-Zven1. The inhibitory observations were especially evident when these higher doses of Zven1 were administered i.v. at 1 minute following test meal administration, or when administered i.p. at 10 minutes prior to test meal administration. Similar results were observed when Zven2 was administered i.v. at 30 µg/kg.

Example 26

Effect of i.v. BV- and *E. Coli*-Produced Zven1 on Gastric Emptying and Intestinal Transit of a Phenol Red Semi-Solid Meal in Mice Female C57B1/6 mice, 8 to 10 weeks old, were used for the study, which consisted of eight treatment groups and ~9 mice per group. The animals were fasted for ~20 hrs in cages containing floor screens, and allowed access to water. Animals were weighed to determine proper dose, and their average weight was used to adjust the protein concentration. Zven1 protein (in stock solutions of either 20 mM Mes buffer/20 mM NaCl pH 6.5; or in PBS, pH 7.2) dilutions were prepared in siliconized tubes just prior to injections. Doses were based on the average weight of the study animals (approximately 20 g) and adjusted with saline 0.1% w/v BSA to 0.1 ml injection volumes per mouse. Zven1 and vehicle treatments were administered via i.v. tail vein injection 1-2 minutes prior to receiving 0.15 ml phenol red test meal as an oral gavage. The test meal consisted of 1.5% w/v aqueous methylcellulose solution (medium viscosity carboxy methylcellulose from Sigma with a final viscosity of 400-800 centipoises;

catalog # C-4888; lot #108H0052) containing a non-absorbable dye, 0.05% phenol red (Sigma catalog # P-4758; lot #120K3660). Twenty minutes post-administration of the test meal, animals were euthanized and stomach and intestinal segments removed. The small intestine was measured and divided into three equal segments: proximal, mid and distal gut. The amount of phenol red in each sample was determined by spectrophotometric analysis (as described above for in Examples 20 and 21) and expressed as the percent of total phenol red recovered per mouse. These values were used to determine the amount of gastric emptying and gut transit per tissue collected.

Results indicated that there were increases in gastric emptying and intestinal transit in mice treated with i.v. Zven1 at doses ~1-10 ug/kg BW. Trends toward inhibition of gastric emptying and intestinal transit were observed using higher doses (>50 ug/kg i.v. in mice) of Zven1.

Example 27

Effect of BV- and *E. coli*-Produced Zven1 on Gross Morphology of Stomach and Intestines of Urethane-Anesthetized Rats Studies were conducted in urethane-anesthetized male Sprague-Dawley rats to determine whether i.v. administration of BV- or *E. coli* Zven1 (doses up to and including 30 ug/kg BW; a dose known to induce intestinal motility) affected the gross appearance of the stomach and small intestine.

Rats were fasted (with access to water) on double floor grates in clean cages for ~19 h. Between 07:00 and 08:30 am, rats received an i.p injection of urethane (0.5 ml/100 g BW of a 25% solution) and had a jugular venous catheter inserted. Anesthetized rats were returned to their cages and kept on warming pads (maintained at 37° C.) throughout the day, with additional i.p. doses of urethane administered as needed. An appropriate level of anesthesia was monitored using the toe-pinch reflex test.

At ~5 minute intervals between animals saline was administered via the jugular vein, followed by either vehicle (PBS) or BV- or *E. coli*-produced Zven1 at increasing doses (3, 10 and 30 ug/kg BW; 0.1 ml injection volume) every hour for 3 hours (total of 43 ug/kg BW). Zven1 protein dilutions were prepared just prior to injection. Dose was based on the weight of the study animal (approximately 225 grams) and adjusted so that it was contained in 0.1 ml total volume of diluent (saline/0.1% BSA). Protein was diluted using siliconized microfuge tubes. Rats also received infusions of saline via Harvard pumps at a rate of 0.5 ml per hour. Approximately 8-9 hours later following the initial dose of urethane, rats were sacrificed by cervical dislocation (under anesthesia) and their stomachs and small intestine removed for inspection and morphological evaluation.

There was no evidence of gastric or intestinal lesions in any of the rats. A vehicle-treated rat had some dark fluid within a small segment of the intestinal lumen; there was not any dark fluid observed in the Zven1-treated rats. There was a significant amount of mucous within the intestinal lumen in all treatment groups, most likely as a result of the urethane anesthesia and fasting protocol.

Example 28

Effects of BV-Produced Zven1 on In Vivo Gastrointestinal Contractility in Anesthetized Experimental Mammals "Sonomicrometry" is a technique, which utilizes piezoelectric crystals to measure gastrointestinal distensibility, compliance, and tone in vivo (Sonometrics, Corp. Ontario, Canada). Crystals can be placed anywhere along the gastrointestinal tract in experimental mammals. Peristaltic and segmentation contractions in the stomach and/or intestine can then be accurately quantified and qualified with great detail in response to the administration of Zven1. This system offers a great deal of detailed and sophisticated outcome measures of intestinal motility/contractility.

This method of digital ultrasonomicrometry was used to investigate motility and/or contractility in the ileum, jejunum, cecum and proximal colon as described by Adelson et al. *Gastroenterology* 122, A-554. (2002) in ten rats (two groups of 5 male Sprague-Dawley rats) following an i.v. infusion of the vehicle (saline/0.1% w/v BSA) and escalating doses of BV-produced Zven1. For these experiments, piezoelectric crystals were attached using a small drop of cyanoacrylate glue (Vetbond, 3M Animal Care, St. Paul, Minn.) to the relevant intestinal locations. After laparatomy the urethane anesthetized rats were maintained at 37° C. via a feedback-controlled heater. Sonometric distance signals were acquired continuously at a rate of 50 samples/sec via a digital sonomicrometer (TRX-13, Sonometrics Corp, London ONT) connected to a Pentium III class computer running SonoLAB software (Sonometrics Corp, London, Ontario, Canada). Digitally-acquired distance data were simultaneously recorded as analog signals via an installed 4-channel DAC. These sonometric analog signals, along with all analog physiological data (rectal temperature, blood pressure, EKG, respiratory rate) were acquired using a Microl401 A/D interface (Cambridge Electronic Design, Ltd, Cambridge) connected to a Pentium II class computer running Spike 2 (Cambridge Electronic Design, Ltd, Cambridge) data acquisition software to allow real-time observation and analysis of experiment progress. This method allows simultaneous observation of distance measurements for 4 crystal pairs. Baseline levels were obtained between each vehicle and Zven1 infusion. Both circular and longitudinal motion were monitored using triads of piezoelectric crystals 1 mm in diameter (Sonometrics Corp.) affixed so that two of the three were oriented parallel to the longitudinal axis and the third was oriented to the perpendicular axis.

Motility responses to applied stimuli may comprise tonic and/or phasic components. Tonic and phasic components of responses were analyzed separately. The tonic component of the trace was obtained by replacing each point in the trace with the median value of the trace over the surrounding 10 s. The phasic component was obtained by applying to the original trace the inverse operation of a smoothing function with a 10 s window, i.e. by removing the 'DC component' with a time constant of 10 s. Tonic responses were analyzed in terms of mean value during a response, 1-min maximum excursion from baseline, duration of response, and integrated response (mean normalized response times duration). Phasic activity was analyzed in terms of its rate and amplitude. Changes in relationships between motility in different gut regions measured simultaneously were analyzed using cross-correlation of continuous signals and event correlations of peak positions.

Strong contractility responses were observed in the ileum of Zven 1-treated rats at i.v. doses as low as 3 ug/kg BW; contractions were also noted in the jejunum and duodenum, though not as strong as those observed for the ileum. Responses associated with a relaxation were observed in the proximal colon.

Example 29

Effects of ip. Administration of BV-Produced Zven1 on Distal Colonic Transit in Conscious Mice Adult male C57/BL6 mice (6-8 weeks of age; Harlan, San Diego, Calif.) were used for this study with 6-10 mice per treatment group. Mice were maintained on a 12:12-h light-dark cycle with controlled temperature (21-23° C.) and humidity (30-35%), and were group housed in cages with free access to food (Purina Chow) and tap water. Mice were deprived of food for 18-20 h, with free access to water before the experiments. BV-produced Zven1 in stock solution of 20 mmol MES and 20 mmol NaCl at pH 6.5 was stored at −80° C. On the day of the experiment, Zven1 was diluted to 0.9% NaCl with 0.1% BSA. The pH for both vehicle and Zven1 at various doses was 6.5.

Distal colonic transits were measured as previously described (Martinez V, et al. *J. Pharmacol Exp Ther* 301: 611-617(2002.)). Fasted mice had free access to water and pre-weighed Purina chow for a 1-h period, then were briefly anesthetized with enflurane (1-2 min; Ethrane-Anaquest, Madison, Wis.) and a single 2-mm glass bead was inserted into the distal colon at 2 cm from the anus. Bead insertion was performed with a glass rod with a fire-polished end to avoid tissue damage. After bead insertion the mice were placed individually in their home cages without food and water. Mice regained consciousness within a 1-2 min period and thereafter showed normal behavior. Distal colonic transit was determined to the nearest 0.1 min by monitoring the time required for the expulsion of the glass bead (bead latency).

At the end of the 1 h feeding period, mice were briefly anesthetized with enflurane for bead insertion into the colon followed by the intraperitoneal injection of either vehicle, or Zven1 (3, 10, 30, or 100 µg/kg). Animals were returned to their home cages without food or water and the bead expulsion time was monitored. Results were expressed as Mean±S.E. and analyzed using one-way ANOVA.

In mice, fasted for 18-20 h, re-fed for 1 h, Zven1 injected i.p. (3, 10, 30, and 100 µg/kg) showed no significant changes in bead expulsion time in response to the i.p. injection of BV-Zven1 (3, 10 and 30 µg/kg): 32.7±6.1, 23.1±4.5 and 34.2±5.6 min respectively compared with 21.1±3.9 min in i.p. vehicle injected group. In a second group of mice, treated similarly except administered higher doses of BV-Zven1, the measurement of distal colonic transit showed a dose-related tendency to increase the time at which the bead is expelled in response to the i.p. injection of BV-Zven1 (30 and 100 µg/kg) (29.8±7.8 and 35.1±3.7 min respectively compared with 22.3±5.7 min after i.p. injection of vehicle) although changes did not reach statistical significance.

Example 30

Expression of GPR73a and GPR73b in Rat Gastrointestinal Tract

Rats were fasted overnight and sacrificed. Intestines and stomachs were isolated and four-centimeter tissue sections from the stomach through the end of the colon were immediately flash frozen in liquid nitrogen. Acid-Phenol extraction method was used for RNA isolation. Briefly, tissue sections were grinded in liquid nitrogen then lysed/homogenized in acid guanidium based lysis buffer (4M Guanidine isothyocyanate, 25 mM sodium citrate (pH 7), 0.5% sarcosyl), NaOAc (0.1M final concentration) +βME (1:100). Lysates were spun down; supernatants were mixed with equal volume of acid phenol and 1/10 volume chloroform. After spinning down, equal volume of Isopropanol was added to the aqueous layer. Samples were incubated at −20° C. then pelleted down by spinning. Pellets were washed with 70% EtOH and then resuspended in DEPC treated water.

Taqman EZ RT-PCR Core Reagent Kit (Applied biosystems, Foster City, Calif.) was used to determine GPR73a and GPR73b receptor expression levels. Following manufacturer's instructions, a standard curve was prepared using one of the RNA isolates which had a high quality RNA and which showed expression of both receptors at the same level. Standard curve dilutions of this RNA sample were prepared at the following concentrations: 500 ng/µl, 250 ng/µl, 100 ng/µl and 12.5ng/µl. These standard curve dilutions were first used to test the primers designed for GPR73a and GPR73b genes and for a housekeeping gene, rodent glyceraldehyde-3-phosphate dehydrogenase (GAPDH). Once the working conditions of primer and standard curve were established, RNA samples isolated from rat were tested.

The RNA samples were thawed on ice and diluted to 100 ng/µl in RNase-free water (Invitrogen, Cat #750023). Diluted samples were kept on ice during the experiment. Using the TaqMan EZ RT-PCR Core Reagent Kit (Applied Biosystems, Cat# N808-0236), master mix was prepared for GPR73a, GPR73b receptors and for the house keeping gene. To assay samples in triplicate, 3.5 µl of each RNA samples were aliquoted. For positive controls, 3.5 µl of each standard curve dilutions were used in place of sample RNA. For the negative control, 3.5 µl RNase-free water was used for the no template control. For endogenous controls (rodent GAPDH message), 3.5 µl of both standard curve dilutions and the sample RNAs were aliquoted. Then 84 µl of PCR master mix was added and mixed well by pipetting.

A MicroAmp Optical 96-well Reaction Plate (Applied Biosystems Cat# N801-0560) was placed on ice and 25 µl of RNA/master mix was added in triplicates to the appropriate wells. Then MicroAmp 12-Cap Strips (Applied Biosystems Cat# N801-0534) were used to cover entire plate. Then the plate was spun for two minutes at 3000 RPM in the Qiagen Sigma 4-15 centrifuge.

The samples were run on a PE-ABI 7700 (Perkin Elmer, now EG&G, Inc. Wellesley, Mass.). Sequence Detector was launched and the default was set to Real Time PCR. Fluorochrome was set to FAM. Plate template was set to indicate where standards and where unknown test samples were.

Expression for each sample is reported as a Ct value. The Ct value is the point at which the fluorochrome level or RT-PCR product (a direct reflection of RNA abundance) is amplified to a level, which exceeds the threshold or background level. The lower the Ct value, the higher the expression level, since RT-PCR of a highly expressing sample results in a greater accumulation of fluorochrome/product which crosses the threshold sooner. A Ct value of 40 means that there was no product measured and should result in a mean expression value of zero. The Ct is converted to relative expression value based on comparison to the standard curve. For each sample tested, the amount of GPR73a, GPR73b and GAPDH expression level was determined from the appropriate standard curve. Then these calculated expression values of GPR73a and GPR73b were divided by the GAPDH expression value of each sample in order to obtain a normalized expression for each sample. Each normalized expression value was divided by the normalized-calibrator value to get the relative expression levels. Using GraphPad Prism software, these normalized values were converted to fractions in which the highest expression level was indicated as 1.

the specific antibody target and by ELISA using 500 ng/ml of the recombinant protein Zven1 as specific antibody target. Hybridoma pools positive in either assay protocol are ana-

TABLE 15

Normalized values (represented in fractions) for GPR73a and GPR73b expressions in rat.

| Samples | GPR73a normalized value | StDev | N | Samples | GPR73b normalized value | StDev | N |
|---|---|---|---|---|---|---|---|
| Forestomach | 0.067 | 0.057 | 3 | Forestomach | 0.063 | 0.013 | 3 |
| Fundus | 0.003 | 0.023 | 3 | Fundus | 0.106 | 0.033 | 3 |
| Antrum | 0.000 | 0.016 | 3 | Antrum | 0.000 | 0.004 | 3 |
| Pylorus/Antrum | 0.041 | 0.016 | 3 | Pylorus/Antrum | 0.104 | 0.005 | 3 |
| Duodenum | 0.107 | 0.035 | 3 | Duodenum | 0.205 | 0.037 | 3 |
| Jejunum-1 | 0.102 | 0.035 | 3 | Jejunum-1 | 0.100 | 0.058 | 3 |
| 2 | 0.087 | 0.020 | 3 | 2 | 0.021 | 0.008 | 3 |
| 3 | 0.126 | 0.037 | 3 | 3 | 0.097 | 0.016 | 3 |
| 4 | 0.250 | 0.054 | 3 | 4 | 0.150 | 0.042 | 3 |
| 5 | 0.268 | 0.030 | 3 | 5 | 0.123 | 0.022 | 3 |
| 6 | 0.240 | 0.024 | 3 | 6 | 0.177 | 0.037 | 3 |
| 7 | 0.339 | 0.039 | 3 | 7 | 0.173 | 0.031 | 3 |
| 8 | 0.329 | 0.107 | 3 | 8 | 0.129 | 0.031 | 3 |
| 9 | 0.327 | 0.101 | 3 | 9 | 0.286 | 0.078 | 3 |
| 10 | 0.425 | 0.071 | 3 | 10 | 0.235 | 0.011 | 3 |
| 11 | 0.379 | 0.011 | 3 | 11 | 0.147 | 0.016 | 3 |
| 12 | 0.577 | 0.076 | 3 | 12 | 0.253 | 0.068 | 3 |
| 13 | 0.570 | 0.043 | 3 | 13 | 0.315 | 0.053 | 3 |
| 14 | 0.250 | 0.011 | 3 | 14 | 0.171 | 0.017 | 3 |
| 15 | 0.492 | 0.027 | 3 | 15 | 0.397 | 0.034 | 3 |
| 16 | 0.989 | 0.089 | 3 | 16 | 0.494 | 0.048 | 3 |
| 17 | 0.977 | 0.313 | 3 | 17 | 0.420 | 0.045 | 3 |
| 18 | 1.000 | 0.061 | 3 | 18 | 0.523 | 0.146 | 3 |
| Ileum-1 | 0.797 | 0.080 | 3 | Ileum-1 | 0.630 | 0.141 | 3 |
| 2 | 0.636 | 0.014 | 3 | 2 | 0.434 | 0.080 | 3 |
| 3 | 0.614 | 0.015 | 3 | 3 | 0.441 | 0.115 | 3 |
| 4 | 0.923 | 0.085 | 3 | 4 | 0.871 | 0.288 | 3 |
| 5 | 0.807 | 0.142 | 3 | 5 | 0.739 | 0.017 | 3 |
| 6 | 0.755 | 0.080 | 3 | 6 | 1.000 | 0.246 | 3 |
| Cecum | 0.088 | 0.020 | 3 | Cecum | 0.369 | 0.036 | 3 |
| Proximal | 0.171 | 0.060 | 3 | Proximal | 0.887 | 0.021 | 3 |
| Middle | 0.088 | 0.051 | 3 | Middle | 0.209 | 0.047 | 3 |
| Distal | 0.047 | 0.019 | 3 | Distal | 0.012 | 0.002 | 3 |

Example 31

Zven1 and Monoclonal Antibodies

Rat monoclonal antibodies are prepared by immunizing 4 female Sprague-Dawley Rats (Charles River Laboratories, Wilmington, Mass.), with the purified recombinant protein from Example 6 or Example 7, above. The rats are each given an initial intraperitoneal (IP) injection of 25 □g of the purified recombinant protein in Complete Freund's Adjuvant (Pierce, Rockford, Ill.) followed by booster IP injections of 10 □g of the purified recombinant protein in Incomplete Freund's Adjuvant every two weeks. Seven days after the administration of the second booster injection, the animals are bled and serum is collected.

The Zven1-specific rat sera samples are characterized by ELISA using 1 ug/ml of the purified recombinant protein Zven1 as the specific antibody target.

Splenocytes are harvested from a single high-titer rat and fused to SP2/0 (mouse) myeloma cells using PEG 1500 in a single fusion procedure (4:1 fusion ratio, splenocytes to myeloma cells, "Antibodies: A Laboratory Manual, E. Harlow and D. Lane, Cold Spring Harbor Press). Following 9 days growth post-fusion, specific antibody-producing hybridoma pools are identified by radioimmunoprecipitation (RIP) using the Iodine-125 labeled recombinant protein Zven1 as lyzed further for their ability to block the cell-proliferative activity ("neutralization assay") of purified recombinant protein Zven1 on Baf3 cells expressing the receptor sequence of GPR73a (SEQ ID NO:27) and/or GPR73b (SEQ ID NO:28).

Hybridoma pools yielding positive results by RIP only or RIP and the "neutralization assay" are cloned at least two times by limiting dilution.

Monoclonal antibodies purified from tissue culture media are characterized for their ability to block the cell-proliferative activity ("neutralization assay") of purified recombinant Zven1 on Baf3 cells expressing the receptor sequences. "Neutralizing" monoclonal antibodies are identified in this manner.

A similar procedure is followed to identify monoclonal antibodies to Zven2 using the amino acid sequence in SEQ ID NO:5.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of detecting inflammatory bowel disease in a subject, comprising:
   providing a test sample from the subject;
   providing a control;
   determining the amount of a polynucleotide sequence of SEQ ID NO:4 or a fragment of at least 20 consecutive nucleotides thereof in the test sample from the subject;
   comparing the amount of the polynucleotide sequence or fragment from the test sample with the amount of the polynucleotide or fragment from the control, wherein an increase in the amount of the polynucleotide or fragment in the test sample compared to the amount of the polynucleotide or fragment in the control indicates inflammatory bowel disease.

2. The method according to claim 1, wherein the fragment comprises at least 20 consecutive nucleotides selected from the group consisting of:
   a) the nucleotide sequence of nucleotides 334 to 405 of SEQ ID NO:4; and
   b) the complement of a).

3. The method according to claim 1, wherein the inflammatory bowel disease is ulcerative colitis.

4. The method according to claim 3, wherein the fragment comprises at least 20 consecutive nucleotides selected from the group consisting of:
   a) the nucleotide sequence of nucleotides 334 to 405 of SEQ ID NO:4; and
   b) the complement of a).

5. A method of diagnosing inflammatory bowel disease in a subject, comprising:
   providing a test sample from the subject;
   providing a control;
   measuring the amount of a polynucleotide sequence of SEQ ID NO:4 or a fragment of at least 20 consecutive nucleotides thereof in the sample from the subject; and
   comparing the amount of the polynucleotide or fragment of from the test sample with the amount the polynucleotide or fragment from the control,
   whereby an increase in the amount of the or polynucleotide fragment in the test sample from the subject as compared to the amount of said polynucleotide or fragment in the control indicates inflammatory bowel disease.

6. The method according to claim 5, wherein the fragment comprises at least 20 consecutive nucleotides selected from the group consisting of:
   a) the nucleotide sequence of nucleotides 334 to 405 of SEQ ID NO:4; and
   b) the complement of a).

7. The method according to claim 5, wherein the inflammatory bowel disease is ulcerative colitis.

8. The method according to claim 7, wherein the fragment comprises at least 20 consecutive nucleotides selected from the group consisting of:
   a) the nucleotide sequence of nucleotides 334 to 405 of SEQ ID NO:4; and
   b) the complement of a).

9. The method of claim 1, wherein the test sample and the control are from the same subject.

10. The method of claim 1, wherein the test sample and the control are from different subjects.

11. The method of claim 5, wherein the test sample and the control are from the same subject.

12. The method of claim 5, wherein the sample and the control are from different subjects.

13. The method of claim 1, wherein the control is the level of the polynucleotide or fragment in normal tissue.

14. The method of claim 5, wherein the control is the level of the polynucleotide or fragment in normal tissue.

* * * * *

SEQUENCE LISTING

<160> NUMBER OF SEQ ID NOS: 29

<210> SEQ ID NO 1
<211> LENGTH: 1496
<212> TYPE: DNA
<213> ORGANISM: Homo sapiens
<220> FEATURE:
<221> NAME/KEY: CDS
<222> LOCATION: (66)...(389)

<400> SEQUENCE: 1

```
cgcccttact cactataggg ctcgagcggc cgcccgggca ggtgccgccc agtcccgagg      60 gcgcc atg agg agc ctg tgc tgc gcc cca ctc ctg ctc ctc ttg ctg ctg     110
      Met Arg Ser Leu Cys Cys Ala Pro Leu Leu Leu Leu Leu Leu Leu
       1               5                  10                  15 ccg ccg ctg ctc ctc acg ccc cgc gct ggg gac gcc gcc gtg atc acc      158
Pro Pro Leu Leu Leu Thr Pro Arg Ala Gly Asp Ala Ala Val Ile Thr
             20                  25                  30 ggg gct tgt gac aag gac tcc caa tgt ggt gga ggc atg tgc tgt gct      206
Gly Ala Cys Asp Lys Asp Ser Gln Cys Gly Gly Gly Met Cys Cys Ala
 35                  40                  45 gtc agt atc tgg gtc aag agc ata agg att tgc aca cct atg ggc aaa      254
Val Ser Ile Trp Val Lys Ser Ile Arg Ile Cys Thr Pro Met Gly Lys
     50                  55                  60 ctg gga gac agc tgc cat cca ctg act cgt aaa gtt cca ttt ttt ggg      302
Leu Gly Asp Ser Cys His Pro Leu Thr Arg Lys Val Pro Phe Phe Gly
 65                  70                  75 cgg agg atg cat cac act tgc cca tgt ctg cca ggc ttg gcc tgt tta      350
Arg Arg Met His His Thr Cys Pro Cys Leu Pro Gly Leu Ala Cys Leu
 80                  85                  90                  95 cgg act tca ttt aac cga ttt att tgt tta gcc caa aag taatcgctct      399
Arg Thr Ser Phe Asn Arg Phe Ile Cys Leu Ala Gln Lys
                100                 105 ggagtagaaa ccaaatgtga atagccacat cttacctgta aagtcttact tgtgattgtg    459
ccaaacaaaa aatgtgccag aaagaaatgc tcttgcttcc tcaactttcc aagtaacatt    519
tttatctttg atttgtaaat gattttttt tttttttta tcgaaagaga attttacttt      579
tggatagaaa tatgaagtgt aaggcattat ggaactggtt cttatttccc tgtttgtgtt    639
ttggtttgat ttggcttttt tcttaaatgt caaaaacgta cccatttttca caaaaatgag   699 gaaaataaga atttgatatt ttgttagaaa aactttttt tttttttctc accacccaa      759 gccccatttg tgccctgccg cacaaataca cctacagctt ttggtcccctt gcctcttcca   819 cctcaaagaa tttcaaggct cttaccttac tttattttg tccatttctc ttccctcctc     879
ttgcatttta aagtggaggg tttgtctctt tgagtttgat ggcagaatca ctgatgggaa    939
tccagctttt tgctggcatt taaatagtga aagagtgta tatgtgaact tgacactcca     999
aactcctgtc atggcacgga agctaggagt gctgctggac ccttcctaaa cctgtcactc   1059
aagaggactt cagctctgct gttgggctgg tgtgtggaca gaaggaatgg aaagccaaat   1119
taatttagtc cagatttcta ggtttgggtt tttctaaaaaa taaagatta catttacttc    1179 ttttactttt tataaagttt ttttttccta gtctcctact tagagatatt ctagaaaatg   1239
tcacttgaag aggaagtatt tatttttaatc tggcacaaca ctaattacca tttttaaagc   1299
ggtattaagt tgtaatttaa accttgttg taactgaaag gtcgattgta atggattgcc     1359
gtttgtacct gtatcagtat tgctgtgtaa aaattctgta tcagaataat aacagtactg   1419
```

```
tatatcattt gatttattttt aatattatat ccttattttt gtcaaaaaaa aaaaaaaaa    1479 aaaaatatgc ggccgcg                                                   1496

<210> SEQ ID NO 2
<211> LENGTH: 108
<212> TYPE: PRT
<213> ORGANISM: Homo sapiens

<400> SEQUENCE: 2

Met Arg Ser Leu Cys Cys Ala Pro Leu Leu Leu Leu Leu Pro
  1               5                  10                  15

Pro Leu Leu Leu Thr Pro Arg Ala Gly Asp Ala Val Ile Thr Gly
                 20                  25                  30

Ala Cys Asp Lys Asp Ser Gln Cys Gly Gly Met Cys Cys Ala Val
             35                  40                  45

Ser Ile Trp Val Lys Ser Ile Arg Ile Cys Thr Pro Met Gly Lys Leu
 50                  55                  60

Gly Asp Ser Cys His Pro Leu Thr Arg Lys Val Pro Phe Phe Gly Arg
 65                  70                  75                  80

Arg Met His His Thr Cys Pro Cys Leu Pro Gly Leu Ala Cys Leu Arg
                 85                  90                  95

Thr Ser Phe Asn Arg Phe Ile Cys Leu Ala Gln Lys
                100                 105

<210> SEQ ID NO 3
<211> LENGTH: 324
<212> TYPE: DNA
<213> ORGANISM: Artificial Sequence
<220> FEATURE:
<223> OTHER INFORMATION: This degenerate sequence encodes the amino acid
      sequence of SEQ ID NO:2.
<220> FEATURE:
<221> NAME/KEY: misc_feature
<222> LOCATION: (1)...(324)
<223> OTHER INFORMATION: n = A,T,C or G

<400> SEQUENCE: 3
atgmgnwsny tntgytgygc nccnytnytn ytnytnytny tnytnccncc nytnytnytn     60
acnccnmgng cnggngaygc ngcngtnath acnggngcnt gygayaarga ywsncartgy    120
ggnggnggna tgtgytgygc ngtnwsnath tgggtnaarw snathmgnat htgyacnccn    180
atgggnaary tnggngayws ntgycayccn ytnacnmgna argtnccntt yttyggnmgn    240
mgnatgcayc ayacntgycc ntgyytnccn ggnytngcnt gyytnmgnac nwsnttyaay    300
mgnttyatht gyytngcnca raar                                           324

<210> SEQ ID NO 4
<211> LENGTH: 1409
<212> TYPE: DNA
<213> ORGANISM: Homo sapiens
<220> FEATURE:
<221> NAME/KEY: CDS
<222> LOCATION: (91)...(405)

<400> SEQUENCE: 4
tggcctcccc agcttgccag gcacaaggct gagcgggagg aagcgagagg catctaagca     60
ggcagtgttt tgccttcacc ccaagtgacc atg aga ggt gcc acg cga gtc tca    114
                                Met Arg Gly Ala Thr Arg Val Ser
                                  1               5
```

```
atc atg ctc ctc cta gta act gtg tct gac tgt gct gtg atc aca ggg      162
Ile Met Leu Leu Leu Val Thr Val Ser Asp Cys Ala Val Ile Thr Gly
    10                  15                  20 gcc tgt gag cgg gat gtc cag tgt ggg gca ggc acc tgc tgt gcc atc      210
Ala Cys Glu Arg Asp Val Gln Cys Gly Ala Gly Thr Cys Cys Ala Ile
25                  30                  35                  40 agc ctg tgg ctt cga ggg ctg cgg atg tgc acc ccg ctg ggg cgg gaa      258
Ser Leu Trp Leu Arg Gly Leu Arg Met Cys Thr Pro Leu Gly Arg Glu
                45                  50                  55 ggc gag gag tgc cac ccc ggc agc cac aag gtc ccc ttc ttc agg aaa      306
Gly Glu Glu Cys His Pro Gly Ser His Lys Val Pro Phe Phe Arg Lys
            60                  65                  70 cgc aag cac cac acc tgt cct tgc ttg ccc aac ctg ctg tgc tcc agg      354
Arg Lys His His Thr Cys Pro Cys Leu Pro Asn Leu Leu Cys Ser Arg
        75                  80                  85 ttc ccg gac ggc agg tac cgc tgc tcc atg gac ttg aag aac atc aat      402
Phe Pro Asp Gly Arg Tyr Arg Cys Ser Met Asp Leu Lys Asn Ile Asn
    90                  95                  100 ttt taggcgcttg cctggtctca ggatacccac catcctttc ctgagcacag            455
Phe
105 cctggatttt tatttctgcc atgaaaccca gctcccatga ctctcccagt ccctacactg    515
actaccctga tctctcttgt ctagtacgca catatgcaca caggcagaca tacctcccat    575
catgacatgg tccccaggct ggcctgagga tgtcacagct tgaggctgtg gtgtgaaagg    635
tggccagcct ggttctcttc cctgctcagg ctgccagaga ggtggtaaat ggcagaaagg    695
acattccccc tcccctcccc aggtgacctg ctctctttcc tgggccctgc ccctctcccc    755
acatgtatcc ctcggtctga attagacatt cctgggcaca ggctcttggg tgcattgctc    815
agagtcccag gtcctggcct gaccctcagg cccttcacgt gaggtctgtg aggaccaatt    875
tgtgggtagt tcatcttccc tcgattggtt aactccttag tttcagacca cagactcaag    935
attggctctt cccagagggc agcagacagt cacccaagg caggtgtagg gagcccaggg     995
aggccaatca gccccctgaa gactctggtc ccagtcagcc tgtggcttgt ggcctgtgac   1055
ctgtgacctt ctgccagaat tgtcatgcct ctgaggcccc tcttaccac actttaccag    1115
ttaaccactg aagcccccaa ttcccacagc ttttccatta aaatgcaaat ggtggtggtt   1175
caatctaatc tgatattgac atattagaag gcaattaggg tgtttcctta aacaactcct   1235
ttccaaggat cagccctgag agcaggttgg tgactttgag gagggcagtc ctctgtccag   1295
attggggtgg gagcaaggga cagggagcag ggcaggggct gaaaggggca ctgattcaga   1355
ccagggaggc aactacacac caacctgctg gctttagaat aaaagcacca actg          1409

<210> SEQ ID NO 5
<211> LENGTH: 105
<212> TYPE: PRT
<213> ORGANISM: Homo sapiens

<400> SEQUENCE: 5

Met Arg Gly Ala Thr Arg Val Ser Ile Met Leu Leu Val Thr Val
1               5                   10                  15

Ser Asp Cys Ala Val Ile Thr Gly Ala Cys Glu Arg Asp Val Gln Cys
                20                  25                  30

Gly Ala Gly Thr Cys Cys Ala Ile Ser Leu Trp Leu Arg Gly Leu Arg
            35                  40                  45

Met Cys Thr Pro Leu Gly Arg Glu Gly Glu Glu Cys His Pro Gly Ser
        50                  55                  60
```

His Lys Val Pro Phe Phe Arg Lys Arg Lys His His Thr Cys Pro Cys
65                  70                  75                  80

Leu Pro Asn Leu Leu Cys Ser Arg Phe Pro Asp Gly Arg Tyr Arg Cys
                85                  90                  95

Ser Met Asp Leu Lys Asn Ile Asn Phe
            100                 105

<210> SEQ ID NO 6
<211> LENGTH: 315
<212> TYPE: DNA
<213> ORGANISM: Artificial Sequence
<220> FEATURE:
<223> OTHER INFORMATION: This degenerate sequence encodes the amino acid
      sequence of SEQ ID NO:5.
<220> FEATURE:
<221> NAME/KEY: misc_feature
<222> LOCATION: (1)...(315)
<223> OTHER INFORMATION: n = A,T,C or G

<400> SEQUENCE: 6
atgmgnggng cnacnmgngt nwsnathatg ytnytnytng tnacngtnws ngaytgygcn      60
gtnathacng gngcntgyga rmgngaygtn cartgyggng cnggnacntg ytgygcnath    120
wsnytntggy tnmgnggnyt nmgnatgtgy acnccnytng gnmgngargg ngargartgy    180
cayccnggnw sncayaargt nccnttytty mgnaarmgna arcaycayac ntgyccntgy    240
ytnccnaayy tnytntgyws nmgnttyccn gayggnmgnt aymgntgyws natggayytn    300
aaraayatha aytty                                                     315

<210> SEQ ID NO 7
<211> LENGTH: 16
<212> TYPE: PRT
<213> ORGANISM: Artificial Sequence
<220> FEATURE:
<223> OTHER INFORMATION: Peptide linker.

<400> SEQUENCE: 7

Gly Gly Ser Gly Gly Ser Gly Gly Gly Ser Gly Gly Gly Gly Ser
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Motif.
<220> FEATURE:
<221> NAME/KEY: VARIANT
<222> LOCATION: (8)...(8)
<223> OTHER INFORMATION: Xaa is Asp or Glu.
<220> FEATURE:
<221> NAME/KEY: VARIANT
<222> LOCATION: (9)...(9)
<223> OTHER INFORMATION: Xaa is Lys or Arg.
<220> FEATURE:
<221> NAME/KEY: VARIANT
<222> LOCATION: (1)...(10)
<223> OTHER INFORMATION: Xaa = Any Amino Acid
<220> FEATURE:
<221> NAME/KEY: VARIANT
<222> LOCATION: (1)...(10)
<223> OTHER INFORMATION: Xaa = Any Amino Acid

<400> SEQUENCE: 8

Ala Val Ile Thr Gly Ala Cys Xaa Xaa Asp
1               5                   10

```
<210> SEQ ID NO 9
<211> LENGTH: 23
<212> TYPE: PRT
<213> ORGANISM: Artificial Sequence
<220> FEATURE:
<223> OTHER INFORMATION: Motif.
<220> FEATURE:
<221> NAME/KEY: VARIANT
<222> LOCATION: (4)...(4)
<223> OTHER INFORMATION: Xaa is Gly or Leu.
<220> FEATURE:
<221> NAME/KEY: VARIANT
<222> LOCATION: (5)...(5)
<223> OTHER INFORMATION: Xaa is Ser or Thr.
<220> FEATURE:
<221> NAME/KEY: VARIANT
<222> LOCATION: (6)...(6)
<223> OTHER INFORMATION: Xaa is His or Arg.
<220> FEATURE:
<221> NAME/KEY: VARIANT
<222> LOCATION: (12)...(12)
<223> OTHER INFORMATION: Xaa is any amino acid.
<220> FEATURE:
<221> NAME/KEY: VARIANT
<222> LOCATION: (13)...(13)
<223> OTHER INFORMATION: Xaa is Lys or Arg.
<220> FEATURE:
<221> NAME/KEY: VARIANT
<222> LOCATION: (15)...(15)
<223> OTHER INFORMATION: Xaa is any amino acid.

<400> SEQUENCE: 9

Cys His Pro Xaa Xaa Xaa Lys Val Pro Phe Phe Xaa Xaa Arg Xaa His
 1               5                  10                  15

His Thr Cys Pro Cys Leu Pro
            20

<210> SEQ ID NO 10
<211> LENGTH: 6
<212> TYPE: PRT
<213> ORGANISM: Artificial Sequence
<220> FEATURE:
<223> OTHER INFORMATION: Glu-Glu tag

<400> SEQUENCE: 10

Glu Tyr Met Pro Met Glu
 1               5

<210> SEQ ID NO 11
<211> LENGTH: 249
<212> TYPE: DNA
<213> ORGANISM: Homo sapiens

<400> SEQUENCE: 11
atggccgtga tcaccggggc ttgtgacaag gactcccaat gtggtggagg catgtgctgt      60
gctgtcagta tctgggtcaa gagcataagg atttgcacac ctatgggcaa actgggagac     120
agctgccatc cactgactcg taaagttcca tttttggggc ggaggatgca tcacacttgc     180
ccgtgtctgc caggcttggc ctgtttacgg acttcattta accgatttat tgtttagcc      240 caaaagtaa                                                             249

<210> SEQ ID NO 12
<211> LENGTH: 68
<212> TYPE: DNA
<213> ORGANISM: Artificial Sequence
<220> FEATURE:
<223> OTHER INFORMATION: oligonucleotide primer ZC40821
```

-continued

```
<400> SEQUENCE: 12
ctagaaataa ttttgtttaa ctttaagaag gagatatata tatggccgtg atcaccgggg    60
cttgtgac                                                              68

<210> SEQ ID NO 13
<211> LENGTH: 67
<212> TYPE: DNA
<213> ORGANISM: Artificial Sequence
<220> FEATURE:
<223> OTHER INFORMATION: oligonucleotide primer ZC40813

<400> SEQUENCE: 13
tctgtatcag gctgaaaatc ttatctcatc cgccaaaaca ttactttgg gctaaacaaa     60 taaatcg                                                               67

<210> SEQ ID NO 14
<211> LENGTH: 249
<212> TYPE: DNA
<213> ORGANISM: Artificial Sequence
<220> FEATURE:
<223> OTHER INFORMATION: Codon optimized polynucleotide sequence for
      Zven1

<400> SEQUENCE: 14
atggctgtta ttaccggtgc ttgcgacaaa gactctcagt gtggtggtgg tatgtgctgc    60
gctgtttcta tctgggttaa atctatccgt atctgcactc ctatgggtaa actgggtgac   120
tcttgccatc cgctgactcg taaagttccg ttcttcggtc gtcgtatgca tcacacctgt   180
ccgtgcctgc cgggtctggc ttgcctgcgt acctctttca ccgtttcat ttgcctggct    240 cagaagtaa                                                            249

<210> SEQ ID NO 15
<211> LENGTH: 79
<212> TYPE: DNA
<213> ORGANISM: Artificial Sequence
<220> FEATURE:
<223> OTHER INFORMATION: Oligonucleotide primer ZC45,048

<400> SEQUENCE: 15
agtcaatgga tgacaagaat cacccaactt acccatagga gtacaaattc tgatagactt    60
aacccaaata gaaacagca                                                 79

<210> SEQ ID NO 16
<211> LENGTH: 77
<212> TYPE: DNA
<213> ORGANISM: Artificial Sequence
<220> FEATURE:
<223> OTHER INFORMATION: Oligonucleotide primer ZC45049

<400> SEQUENCE: 16
ttcttgtcat ccattgacta gaaaggttcc attctttggt agaaggatgc atcacacttg    60
tccatgtttg ccaggtt                                                   77

<210> SEQ ID NO 17
<211> LENGTH: 70
<212> TYPE: DNA
<213> ORGANISM: Artificial Sequence
<220> FEATURE:
<223> OTHER INFORMATION: Oligonucleotide primer ZC45050
```

-continued

```
<400> SEQUENCE: 17 ttactttga gccaaacaaa tgaatctgtt gaaagaagtt ctcaaacaag ccaaacctgg      60
caaacatgga                                                           70

<210> SEQ ID NO 18
<211> LENGTH: 68
<212> TYPE: DNA
<213> ORGANISM: Artificial Sequence
<220> FEATURE:
<223> OTHER INFORMATION: Oligonucleotide primer ZC45051

<400> SEQUENCE: 18
attactggtg cttgtgataa ggattctcaa tgtggtggtg gtatgtgttg tgctgtttct      60
atttgggt                                                             68

<210> SEQ ID NO 19
<211> LENGTH: 65
<212> TYPE: DNA
<213> ORGANISM: Artificial Sequence
<220> FEATURE:
<223> OTHER INFORMATION: Oligonucleotide primer ZC45052

<400> SEQUENCE: 19
ttatcacaag caccagtaat aacagcagca tcaccggctc ttggagtcaa caacaatggt      60
ggcaa                                                                65

<210> SEQ ID NO 20
<211> LENGTH: 59
<212> TYPE: DNA
<213> ORGANISM: Artificial Sequence
<220> FEATURE:
<223> OTHER INFORMATION: Oligonucleotide primer ZC45053

<400> SEQUENCE: 20
atgagatctt tgtgttgtgc tccattgttg ttgttgttgt tgttgccacc attgttgtt       59

<210> SEQ ID NO 21
<211> LENGTH: 1182
<212> TYPE: DNA
<213> ORGANISM: Homo sapiens

<400> SEQUENCE: 21
atggagacca ccatggggtt catggatgac aatgccacca acacttccac cagcttcctt      60
tctgtgctca accctcatgg agcccatgcc acttccttcc cattcaactt cagctacagc     120
gactatgata tgccttttga tgaagatgag gatgtgacca attccaggac gttctttgct     180
gccaagattg tcattgggat ggccctggtg ggcatcatgc tggtctgcgg cattggaaac     240
ttcatcttta cgctgccct ggtccgctac aagaaactgc gcaacctcac caacctgctc     300
atcgccaacc tggccatctc tgacttcctg gtggccattg tctgctgccc ctttgagatg     360
gactactatg tggtgcgcca gctctcctgg gagcacggcc acgtcctgtg cacctctgtc     420
aactacctgc gcactgtctc tctctatgtc tccaccaatg ccctgctggc catcgccatt     480
gacaggtatc tggctattgt ccatccgctg agaccacgga tgaagtgcca acagccact      540 ggcctgattg ccttggtgtg gacggtgtcc atcctgatcg ccatccctc cgcctacttc     600 accaccgaga cggtcctcgt cattgtcaag agccaggaaa agatcttctg cggccagatc     660
tggcctgtgg accagcagct ctactacaag tcctacttcc tctttatctt tggcatagaa     720
ttcgtgggcc ccgtggtcac catgacccctg tgctatgcca ggatctcccg ggagctctgg     780
```

| | |
|---|---|
| ttcaaggcgg tccctggatt ccagacagag cagatccgca agaggctgcg ctgccgcagg | 840 |
| aagacggtcc tggtgctcat gtgcatcctc accgcctacg tgctatgctg ggcgcccttc | 900 |
| tacggcttca ccatcgtgcg cgacttcttc cccaccgtgt ttgtgaagga gaagcactac | 960 |
| ctcactgcct tctacatcgt cgagtgcatc gccatgagca cagcatgat caacactctg | 1020 |
| tgcttcgtga ccgtcaagaa cgacaccgtc aagtacttca aaaagatcat gttgctccac | 1080 |
| tggaaggctt cttacaatgg cggtaagtcc agtgcagacc tggacctcaa gacaattggg | 1140 |
| atgcctgcca ccgaagaggt ggactgcatc agactaaaat aa | 1182 |

<210> SEQ ID NO 22
<211> LENGTH: 1155
<212> TYPE: DNA
<213> ORGANISM: Homo sapiens

<400> SEQUENCE: 22

| | |
|---|---|
| atggcagccc agaatggaaa caccagtttc acacccaact ttaatccacc ccaagaccat | 60 |
| gcctcctccc tctcctttaa cttcagttat ggtgattatg acctccctat ggatgaggat | 120 |
| gaggacatga ccaagacccg gaccttcttc gcagccaaga tcgtcattgg cattgcactg | 180 |
| gcaggcatca tgctggtctg cggcatcggt aactttgtct ttatcgctgc cctcacccgc | 240 |
| tataagaagt gcgcaaccct caccaatctg ctcattgcca acctggccat ctccgacttc | 300 |
| ctggtggcca tcatctgctg cccccttcgag atggactact acgtggtacg gcagctctcc | 360 |
| tgggagcatg gccacgtgct ctgtgcctcc gtcaactacc tgcgcaccgt ctccctctac | 420 |
| gtctccacca atgccttgct ggccattgcc attgacagat atctcgccat cgttcacccc | 480 |
| ttgaaaccac ggatgaatta tcaaacggcc tccttcctga tcgccttggt ctggatggtg | 540 |
| tccattctca ttgccatccc atcggcttac tttgcaacag aaacggtcct ctttattgtc | 600 |
| aagagccagg agaagatctt ctgtggccag atctggcctg tggatcagca gctctactac | 660 |
| aagtcctact tcctcttcat ctttggtgtc gagttcgtgg gccctgtggt caccatgacc | 720 |
| ctgtgctatg ccaggatctc ccgggagctc tggttcaagg cagtccctgg gttccagacg | 780 |
| gagcagattc gcaagcggct gcgctgccgc aggaagacgg tcctggtgct catgtgcatt | 840 |
| ctcacggcct atgtgctgtg ctgggcaccc ttctacggtt tcaccatcgt tcgtgacttc | 900 |
| ttccccactg tgttcgtgaa ggaaaagcac tacctcactg ccttctacgt ggtcgagtgc | 960 |
| atcgccatga gcaacagcat gatcaacacc gtgtgcttcg tgacggtcaa gaacaacacc | 1020 |
| atgaagtact tcaagaagat gatgctgctg cactggcgtc cctcccagcg ggggagcaag | 1080 |
| tccagtgctg accttgacct cagaaccaac gggggtgccca ccacagaaga ggtggactgt | 1140 |
| atcaggctga agtga | 1155 |

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide primer ZC29463

<400> SEQUENCE: 23

| | |
|---|---|
| ggaattcatg aggagcctgt gctgcgcc | 28 |

<210> SEQ ID NO 24
<211> LENGTH: 31
<212> TYPE: DNA
<213> ORGANISM: Artificial Sequence

```
<220> FEATURE:
<223> OTHER INFORMATION: Oligonucleotide primer ZC29462

<400> SEQUENCE: 24
gctctagacc cttttgggct aaacaaataa a                              31

<210> SEQ ID NO 25
<211> LENGTH: 348
<212> TYPE: DNA
<213> ORGANISM: Artificial Sequence
<220> FEATURE:
<223> OTHER INFORMATION: Expression sequence

<400> SEQUENCE: 25
atgaggagcc tgtgctgcgc cccactcctg ctcctcttgc tgctgccgcc gctgctgctc       60
acgccccgcg ctggggacgc cgccgtgatc accggggctt gtgacaagga ctcccaatgt      120
ggtggaggca tgtgctgtgc tgtcagtatc tgggtcaaga gcataaggat ttgcacacct      180
atgggcaaac tgggagacag ctgccatcca ctgactcgta aagttccatt ttttgggcgg      240
aggatgcatc acacttgccc gtgtctgcca ggcttggcct gtttacggac ttcatttaac      300
cgatttattt gtttagccca aaagggtcta gaatacatgc cgatggac                   348

<210> SEQ ID NO 26
<211> LENGTH: 116
<212> TYPE: PRT
<213> ORGANISM: Artificial Sequence
<220> FEATURE:
<223> OTHER INFORMATION: Expression sequence with Gly linker and
      Glu-Glu-tag

<400> SEQUENCE: 26

Met Arg Ser Leu Cys Cys Ala Pro Leu Leu Leu Leu Leu Leu Pro
 1               5                  10                  15

Pro Leu Leu Leu Thr Pro Arg Ala Gly Asp Ala Ala Val Ile Thr Gly
            20                  25                  30

Ala Cys Asp Lys Asp Ser Gln Cys Gly Gly Gly Met Cys Cys Ala Val
        35                  40                  45

Ser Ile Trp Val Lys Ser Ile Arg Ile Cys Thr Pro Met Gly Lys Leu
    50                  55                  60

Gly Asp Ser Cys His Pro Leu Thr Arg Lys Val Pro Phe Phe Gly Arg
65                  70                  75                  80

Arg Met His His Thr Cys Pro Cys Leu Pro Gly Leu Ala Cys Leu Arg
                85                  90                  95

Thr Ser Phe Asn Arg Phe Ile Cys Leu Ala Gln Lys Gly Leu Glu Tyr
            100                 105                 110

Met Pro Met Asp
        115

<210> SEQ ID NO 27
<211> LENGTH: 393
<212> TYPE: PRT
<213> ORGANISM: Homo sapiens

<400> SEQUENCE: 27

Met Glu Thr Thr Met Gly Phe Met Asp Asp Asn Ala Thr Asn Thr Ser
 1               5                  10                  15

Thr Ser Phe Leu Ser Val Leu Asn Pro His Gly Ala His Ala Thr Ser
            20                  25                  30
```

-continued

Phe Pro Phe Asn Phe Ser Tyr Ser Asp Tyr Asp Met Pro Leu Asp Glu
            35                  40                  45

Asp Glu Asp Val Thr Asn Ser Arg Thr Phe Phe Ala Ala Lys Ile Val
     50                  55                  60

Ile Gly Met Ala Leu Val Gly Ile Met Leu Val Cys Gly Ile Gly Asn
 65                  70                  75                  80

Phe Ile Phe Ile Ala Ala Leu Val Arg Tyr Lys Lys Leu Arg Asn Leu
                 85                  90                  95

Thr Asn Leu Leu Ile Ala Asn Leu Ala Ile Ser Asp Phe Leu Val Ala
             100                 105                 110

Ile Val Cys Cys Pro Phe Glu Met Asp Tyr Tyr Val Arg Gln Leu
             115                 120                 125

Ser Trp Glu His Gly His Val Leu Cys Thr Ser Val Asn Tyr Leu Arg
         130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                 165                 170                 175

Gln Thr Ala Thr Gly Leu Ile Ala Leu Val Trp Thr Val Ser Ile Leu
             180                 185                 190

Ile Ala Ile Pro Ser Ala Tyr Phe Thr Thr Glu Thr Val Leu Val Ile
             195                 200                 205

Val Lys Ser Gln Glu Lys Ile Phe Cys Gly Gln Ile Trp Pro Val Asp
     210                 215                 220

Gln Gln Leu Tyr Tyr Lys Ser Tyr Phe Leu Phe Ile Phe Gly Ile Glu
225                 230                 235                 240

Phe Val Gly Pro Val Val Thr Met Thr Leu Cys Tyr Ala Arg Ile Ser
                 245                 250                 255

Arg Glu Leu Trp Phe Lys Ala Val Pro Gly Phe Gln Thr Glu Gln Ile
                 260                 265                 270

Arg Lys Arg Leu Arg Cys Arg Arg Lys Thr Val Leu Val Leu Met Cys
     275                 280                 285

Ile Leu Thr Ala Tyr Val Leu Cys Trp Ala Pro Phe Tyr Gly Phe Thr
 290                 295                 300

Ile Val Arg Asp Phe Phe Pro Thr Val Phe Val Lys Glu Lys His Tyr
305                 310                 315                 320

Leu Thr Ala Phe Tyr Ile Val Glu Cys Ile Ala Met Ser Asn Ser Met
                 325                 330                 335

Ile Asn Thr Leu Cys Phe Val Thr Val Lys Asn Asp Thr Val Lys Tyr
             340                 345                 350

Phe Lys Lys Ile Met Leu Leu His Trp Lys Ala Ser Tyr Asn Gly Gly
         355                 360                 365

Lys Ser Ser Ala Asp Leu Asp Leu Lys Thr Ile Gly Met Pro Ala Thr
     370                 375                 380

Glu Glu Val Asp Cys Ile Arg Leu Lys
385                 390

<210> SEQ ID NO 28
<211> LENGTH: 384
<212> TYPE: PRT
<213> ORGANISM: Homo sapiens

```
<400> SEQUENCE: 28

Met Ala Ala Gln Asn Gly Asn Thr Ser Phe Thr Pro Asn Phe Asn Pro
 1               5                  10                  15

Pro Gln Asp His Ala Ser Ser Leu Ser Phe Asn Phe Ser Tyr Gly Asp
                20                  25                  30

Tyr Asp Leu Pro Met Asp Glu Asp Asp Met Thr Lys Thr Arg Thr
            35                  40                  45

Phe Phe Ala Ala Lys Ile Val Ile Gly Ile Ala Leu Ala Gly Ile Met
 50                  55                  60

Leu Val Cys Gly Ile Gly Asn Phe Val Phe Ile Ala Ala Leu Thr Arg
 65                  70                  75                  80

Tyr Lys Lys Leu Arg Asn Leu Thr Asn Leu Leu Ile Ala Asn Leu Ala
                85                  90                  95

Ile Ser Asp Phe Leu Val Ala Ile Ile Cys Cys Pro Phe Glu Met Asp
                100                 105                 110

Tyr Tyr Val Val Arg Gln Leu Ser Trp Glu His Gly His Val Leu Cys
            115                 120                 125

Ala Ser Val Asn Tyr Leu Arg Thr Val Ser Leu Tyr Val Ser Thr Asn
130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
                180                 185                 190

Thr Glu Thr Val Leu Phe Ile Val Lys Ser Gln Glu Lys Ile Phe Cys
            195                 200                 205

Gly Gln Ile Trp Pro Val Asp Gln Gln Leu Tyr Tyr Lys Ser Tyr Phe
210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
                260                 265                 270

Thr Val Leu Val Leu Met Cys Ile Leu Thr Ala Tyr Val Leu Cys Trp
            275                 280                 285

Ala Pro Phe Tyr Gly Phe Thr Ile Val Arg Asp Phe Phe Pro Thr Val
290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
                340                 345                 350

Arg Pro Ser Gln Arg Gly Ser Lys Ser Ser Ala Asp Leu Asp Leu Arg
            355                 360                 365

Thr Asn Gly Val Pro Thr Thr Glu Glu Val Asp Cys Ile Arg Leu Lys
370                 375                 380

<210> SEQ ID NO 29
<211> LENGTH: 129
<212> TYPE: PRT
<213> ORGANISM: Homo sapiens
```

-continued

```
<400> SEQUENCE: 29

Met Arg Ser Leu Cys Cys Ala Pro Leu Leu Leu Leu Leu Leu Pro
  1               5                  10                  15

Pro Leu Leu Leu Thr Pro Arg Ala Gly Asp Ala Ala Val Ile Thr Gly
             20                  25                  30

Ala Cys Asp Lys Asp Ser Gln Cys Gly Gly Gly Met Cys Cys Ala Val
             35                  40                  45

Ser Ile Trp Val Lys Ser Ile Arg Ile Cys Thr Pro Met Gly Lys Leu
     50                  55                  60

Gly Asp Ser Cys His Pro Leu Thr Arg Lys Asn Asn Phe Gly Asn Gly
 65                  70                  75                  80

Arg Gln Glu Arg Arg Lys Arg Lys Arg Ser Lys Arg Lys Lys Glu Val
             85                  90                  95

Pro Phe Phe Gly Arg Arg Met His His Thr Cys Pro Cys Leu Pro Gly
            100                 105                 110

Leu Ala Cys Leu Arg Thr Ser Phe Asn Arg Phe Ile Cys Leu Ala Gln
            115                 120                 125

Lys
```